United States Patent [19]

Rosati

[11] 4,348,264

[45] Sep. 7, 1982

[54] PHOTOCATALYZED PROCESS FOR PRODUCING CARBAPENAMS AND CARBAPEN-2-EMS

[75] Inventor: Robert L. Rosati, Stonington, Conn.

[73] Assignee: Pfizer Inc., New York, N.Y.

[21] Appl. No.: 232,156

[22] Filed: Feb. 9, 1981

Related U.S. Application Data

[63] Continuation-in-part of Ser. No. 149,604, May 14, 1980, abandoned.

[51] Int. Cl.$^3$ .............................................. B01J 19/12
[52] U.S. Cl. .............................................. 204/158 R
[58] Field of Search ............ 204/158 N, 158 T, 158 R

[56] References Cited

U.S. PATENT DOCUMENTS 3,592,751  7/1971  Archer et al. .................. 204/158 R
4,208,422  6/1980  Christensen et al. ................ 424/274
4,234,596  11/1980  Christenson et al. ............ 260/245.2

FOREIGN PATENT DOCUMENTS 867227  11/1978  Belgium .

OTHER PUBLICATIONS

Kemetani et al., Heterocycles, 12, pp. 1189–1190 (1979).
Onoue et al., Tetrahedron Letters No. 40, pp. 3867–3870 (1979).
Baxter et al., J. Chem. Soc. Chem. Commun. 1979, pp. 236–237 (1979).
Cama and Christensen, J. Am. Chem. Soc., 100, pp. 8006–8007 (1979).
Ratcliffe et al., Tetrahedron Letters 21, pp. 31–34 (1980).

*Primary Examiner*—Howard S. Williams
*Attorney, Agent, or Firm*—Charles J. Knuth; Albert E. Frost; Robert K. Blackwood

[57] ABSTRACT

Carbapenam-3-carboxylic acids and carbapen-2-em-3-carboxylic acids substituted at the 1-position with an oxo, a hydroxy or an acetoxy group, variously substituted at the 2-position with such groups as methyl, acetoxymethyl, methanesulfonyloxy, alkoxy, alkylthio, aminoalkylthio or amidinoalkylthio and optionally substituted at the 6-position with a hydroxyalkyl group, an acetoxyalkyl group or a conventional penicillin side-chain, pharmaceutically-acceptable salts thereof and various esters thereof wherein the esterifying group is selectively removed in the laboratory, or hydrolyzed under physiological conditions.

These compounds are useful either systemically or topically in the treatment of diseases caused by susceptible microorganisms, as animal feed additives for promotion of growth, or in the preservation of biodegradable materials, or as intermediates to compounds having such antibacterial activity.

Key to the synthesis of these compounds is the light catalyzed rearrangement of 2-diazo-1-oxoceph-3-em-4-carboxylates to 1-oxocarbapen-2-em-3-carboxylates, a newly discovered reaction determined to be of general applicability.

30 Claims, No Drawings

PHOTOCATALYZED PROCESS FOR PRODUCING CARBAPENAMS AND CARBAPEN-2-EMS

CROSS-REFERENCE TO RELATED APPLICATION

This application is a continuation-in-part of pending application Ser. No. 149,604, filed May 14, 1980, now abandoned.

BACKGROUND OF THE INVENTION

A number of carbapenams and carbapen-2-ems have been described in the literature—some of which have been reported to possess utility as antibacterial agents. Among the latter are a variety of fermentation derived products, the first of which was thienamycin:

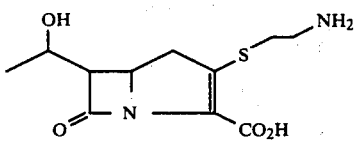

[Albers-Schonberg et al., J. Am. Chem. Soc. 100, 6491 (1978)]. Other compounds in this family of fermentation products include olivanic acids:

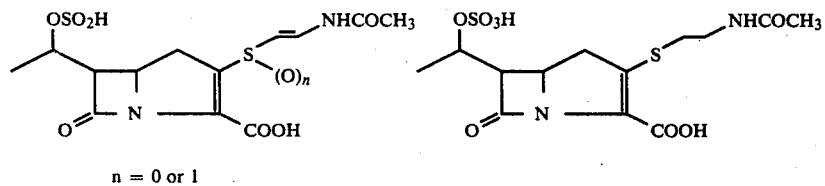

n = 0 or 1

[Brown et al., J. Chem. Soc. Chem. Commun., 523 (1977); Corbett et al., ibid. 953 (1977)], and a compound designated as PS-5:

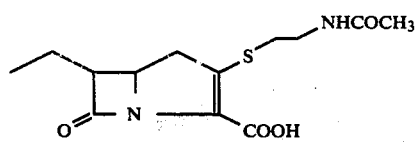

[Okamura et al., J. Antibiotics 31, 480 (1978)]. Subsequently a number of derivatives of thienamycin have been disclosed as having useful antibacterial activity, including the carbapen-2-em and carbapenam derivatives:

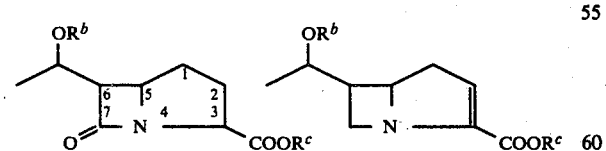

Belgian Pat. No. 867,227) wherein $R^b$ is broadly defined to include hydrogen, acetyl and benzyloxycarbonyl and $R^c$ is broadly defined to include hydrogen and conventional carboxy protecting groups, such as benzhydryl and 2-naphthylmethyl (selectively removed by hydrogenolysis), 2,2,2-trichloroethyl (selectively removed by mild zinc reduction) and various 1-alkoxycarbonyloxyalkyl groups (selectively hydrolyzed under physiological conditions).

Thienamycin has also been prepared by total synthesis [Johnston et al., J. Am. Chem. Soc. 100, 313 (1978)], as have an ester precursor [Kametani et al., Heterocycles 12 (9), 1189 (1979)] and a number of other carbapenams and carbapen-2-ems, including carbapenam itself [Wong et al., J. Am. Chem. Soc. 99, 2823 (1977); Busson and Vanderhaeghe, J. Org. Chem. 43, 4438 (1978)], p-nitrobenzyl and 2,3-dihydro-3-oxobenzo[c]furan-1-yl-6-carboxylates [Onoue et al., Tetrahedron Letters (40), 3867 (1979)], 3-methylcarbapenam [Aida et al., Tetrahedron Letters (52), 4993 (1979)], p-nitrobenzyl 2-methylcarbapen-2-em-3-carboxylate [Baxter et al., J. Chem. Soc. Chem. Commun., 236 (1979)], sodium carbapen-2-em-3-carboxylate and sodium 6-(1-hydroxyethyl)carbapen-2-em-3-carboxylate [Cama and Christensen, J. Am. Chem. Soc. 100, 8006 (1978)], benzyl 2-oxocarbapenam-3-carboxylate and 2-(4-methylphenylsulfonyloxy)carbapen-2-em-3-carboxylate [Ratcliffe et al., Tetrahedron Letters (21), 31 (1980)]. Also disclosed in the literature are carbaceph-3-ems such as 7-acylamino-2-alkylcarbaceph-3-em-4-carboxylic and 7-acylamino-2-acyloxycarbaceph-3-em-4-carboxylic acid esters which are hydrolyzed in vivo, i.e. under physiological conditions (Belgian Pat. No. 875,054). In no case are these compounds derived by rearrangement of conventional beta-lactam derivatives nor are any of these compounds substituted at the 1-position.

Most recently, preparation of compounds of the structure

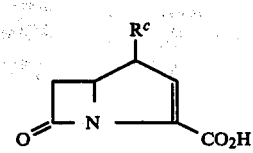

have been described (Christensen et al., U.S. Pat. No. 4,208,422). In these compounds $R^c$ is substituted or unsubstituted alkyl, aryl or aralkyl. The multistep syntheses of these compounds from an alpha, beta-unsaturated aldehyde, viz.,

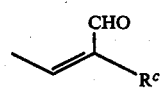

does not permit synthesis of the compounds of the present invention.

As a matter of simplicity, clarity and convenience, the nomenclature and ring number system generally employed herein is the standard "pen/ceph" nomenclature of the literature, e.g.

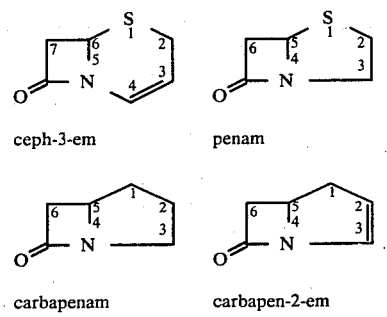

ceph-3-em   penam carbapenam   carbapen-2-em

An alternative name for carbapenam, also found in the literature, is 1-azabicyclo[3.2.0]heptan-7-one.

SUMMARY OF THE INVENTION

The present invention is concerned with variously substituted 1-oxo-, 1-hydroxy- and 1-acetoxycarbapenam and carbapen-2-em carboxylates of formulae:

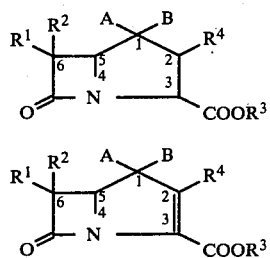

wherein:

$R^1$ is hydrogen; a conventional penicillin side chain; or

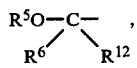

wherein $R^5$ is hydrogen, acetyl, or a conventional hydrogenolyzable acyl group, $R^6$ is hydrogen or $(C_1-C_5)$ alkyl and $R^{12}$ is hydrogen or methyl;

$R^2$ is hydrogen or methoxy; with the proviso that when $R^2$ is methoxy, $R^1$ is 2-phenoxyacetamido;

A and B, when taken together, are oxygen;

A and B, when taken separately, are respectively hydrogen and hydroxy or acetoxy;

$R^3$ is hydrogen or a conventional carboxy protecting group; and $R^4$ is methyl, acetoxymethyl, methanesulfonyloxy, OR and SR wherein R is $(C_1-C_3)$alkyl, 2-amidinoethyl, 2-acetamidoethyl or 2-aminoethyl, or 2-aminoethyl substituted with a conventional hydrogenolyzable acyl group; with the proviso that when $R^4$ is other than methyl, the compound is of the formula (II);

pharmaceutically-acceptable acid addition salts thereof when the compound has an amino or amidino function; and the pharmaceutically-acceptable cationic salts thereof when the compound has a carboxylic acid function.

The expression "conventional, hydrogenolyzable acyl group" is intended to encompass benzyloxycarbonyl (carbobenzoxy), p-nitrobenzyloxycarbonyl (p-nitrocarbobenzoxy) and the like which are selectively removed by catalytic hydrogenolysis. When a zinc reduction is contemplated as a step in the synthetic sequence, the benzyloxycarbonyl group is preferred over the p-nitro variant so as to avoid complicating side reactions.

The expression "conventional penicillin side chain" is intended to encompass the broad variety of side chains at the 6-position of penicillins and at the 7-position of cephalosporins which have found utility in these series of compounds, including those wherein amino, hydroxy and carboxy groups, if any, are protected by groups which are selectively removed by hydrogenolysis. Particularly valuable side chains are 5-methyl-3-phenylisoxazole-4-carboxamido, and 2-mono- and 2,2-disubstituted acetamido exemplified by:

2-phenylacetamido;
2-thienylacetamido;
2-phenoxyacetamido;
D-2-amino-2-phenylacetamido;
D-2-amino-2-(4-hydroxyphenyl)acetamido;
D-2-(4-ethyl-2,3-dioxopiperazine-1-carboxamido)-2-phenylacetamido;
D-2-(4-ethyl-2,3-dioxopiperazine-1-carboxamido-2-(4-hydroxyphenyl)acetamido;
2-hydroxy-2-phenylacetamido;
2-carboxy-2-phenylacetamido;

and the corresponding side chains wherein hydroxy, amino and carboxy groups are protected by selectively hydrogenolyzable groups.

The expression "amino, hydroxy, and carboxy groups protected by hydrogenolyzable groups" is intended to encompass hydroxy and amino groups substituted by benzyloxycarbonyl and the like, and carboxy groups esterified by benzhydryl, benzyl, 2-naphthylmethyl, and the like. Such groups are selectively removed by hydrogenolysis to form the corresponding hydroxy, amino, or carboxy group.

The expression "conventional carboxy protecting groups" is intended to refer to groups commonly employed to protect the carboxy group in penicillins and cephalosporins, specifically including:

(1) Groups which are selectively hydrogenolyzed to yield the corresponding acid. Exemplary are the benzyl, p-nitrobenzyl, benzhydryl and 2-naphthylmethyl esters. Preferred among these are benzyl, benzhydryl and 2-naphthylmethyl, since they are hydrogenolyzed with ease, but, unlike p-nitrobenzyl, have no tendency to complicate the zinc reductions of this invention.

(2) Groups which are selectively removed by mild zinc reduction. Exemplary is the 2,2,2-trichloroethyl group [cf. Just and Grozinger, Synthesis, 457 (1976)].

(3) Groups which are selectively hydrolyzed under physiological conditions. Exemplary of such groups are acetoxymethyl, pivaloyloxymethyl, 1-ethoxycarbonyloxyethyl and 1,3-dihydro-3-oxobenzo[c]furan-1-yl. Such esters are prodrugs, and are particularly suited as more stable forms of the corresponding acid (released under physiological conditions), as well as improving oral absorption when a compound of the present invention finds oral use as a systemic antibacterial agent.

Also encompassed by the present invention are pharmaceutically-acceptable salts when the compounds contain a free carboxylic acid (e.g. $R^3$ is hydrogen) or a free amino or amidino group (e.g. R is 2-aminoethyl or 2-amidinoethyl).

The compounds of the present invention have antibacterial activity, or are intermediates to compounds having such activity. The antibacterial activity of these compounds is readily determined by the standard disc-plate assay described below in more detail. This method is routinely applied to check the susceptibility of microorganisms, including those freshly isolated in clinical practice. The measured antibacterial activity reflects use in the systemic or topical treatment of animal and human infections due to susceptible bacteria, in animal feeds as growth promotants, or in the preservation of substances biodegradable by susceptible bacteria.

Also encompassed by the present invention and the key to the preparation of the present compounds is the rearrangement of 2-diazo-1-oxoceph-3-em-4-carboxylates to 1-oxocarbapen-2-em-3-carboxylates. This rearrangement has broadly sweeping application to the synthesis of novel carbapen-2-ems and carbapenams.

DETAILED DESCRIPTION OF THE INVENTION

The compounds of the present invention are readily prepared. Key to their preparation is a newly discovered photolytically catalyzed rearrangement of a 2-diazo-1-oxoceph-3-em-4-carboxylate to a 1-oxocarbapen-2-em-3-carboxylate, viz.,

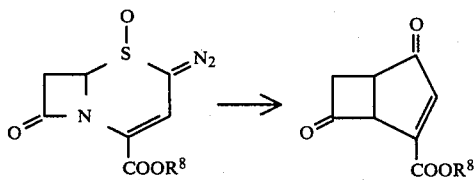

wherein $R^8$ is a conventional carboxy protecting group as defined hereinbefore. A large number of specific examples define the broad scope of this reaction. These specific examples are summarized by the following transformation:

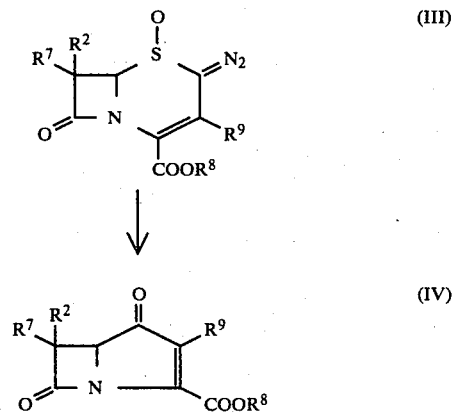

in which general formulae $R^2$ and $R^8$ are as hereinbefore defined;

$R^7$ is hydrogen;
2-phenoxyacetamido;
D-2-(4-ethyl-2,3-dioxopiperazine-1-carboxamido)-2-phenylacetamido;
D-2-benzyloxycarbonylamino-2-phenylacetamido;
a benzyhydryl, benzyl or 2-naphthylmethyl ester of 2-carboxy-2-phenylacetamido;
5-methyl-3-phenylisoxazole-4-carboxamido; or

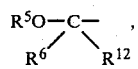

wherein $R^5$, $R^6$ and $R^{12}$ are as hereinbefore defined; and $R^9$ is methyl, acetoxymethyl, methanesulfonyloxy, $OR^{10}$ or $SR^{10}$ wherein $R^{10}$ is $(C_1-C_3)$alkyl, 2-acetamidoethyl, 2-benzyloxycarbonylaminoethyl or 2-(p-nitrobenzyloxycarbonylamino)ethyl.

This photolytic rearrangement is conveniently carried out in an organic solvent diluent in standard laboratory (pyrex) apparatus over a broad temperature range (e.g., $-100°$ C. to $35°$ C.), provided that the solvent is a liquid at the temperature employed.

Exemplary of the wide range of suitable organic solvents are chlorinated hydrocarbons (e.g. methylene chloride), lower alkanols (e.g. methanol) and aromatic hydrocarbons (e.g. toluene). Simple experimentation will determine the utility of other solvents (ethers, ketones, etc.). A preferred solvent is methylene chloride, it being low boiling and therefore readily removed by evaporation in vacuo during isolation. To minimize possible beta-lactam degradation, it is preferred to carry out the photolysis at lower temperatures (e.g in the range of $-45°$ to $-85°$ C.), conveniently in a dry ice-acetone bath (ca. $-78°$ C.). The light source is one having light of wavelength in the range of any standard sun lamp, i.e. ultraviolet into the visible. The course of the photolysis is readily followed by infrared spectroscopy (disappearance of the characteristic diazo band) or by standard thin layer chromatography, with detection of components by alkaline permanganate spray; eluants are selected so as to separate starting material and product; in the present case methylene chloride or chloroform, with varying portions of ethyl acetate, are frequently well-suited. Use of standard light-filters will readily determine optimal wavelengths for this photolysis reaction. The by-products of the reaction are nitrogen gas and sulfur. When carbapen-2-em-3-carboxylate (IV) of greater purity is desired, the reaction mixture is conveniently stirred with Raney nickel to remove sulfur. Since Raney nickel tends also to absorb some product and thus reduce yields, this step in the isolation is preferably omitted when the 1-oxocarbapen-2-em-3-carboxylate is further processed by a procedure other than hydrogenolysis. The 1-oxocarbapen-2-em-3-carboxylates, in comparison to the other compounds of the present invention, are relatively unstable compounds. Temperatures are therefore minimized during this isolation (e.g. $<25°$ C., preferably $<5°$ C.), and they are usually prepared shortly before use, or stored at freezer temperatures.

The further transformations of carbapen-2-em-3-carboxylates, typical of those employed to prepare the other compounds of the present invention, are summarized in Schemes I and II.

Scheme I
Transformations of Carbapen-2-em-3-carboxylates

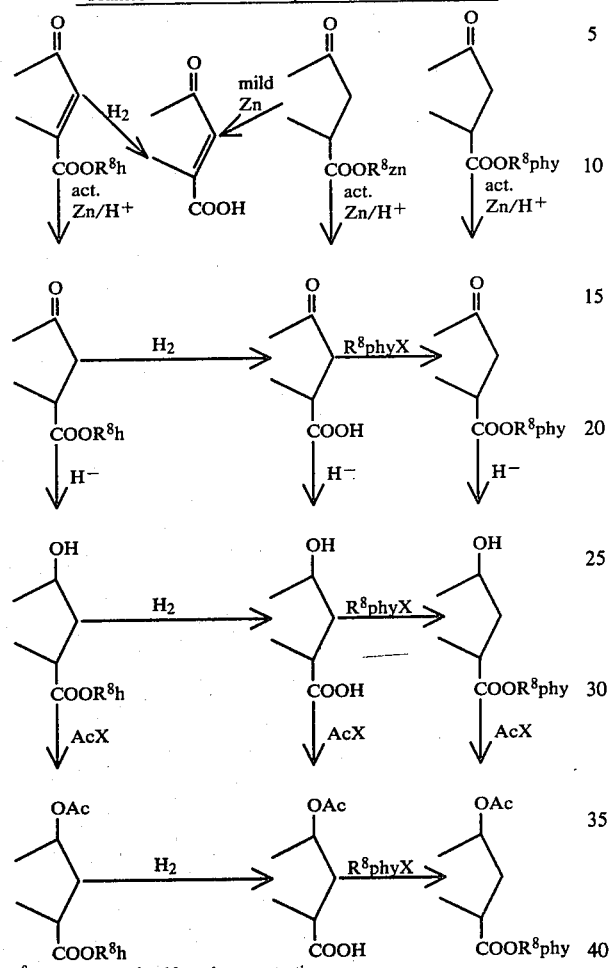

$R^8h$ = hydrogenolyzable carboxy protecting group.
$R^8zn$ = mild zinc reducible carboxy protecting group.
$R^8phy$ = physiologically hydrolyzable carboxy protecting group.
X = a leaving group.

Scheme II
Further Transformations of Carbapen-2-em-3-carboxylates

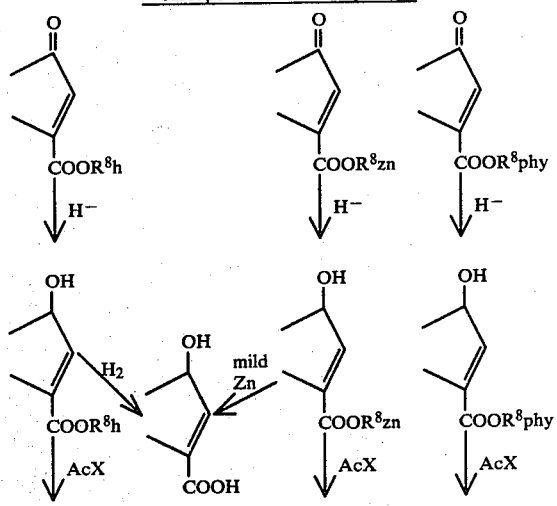

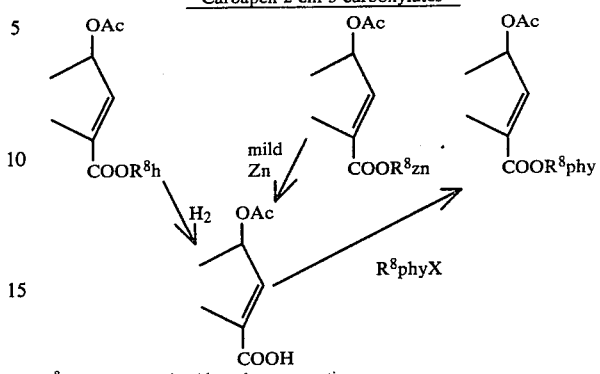

$R^8h$ = hydrogenolyzable carboxy protecting group.
$R^8zn$ = mild zinc reducible carboxy protecting group.
$R^8phy$ = physiologically hydrolyzable carboxy protecting group.
X = a leaving group.

The hydrogenolysis reactions of Schemes I and II, wherein a hydrogenolyzable carboxy protecting group ($R^8h$) is removed by hydrogenolysis, are carried out by methods well-known in the art, viz., hydrogenation over an appropriate catalyst, such as palladium, platinum, or rhodium, optionally on a carrier such as carbon, calcium carbonate, or alumina, in an inert solvent, in such manner that degradation of the carbapenam or carbapenem is minimized. Thus conditions are preferably near-neutral at ambient temperature or lower, and conveniently, at low pressure (e.g. 1 to 7 atmospheres). By "inert solvent" is meant one which will finitely solubilize the starting material, without significantly reacting with starting material(s), product(s) or reagent(s) (in this case hydrogen and catalyst). The preferred solvents for the hydrogenolysis are also those which are volatile and in which product is also soluble, so that product can be recovered by simple evaporation in vacuo (or freeze drying, as appropriate) of the filtrate after recovery of catalyst. The preferred catalysts for hydrogenolyses are palladium on carbon or palladium on calcium carbonate. Compounds of the present invention which contain hydrogenolyzable groups attached to a C-2 or C-6 side chain amino, hydroxy or carboxy (e.g. benzyloxycarbonyl, p-nitrobenzyloxycarbonyl or benzhydryl), are likewise hydrogenolyzed (i.e., to amino, hydroxy or carboxy groups). When hydrogenolysis is one of multiple steps to a compound of this invention, and optional routes are available, it is preferred to carry out the hydrogenolysis on a carbapenam, as opposed to a carbapen-2-em, since the former are more stable and readily handled under the conditions of hydrogenolysis. Analogously, hydrogenolysis of a 1-acetoxycarbapen-2-em is preferred over hydrogenolysis of a 1-oxo- or 1-hydroxycarbapen-2-em, and hydrogenolysis of 1-acetoxy- or 1-hydroxycarbapenams is preferred over hydrogenolysis of 1-oxocarbapenams. Optimal conditions (e.g. time, level of catalyst, batch of catalyst) for the hydrogenolysis of any given compound of the present invention are readily determined by monitoring with thin-layer chromatography, using methods as described above.

The mild zinc reductions of Schemes I and II, wherein a protecting group ($R^8zn$), such as 2,2,2-trichloroethyl, is removed, are generally carried out following the method of Just and Grozinger [Synthesis (7), 457 (1976)], viz., reduction by a slurry of commercial zinc powder in a mixture of aqueous buffer (pH 4.2–7.2) and an inert, water-miscible, organic solvent such as tetrahydrofuran, preferably at ambient temperature or lower. When mild zinc reduction is one of multiple steps to a compound of this invention, and optional routes are available, it is preferable to carry out the mild zinc reduction on a carbapenam rather than a carbapenem. Analogously, it is preferable to carry out the mild zinc reduction on a 1-acetoxycarbapen-2-em rather than a 1-oxo or 1-hydroxycarbapen-2-em. The mild zinc reductions are also conveniently monitored by thin-layer chromatography, as detailed above.

The reduction of 1-oxocarbapen-2-ems to 1-oxocarbapenam-3-carboxylates (when the carboxy protecting group is $R^8h$ or $R^8phy$) or 1-oxocarbapenam-3-carboxylic acids (when the carboxy protecting groups if $R^8zn$) by zinc/acid couple are summarized in Scheme I. In order to carry out this reduction cleanly, under mild conditions of temperature and time, it is important to use specially activated zinc. Particularly well-suited is the highly active zinc prepared as a black powder by the procedure of Rieke and Uhm [Synthesis (7), 452 (1975)], viz., reduction of an anhydrous zinc salt with potassium in refluxing tetrahydrofuran under an inert atmosphere. The preferred acid for these activated zinc reductions is acetic acid. It is of sufficient acid strength to facilitate the reaction, and yet not so strong as to cause undue harm to the beta-lactam. Acetic acid is also simultaneously employed as solvent. While temperatures as high as 35° C. can be used for this reaction, temperatures of −10° to 0° C. are preferred. Since acetic acid freezes at about 17° C., it is necessary to add an inert diluent to function as an antifreeze. Tetrahydrofuran (30%) is well-suited for this purpose. The activated zinc reductions of the present invention are conveniently monitored and optimized by use of thin-layer chromatography, according to methods described above. With respect to the activated zinc reduction of the 1-oxocarbapen-2-ems of structure IV, this reaction has been usefully applied only in instances where $R^4/R^9$ is methyl.

The hydride reductions summarized in Schemes I and II (conversion of 1-oxocarbapenams to 1-hydroxycarbapenams and 1-oxocarbapen-2-ems to 1-hydroxycarbapen-2-(ems) are carried out by use of selective hydride reducing agents [i.e. those which will not tend to attack the ester group, the beta-lactam or amide side chain, if present, or, in the case of 1-oxocarbapen-2-ems, tend to reduce the double-bond (1,4-addition of hydride) rather than the carbonyl]. Since low temperatures and aprotic solvents are preferred for the reduction of these relatively reactive beta-lactams, tetraalkylammonium borohydrides in an inert, volatile solvent of low freezing point, such as methylene chloride, are particularly well-suited for these hydride reductions. Methylene chloride, or the like, as solvent also permits facile infrared spectroscopic monitoring of hydride reductions (disappearance of the characteristic carbonyl band), in addition to thin-layer chromatography. These tools can be used jointly with particular effectiveness to optimize the various hydride reductions of the present invention.

The acetylations of 1-hydroxycarbapenams and 1-hydroxycarbapen-2-ems, as summarized in Schemes I and II, are carried out by standard methods, conveniently employing acetic anhydride or acetyl chloride (AcX) in the presence of sufficient base (usually a tertiary amine such as pyridine or triethylamine) in an amount equivalent to any carboxy groups in the substrate as well as the co-produced acetic acid or hydrogen chloride. The reaction is generally carried out in an inert solvent (as defined above), preferably with additional catalyst (e.g. 10 mole % of p-dimethylaminopyridine). The temperature can be over a wide range (e.g. −100° C.–35° C.), but is preferably carried out at a low temperature in a volatile solvent. Methylene chloride is particularly well-suited for this purpose. It is a good solvent for starting materials and reagents, it has a low freezing point (−95° C.), so that reactions are conveniently carried out in a dry ice-acetone bath (ca. −78° C.), and products are readily isolated by evaporation of the solvent in vacuo. Use of methylene chloride also permits particularly facile monitoring of this reaction by infrared spectroscopy (appearance of the characteristic ester carbonyl band), in addition to the thin-layer chromatographic methods described above. The combination of these analytical techniques is particularly well adapted to optimization of the acetylation reactions. When the 1-hydroxycarbapenam or 1-hydroxycarbapen-2-em to be acetylated contains free amino or hydroxy group(s) in a side chain, such groups are also acetylated under the same conditions (in fact preferentially when the side chain is an amine or a primary alcohol as the hydroxymethyl group). When it is also desired to acetylate such side chain group(s), additional equivalents of reagents, as appropriate, are employed. When the free amino or hydroxy group(s) are desired, on side chain(s), it is preferable to acetylate the appropriate side chain benzyloxycarbonylated derivative, with removal of the protecting group(s) by hydrogenolysis as the final stage.

Conversion of the 3-carboxylic acids to the corresponding protected carboxylic acids (i.e. $R^8$ esters as defined above) is also accomplished by standard methods. The carboxylic acid, as the carboxylate salt (preformed or formed in situ by the addition of at least an equivalent of base), in a standard bimolecular displacement, is reacted with the appropriate halide, mesylate, etc. ($R^8phyX$), e.g. chloromethyl pivalate, bromomethyl acetate, 1-ethoxycarbonyloxyethyl chloride, 1,3-dihydro-3-oxobenzo[c]furan-1-yl bromide, benzyl chloride, benzyl bromide, benzyl mesylate, 2-bromomethylnaphthalene, benzhydryl chloride, etc. The base can be in the form of a tertiary amine or bicarbonate, and can be used in excess in order to maximize the concentration of carboxylate ion, and so increase rate. Sodium iodide can be added also as a catalyst. The reaction is carried out in an inert solvent (as defined above), polar, aprotic solvents such as dimethylformamide being preferred, since rapid reaction rates are obtained without any tendency to attack the beta-lactam of either substrate or product. Temperature range for the reaction is not critical (e.g. 0°–50° C.), but is preferably kept at ambient temperature or lower, to minimize degradation of the beta-lactam. These esterification reactions are monitored and optimized employing thin-layer chromatography as described above. In order to minimize degradation of the beta-lactams of this invention during these esterification reactions, minimum reaction times are desirable. For this reason, iodides are preferred over bromides, which in turn are preferred over chlorides, for use as reagents. When bromides or chlorides are used, iodide catalysis is usually beneficial. When the synthesis of a particular compound of this invention requires the formation of an ester of the type and the synthetic sequence permits optional routes, it is preferred to introduce the ester group prior to the rearrangement step.

The esters of this invention are also prepared by reaction of an appropriate diazo compound with the carboxylic acid. An inert, aprotic solvent is employed. Particularly well-suited is methylene chloride, since it is highly volatile and products are readily recovered by concentration in vacuo. Temperature is not critical (e.g. −25° to 35° C.), ambient temperature or lower being preferred. Exemplary of this type of ester formation is the reaction of diphenyldiazomethane with a carboxylic acid of this invention in methylene chloride to form the corresponding benzyhydryl esters. This reaction can also be monitored and optimized by use of thin-layer chromatography and infrared spectroscopy. Whenever the appropriate diazo compound is available, this preparation is preferred over the displacement reaction of the paragraph immediately above, because of the milder conditions generally required.

A third method for the synthesis of the esters of this invention is by dehydrative coupling of the appropriate alcohol (2,2,2-trichloroethanol, benzhydrol, benzyl alcohol, 2-hydroxymethylnaphthol, etc.) with approximately one equivalent of a carboxylic acid of the present invention. The dehydrative coupling is accomplished by means of a wide variety of agents commonly used in peptide synthesis. Representative agents include N,N-carbonyldiimidazole, N,N'-carbonyl-di-s-triazine, ethoxyacetylene, 1,1-dichlorodiethyl ether, diphenylketene p-tolylimine, N-hydroxyphthalimide, N-hydroxysuccinimide, N-hydroxypiperidine, ethylene chlorophosphite, diethylethylenepyrophosphite, N-ethyl-5-phenylisoxazolium-3'-sulfonate, phenylphosphoro-di-(1-imidazolate) and carbodiimides such as dicyclohexylcarbodimide, 1-cyclohexyl-3-(2-morpholinomethyl)carbodiimide, N-(3-dimethylaminopropyl)-N'-ethylcarbodiimide hydrochloride, 1-ethyl-3-(3'-dimethylaminopropyl)carbodiimide hydrochloride and diethyl cyanamide. Generally between 1 and 1.2 equivalents of the dehydrative agent is used in the presence of a tert-amino catalyst (e.g. pyridine, triethylamine; usually between 1 and 1.5 equivalents). An inert, aprotic solvent is employed. Temperature is not critical (e.g. −25° to 40° C.), preferably ambient temperature or lower. Methylene chloride as solvent and room temperature are convenient conditions. Hydrated reagent is removed by filtration and products recovered by simple concentration in vacuo. Reactions are monitored by thin-layer chromatography and infrared spectroscopy. Where appropriate alcohols are available, this esterification procedure is preferred over the halide displacement procedure described above, because of the milder conditions.

It is evident that under the various esterification conditions described above, side chain carboxy groups will also tend to be esterified. If a free carboxy group in the side chain is desired, it is preferably blocked by a protecting group (e.g. benzyl, benzhydryl, 2-naphthylmethyl removable by selective hydrogenolysis if a pivaloyoxymethyl or 2,2,2-trichloroethyl ester at C-3 is desired), avoiding chromatographic separation of complex mixtures.

The amidines of the present invention are prepared from the corresponding amines by reaction of the latter with a lower alkylforamidate, (e.g. ethyl formamidate) at a slightly basic pH (e.g. 8.5–10.5) in a reaction inert aqueous or organic solvent at 0°–50° C. Aqueous phosphate buffer, (pH about 9.5) in dimethylformamide at ambient temperature are exemplary conditions for this reaction.

Certain compounds of this invention are alternatively prepared from mesylates, e.g.,

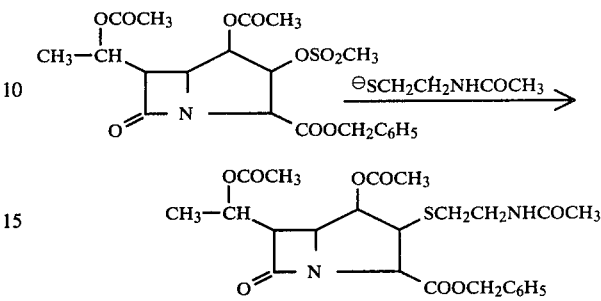

The reaction is carried out in a basic two phase system (e.g. 0.02 N sodium hydroxide/methylene chloride) in the presence of substantially a molar equivalent of a lipophilic quaternary salt (e.g. benzyltrimethylammonium chloride).

From the discussion above, it will be evident to those skilled in the art that more than one route is available for most of the compounds of the present invention, and that more optimal routes can generally be recognized in advance. For example if one wishes to prepare pivaloyloxymethyl 1-acetoxy-6-[2-amino-2-(4-hydroxyphenyl)acetamido]-2-methylcarbapenam-3-carboxylate, the most direct route, involving necessary esterification, acetylation and hydrogenolysis at preferred stages, would be to rearrange pivaloyloxymethyl-7-[2-benzyloxycarbonylamino-2-(4-benzyloxycarbonyloxyphenyl)acetamido]-2-diazo-3-methyl-1-oxoceph-3-em-4-carboxylate, followed in sequence by activated zinc reduction, hydride reduction, acetylation and hydrogenolysis; if one wishes to prepare 1-acetoxy-6-[2-carboxy-(4-hydroxyphenyl)acetamido]-2-methylcarbapen-2-em-3-carboxylate a typical, most direct route involving esterification, acetylation and hydrogenolysis at preferred stages would be rearrangement of benzhydryl 7-[2-benzhydryloxycarbonyl-2-(4-benzyloxycarbonyloxyphenyl)acetamido]-2-diazo-3-methyl-1-oxoceph-3-em-4-carboxylate, followed in sequence by hydride reduction, acetylation and hydrogenolysis; if one wishes to prepare 6-(1-acetoxyethyl)-1-oxo-2-methylcarbapenam-3-carboxylic acid, the most direct route is to rearrange 2,2,2-trichloroethyl-7-(1-acetoxyethyl)-2-diazo-3-methyl-1-oxoceph-3-em-4-carboxylate, followed by activated zinc reduction; and so forth.

The starting 2-diazo-1-oxoceph-3-em-4-carboxylates required as starting materials for the present syntheses are prepared by literature methods, or by Preparation methods detailed hereinafter. The final stage in the synthesis of the starting material is usually insertion of the 2-diazo group. The 2-diazo-1-beta-oxoceph-3-ems are prepared according to the method of Ebbinghaus et al. [J. Org. Chem. 44 (25), 4697 (1979)], alternatively, in the further presence of potassium tert-butoxide, as detailed in Preparations hereinafter. The latter method, but generally employing somewhat more vigorous conditions of time and temperature, is also well suited for the synthesis of the corresponding 2-diazo-1-alpha-oxoceph-3-ems. The requisite 1-oxoceph-3-em-4-carboxylates are extensively available in the literature (cf. Bruyns and Koning, U.S. Pat. No. 4,182,870). The required oxides are readily prepared by peracid (conveniently m-chloroperbenzoic acid) or 30% hydrogen peroxide/formic acid oxidation, as the penultimate step or at another suitable precursor stage. In some cases, separable mixtures of 1-alpha and 1-beta-oxides result; in others, clean 1-beta-oxides result. In either case, the oxide is suitable for the further processing of this invention. The requisite carboxy and amino, and if desired, hydroxy protecting groups are introduced at a suitable stage in the synthesis of the starting material, using methods detailed above. Since the beta-lactams of these precursors are generally more stable than those of the compounds of the present invention, there is generally less distinct preference concerning the particular method chosen for esterification. Acetylations of appropriate precursors are carried out in the manner described above for acetylation of compounds of the present invention. Benzyloxycarbonylation of appropriate precursors are carried out by the same process as acetylation, substituting an equivalent of carbobenzoxy chloride for the acetylating agent. Amino groups can be selectively acylated over hydroxy groups by using a single molar equivalent of the acylating agent.

The pharmaceutically-acceptable cationic salts of those compounds of the present invention having a free carboxylic acid group are readily prepared by standard methods. For example, an equivalent of the corresponding cationic hydroxide, carbonate or bicarbonate is combined with the carboxylic acid in an organic or aqueous solvent. The salt is isolated by concentration and/or the addition of a non-solvent. In some cases, the salt is isolated directly from a reaction mixture, without isolation of the free acid form. Pharmaceutically-acceptable cationic salts include, but are not limited to, those formed with sodium, potassium, calcium, N,N'-dibenzylethylenediamine, N-methylglucamine and diethanolamine.

The pharmaceutically-acceptable acid addition salts of those compounds of the present invention having a free amino or amidino group are also readily prepared by standard methods. For example, an equivalent of the acid is combined with amine or amidine in an organic or aqueous organic solvent. The salt is isolated by concentration and/or the addition of a non-solvent. In some cases, the salt is isolated directly from a reaction mixture, without isolation of the free amine or amidine. Pharmaceutically-acceptable acid addition salts include, but are not limited to, hydrochloric acid, sulfuric acid, nitric acid, phosphoric acid, citric acid, maleic acid, succinic acid and methanesulfonic acid.

The utility of the various compounds as intermediates to other compounds of the present invention will be evident from the preceding discussion. The antibacterial activity of these compounds, reflecting their utility in the control of susceptible bacterial infections in man and animals, as animal feed additives for promotion of growth, or as preservatives of materials biodegraded by susceptible microorganisms, is best measured by the standard disc-plate method routinely employed in clinical laboratories for determining the sensitivity of microorganisms to antimicrobial substances. Sensitivity discs are prepared by dipping a standard 6.25 mm. paper disc into a solution of the compound to be tested (conc. 1 mg./ml.) in a volatile solvent (e.g. methylene chloride) and the disc dried, producing discs containing approximately 25 microg. of the compound. The discs are placed on the surface of agar growth media seeded with the test microorganism, previously plated into Petri dishes. The plates are incubated overnight at 35°–37° C. Activity of the test compound is reflected by a zone of inhibition of bacterial growth around the test disc. The diameter of this zone provides a quantitative measure of the activity of the antibacterial substance. The activity of various compounds of the present invention is summarized in Table I. For comparison, results obtained with 10 microg. discs of ampicillin and penicillin G are included as positive controls. The alternative in vitro screening procedure involving growth of the microorganisms in tubes containing serially diluted concentrations of test compound in brain heart infusion broth does not correctly reflect the antibacterial activity of the compounds of this invention, a result of the instability of these compounds in the test media. For example, a 25 microg. disc of pivaloyloxymethyl 2-methyl-1-oxocarbapenam-3-carboxylate tested against *Staphylococcus aureus* in the disc-plate assay shows that this compound has good activity against this particular microorganism, in spite of the fact that the same compound against the same microorganism indicated a minimum inhibitory concentration of >200 microg./ml. in the serial dilution tube test. The results of the serial dilution tube testing of compounds of the present invention are summarized in Table II.

TABLE I

Antibacterial Activity of
Carbapenams and Carbapen-2-ems
Disc-Plate Method

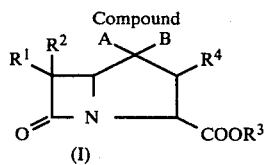

(I)

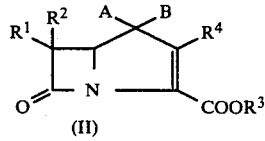

(II)

| R¹ | R² | R³ | R⁴ | A B | I/II | Vibrio percolans | Escherichia coli | Staphylococcus aureus (Antibiotic Resistant) | Micrococcus luteus | Bacillus subtilis | Staphylococcus aureus 5 |
|---|---|---|---|---|---|---|---|---|---|---|---|
| H | H | POM | CH₃ | —O— | I | — | — | 0 | — | 18 | 18 |

Zone of Inhibition (mm)

TABLE I-continued

Antibacterial Activity of
Carbapenams and Carbapen-2-ems
Disc-Plate Method

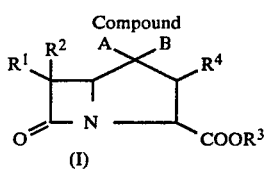
(I)

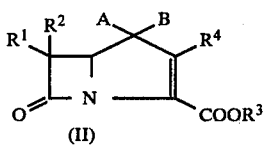
(II)

| $R^1$ | $R^2$ | $R^3$ | $R^4$ | A | B | I/II | Vibrio percolans | Escherichia coli | Staphylococcus aureus (Antibiotic Resistant) | Micrococcus luteus | Bacillus subtilis | Staphylococcus aureus 5 |
|---|---|---|---|---|---|---|---|---|---|---|---|---|
| H | H | POM | $CH_3$ | H | OH | I | — | — | 0 | — | 0 | 0 |
| H | H | H | $CH_3$ | H | OAc | I | — | — | 0 | — | 12 | 0 |
| H | H | POM | $CH_3$ | —O— | | II | 14 | 0 | 18 | 26 | 37 | 22 |
| H | H | POM | $CH_3$ | H | OH | II | — | 10 | 13 | 10 | 15 | 15 |
| H | H | POM | $CH_3$ | H | OAc | II | — | — | 0 | 0 | 14 | 13 |
| H | H | H | $CH_3$ | H | OAc | II | 18 | 0 | 8 | — | 13 | — |
| H | H | POM | $CH_2$—OAc | —O— | | II | — | — | 12 | — | — | 0 |
| PMA | H | POM | $CH_3$ | —O— | | I | — | 0 | 12 | 15 | 21 | — |
| PMA | H | POM | $CH_3$ | H | OH | I | — | 0 | 17 | 14 | 23 | 20 |
| PMA | H | POM | $CH_3$ | H | OAc | I | — | 0 | 0 | 0 | 16 | 11 |
| PMA | H | H | $CH_3$ | H | OAc | I | — | 0 | 0 | 0 | 0 | 0 |
| PMA | OMe | POM | $CH_3$ | —O— | | I | 0 | 0 | 0 | — | 11 | 0 |
| PMA | OMe | POM | $CH_3$ | H | OH | I | 0 | 0 | 0 | — | 11 | 23 |
| PMA | OMe | POM | $CH_3$ | —O— | | II | 0 | 0 | 0 | — | 33 | 8 |
| MPI | H | POM | $CH_3$ | —O— | | I | 0 | 0 | 11 | — | 15 | 0 |
| MPI | H | POM | $CH_3$ | H | OH | I | 13 | 0 | 14 | — | 16 | 15 |
| MPI | H | POM | $CH_3$ | —O— | | II | 0 | 0 | 9 | — | 21 | 0 |
| EPA | H | POM | $CH_3$ | —O— | | I | 21 | 12 | 12 | — | 21 | 12 |
| EPA | H | POM | $CH_3$ | H | OH | I | 24 | 20 | 10 | — | 17 | 18 |
| EPA | H | H | $CH_3$ | H | OH | I | 25 | 16 | 9 | — | 16 | 15 |
| EPA | H | POM | $CH_3$ | —O— | | II | 20 | 0 | 0 | 0 | 0 | 0 |
| HET | H | H | $CH_3$ | H | OH | I | — | 23 | — | 39 | 29 | 29 |
| HET | H | H | $CH_3$ | H | OAc | I | — | 0 | — | 13 | 16 | 0 |
| HET | H | H | $OCH_3$ | H | OH | I | — | 11 | — | 42 | 22 | 27 |
| HET | H | POM | $CH_3$ | H | OH | I | — | 14 | — | 31 | 24 | 27 |
| AET | H | H | $CH_3$ | H | OH | I | 16 | 0 | — | 20 | 15 | 20 |
| AET | H | H | $CH_3$ | H | OAc | I | 10 | 0 | — | 26 | 25 | 21 |
| Positive controls[a]: | | | | | | | | | | | | |
| Penicillin | | | | | | | 33 | 16 | 0 | 45 | 32 | 31 |
| Penicillin G | | | | | | | 32 | 0 | 0 | 45 | 33 | 32 |

POM = pivaloyloxymethyl
PMA = 2-phenoxyacetamido
MPI = 5-methyl-3-phenylisoxazolecarboxamido
EPA = D-2-(4-ethyl-2,3-dioxopiperazine-1-carboxamido)-2-phenylacetamido
HET = 1-hydroxyethyl
AET = 1-acetoxyethyl
[a]10 microgram discs; all others 25 microgram discs.

TABLE II

Antibacterial Activity of Carbapenams and Carbapen-2-ems
Serial Dilution-Tube Method Compound

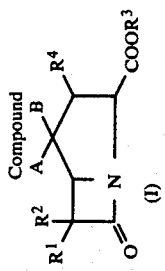
(I)

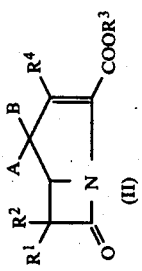
(II)

| R¹ | R² | R³ | R⁴ | A | B | I/II | Proteus morgani | Citrobacter diversus | Enterobacter cloacae | Serratia marcescens | Klebsiella pneumoniae | Pseudomonas aeruginosa | Escherichia coli (Antibiotic Resistant) | Escherichia coli | Staphylococcus aureus (Antibiotic Resistant) | Staphylococcus aureus |
|---|---|---|---|---|---|---|---|---|---|---|---|---|---|---|---|---|
| H | H | POM | $CH_3$ | —O— | | I | >200 | >200 | >200 | >200 | >200 | >200 | >200[b] | >200 | >200[a] | >200 |
| H | H | POM | $CH_3$ | H | OH | I | >200 | >200 | >200 | >200 | >200 | >200 | >200 | >200 | >200 | >200 |
| H | H | H | $CH_3$ | H | OAc | I | >200 | >200 | >200 | >200 | >200 | >200 | >200 | >200 | >2000 | >200 |
| H | H | POM | $CH_3$ | —O— | | II | >200 | >200 | >200 | >200 | >200 | >200 | >200 | >200 | >200 | >200 |
| PMA | H | POM | $CH_3$ | —O— | | I | >200 | >200 | >200 | >200 | >200 | >200 | >200 | >200 | >200 | >200 |
| PMA | H | POM | $CH_3$ | H | OH | I | >200 | >200 | >200 | >200 | >200 | >200 | >200 | >200 | 200[a] | 25 |
| PMA | H | POM | $CH_3$ | H | OAc | I | >200 | >200 | >200 | >200 | >200 | >200 | >200 | >200 | >200 | >200 |
| PMA | OMe | POM | $CH_3$ | —O— | | I | >200 | >200 | >200 | >200 | >200 | >200 | >200 | >200 | >200[a] | >200 |
| PMA | OMe | POM | $CH_3$ | H | OH | I | >200 | >200 | >200 | >200 | >200 | >200 | >200 | >200 | >200 | >200 |
| MPI | H | POM | $CH_3$ | H | OH | I | 25 | 100 | 200 | 100 | 100 | >200 | >200 | >200 | 100 | 100 |
| EPA | H | POM | $CH_3$ | —O— | | I | 0.39 | 12.5 | 12.5 | 25 | 12.5 | >200 | >200 | 100[a] | >200 | 25 |
| EPA | H | POM | $CH_3$ | H | OH | I | ≦0.39 | 12.5 | 12.5 | 25 | 12.5 | 200 | >200 | 6.25 | >200 | 25 |
| EPA | H | H | $CH_3$ | H | OH | I | 50 | >200 | 50 | >200 | >200 | 200 | >200 | 100 | 200 | 50 |
| HET | H | H | $CH_3$ | H | OH | I | 25 | — | 25 | 50 | 50 | >200 | 12.5 | 6.25 | 3.12 | 1.56 |
| HET | H | H | $CH_3$ | H | OAc | I | >200 | — | >200 | >200 | >200 | >200 | >200 | >200 | 100 | 100 |

POM = pivaloyloxymethyl. PMA = 2-phenoxyacetamido. MPI = 5-methyl-3-phenylisoxazole-1-carboxamido. EPA = D-2-(4-ethyl-2,3-dioxo-piperazine-1-carboxamido)-2-phenylacetamido.
HET = 1-hydroxyethyl.
[a]Shows a synergistic effect when tested 1:1 with ampicillin.
[b]Shows a synergistic effect when tested 1:1 with cefazolin.

Those antibacterial compounds of the present invention which are useful for the treatment of systemic infections in animals, including man, caused by susceptible microorganisms, are dosed at a level of 5–250 mg./kg. per day, preferably 10–150 mg./kg./day, usually in divided doses. Variation in dosage will be made depending upon the individual and upon the susceptibility of the microorganism. These compounds are most effective when dosed parenterally, preferably intramuscularly as a suspension of a more stable pro-drug ester form (as defined above). The susceptibility of microorganisms isolated in the clinics is routinely tested in clinical laboratories by the disc-plate method described above. Preferred compounds are those which show the largest diameter zone of inhibition against the bacteria causing the infection to be treated.

The parenteral dosage forms required for the above systemic use are preferably made up in finely divided, dry powder form, dissolved or suspended immediately before use in a pharmaceutically-acceptable carrier such as water, saline, sesame oil and the like. Agents which improve the suspendability and dispersion qualities can also be added. Preparation of optimal dosage forms will be by methods well known to the pharmacist's art.

Those antibacterial compounds of the present invention which are useful in the treatment of topical infections in animals, including man, caused by susceptible microorganisms are provided as lotions, ointments, creams, salves, gels, or the like at concentrations in the range 5–200 mg./cc. of the dosage form, preferably in the range 10–100 mg./cc. The dosage form is applied at the site of infection ad libitum, generally at least once per day. Microorganisms which are the cause of infections are routinely isolated in clinical laboratories, and the susceptibility of these microorganisms to the compounds of this invention is routinely determined in the same laboratories by the disc-plate method described above. Preferred compounds are those which show the largest zone of inhibition of the bacteria causing the infection to be treated.

Preferred topical dosage forms are finely divided suspensions of a pro-drug ester, in an inert, pharmaceutically-acceptable carrier. Preparation of optimal dosage forms will be by methods well-known in the pharmaceutical art.

When the antibacterial compounds of the present invention are useful as growth promotants in domestic food animals, they are provided at low levels (e.g. 10 g. to 100 g. of compound per ton of feed). Blending of the compound with feed is usually accomplished in two stages, first in the preparation of a preblend (e.g. 10–100 g. of compound blended with 10–20 lb. of soybean mill run or the like), which is then blended with the feed at the time of milling. Since growth promotion is effected by a low level of activity, and at the same time the compound is exposed to conditions out of the control of the scientist, the compounds of this invention which are preferred for this use are those of better stability, viz., in order of preference, 1-acetoxycarbapenam-3-carboxylate esters, 1-hydroxy-carbapenam-3-carboxylate esters and 1-acetoxycarbapen-2-em-3-carboxylate esters.

Those antibacterial compounds of the present invention which are useful as preservatives of biodegradable materials, are simply blended with the biodegradable material at a concentration which is at least sufficient to inhibit the growth of the basteria causing biodegradation. Routine serial dilution techniques can be used to determine the concentrations necessary to achieve the desired purpose.

The present invention is illustrated by the following examples. However, it should be understood that the invention is not limited to the specific details of these examples.

EXAMPLE 1

Pivaloyloxymethyl
2-Methyl-1-oxocarbapen-2-em-3-carboxylate

In a standard pyrex flask, pivaloyloxymethyl 2-diazo-3-methyl-1-beta-oxoceph-3-em-4-carboxylate (124 mg., 0.35 mmoles) was dissolved in 124 ml. of methylene chloride, cooled to $-78°$ C. and irradiated with a sun lamp for a total of 25 minutes, while monitoring the reaction to completion by ir spectral analyses. The reaction was stripped to dryness in vacuo, yielding crude pivaloyloxymethyl 1-oxo-2-methylcarbapen-2-em-3-carboxylate [ir ($CH_2Cl_2$): 1815, 1750, 1720 $cm^{-1}$].

Alternatively, upon completion of the reaction, the mixture is stirred with 1.24 g. of Raney nickel at $-78°$ C. for 30 minutes, filtered and the filtrate stripped in vacuo to yield the same product in a higher state of purity.

By the same methods pivaloyloxymethyl 2-diazo-3-methyl-1-alpha-oxoceph-3-em-4-carboxylate is converted to the same pivaloyloxymethyl 2-methyl-1-oxocarbapen-2-em-3-carboxylate.

By the same methods, the other diazo-alpha- and beta-oxides of Preparation 3 are converted to the corresponding acetoxymethyl, 1,3-dihydro-3-oxobenzo[c]furan-1-yl and 1-ethoxycarbonyloxyethyl-2-methyl-1-oxocarbapen-2-em-3-carboxylates.

EXAMPLE 2

Pivaloyloxymethyl
2-Methyl-1-oxocarbapenam-3-carboxylate

Method A

Pivaloyloxymethyl 2-methyl-1-oxocarbapen-2-em-3-carboxylate, freshly prepared from 50 mg. of pivaloyloxymethyl 1-beta-oxo-2-diazo-3-methylceph-3-em-4-carboxylate by the method of Example 1 (employing the alternative Raney nickel step), was taken up in approximately 0.25 ml. of tetrahydrofuran and added to a slurry of 500 mg. of zinc powder, specially activated by the method of Rieke and Uhm [Synthesis, 452 (1975)], in 15 ml. of acetic acid-30% tetrahydrofuran at 0° C. After stirring for 1 hour at this temperature, the reaction mixture was diluted with toluene, stripped in vacuo and the residue chased several times with toluene. The vacuum pumped residue was taken up in excess methylene chloride, the zinc removed by filtration, and the filtrate reevaporated in vacuo to yield essentially homogeneous pivaloyloxymethyl 2-methyl-1-oxocarbapenam-3-carboxylate (tlc: $R_f$0.45 with 18:1 chloroform:ethyl acetate as eluant; ir 1780, 1760 $cm^{-1}$).

By the same method the other carbapen-2-em esters of Example 1 are converted to the corresponding acetoxymethyl, 1,3-dihydro-3-oxobenzo[c]furan-1-yl and 1-ethoxycarbonyloxyethyl 2-methyl-1-oxocarbapenam-3-carboxylates.

Method B

By method B of Example 69 below, sodium 2-methyl-1-oxocarbapenam-3-carboxylate is converted to pivaloyloxymethyl 2-methyl-1-oxocarbapenam-3-carboxylate.

The same method, but substituting an equivalent amount of bromomethyl acetate, 1,3-dihydro-3-oxobenzo[c]furan-1-yl bromide or 1-ethoxycarbonyloxyethyl chloride, as appropriate, is used to produce acetoxymethyl, 1,3-dihydro-3-oxobenzo[c]furan-1-yl and 1-ethoxycarbonyloxyethyl 2-methyl-1-oxocarbapenam-3-carboxylates.

EXAMPLE 3

Pivaloyloxymethyl 1-Hydroxy-2-methylcarbapenam-3-carboxylate

Method A

Pivaloyloxymethyl 2-methyl-1-oxocarbapenam-3-carboxylate (70 mg., 0.23 mmole) was dissolved in 3 ml. of methylene chloride and cooled to −78° C. Tetrabutylammonium borohydride (15 mg., 0.06 mmole) was added and the reaction was stirred for 1 hour at −78° C., at which time, tlc (silica gel: 4:1 chloroform:ethyl acetate as eluant; detection by alkaline permanganate spray) indicated no starting material remained. Acetic acid (1 equivalent, 0.24 mmole) was added and the mixture then poured into water. The organic phase was separated, washed with additional portions of water and then brine, dried over anhydrous magnesium sulfate, filtered and evaporated to dryness. The resulting crude product was chromatographed on silica gel (4:1 methylene chloride:ethyl acetate eluant) to yield purified pivaloyloxymethyl 1-hydroxy-2-methylcarbapenam-3-carboxylate (tlc: $R_f$ 0.14 with 4:1 chloroform:ethyl acetate as eluant).

The same method is used to convert the other 1-oxopenam esters of Example 2 to the corresponding acetoxymethyl, 1,3-dihydro-3-oxobenzo[c]furan-1-yl and 1-ethoxycarbonyloxyethyl 1-hydroxy-2-methylcarbapenam-3-carboxylates.

Method B

By method B of Example 69, sodium 1-hydroxy-2-methylcarbapenam-3-carboxylate is converted to pivaloyloxymethyl 1-hydroxy-2-methylcarbapenam-3-carboxylate.

The same method, but substituting an equivalent amount of bromomethyl acetate, 1,3-dihydro-3-oxobenzo[c]furan-1-yl bromide or 1-ethoxycarbonyloxyethyl chloride, as appropriate, is used to prepare acetoxymethyl, 1,3-dihydro-3-oxobenzo[c]furan-1-yl and 1-ethoxycarbonyloxyethyl 1-hydroxy-2-methylcarbapenam-3-carboxylates.

Method C

By the method of Example 2, pivaloyloxymethyl 1-hydroxy-2-methylcarbapen-2-em-3-carboxylate is reduced with specially activated zinc powder in acetic acid-tetrahydrofuran, the reaction monitored by tlc (4:1 chloroform:ethyl acetate) and the product isolated to yield pivaloyloxymethyl 1-hydroxy-2-methylcarbapenam-3-carboxylate.

By the same method the other 1-hydroxycarbapen-2-em esters of Example 4 are converted to the corresponding acetoxymethyl, 1,3-dihydro-3-oxobenzo[c]furan-1-yl and 1-ethoxycarbonyloxyethyl 1-hydroxy-2-methylcarbapenam-3-carboxylates.

By the same method the 1-acetoxycarbapen-2-em esters of Example 5 are converted to the corresponding pivaloyloxymethyl, acetoxymethyl, 1,3-dihydro-3-oxobenzo[c]furan-1-yl and 1-ethoxycarbonyloxyethyl 1-hydroxy-2-methylcarbapenam-3-carboxylates.

EXAMPLE 4

Pivaloyloxymethyl 1-Hydroxy-2-methylcarbapen-2-em-3-carboxylate

Pivaloyloxymethyl 2-diazo-3-methyl-1-betaoxoceph-3-em-4-carboxylate (150 mg., 0.42 mmoles) was converted to a methylene chloride solution of pivaloyloxymethyl 2-methyl-1-oxocarbapen-2-em-3-carboxylate by the method of Example 1. Without isolation, and while continuing to maintain the temperature at −78° C., tetrabutylammonium borohydride (26.4 mg., 0.092 mmole) was added and the mixture stirred for 30 minutes. The reaction was quenched with acetic acid (0.58 equivalent), extracted twice with aqueous buffer (pH 7), dried over anhydrous sodium sulfate and filtered to yield a methylene chloride solution of pivaloyloxymethyl 1-hydroxy-2-methylcarbapen-2-em-3-carboxylate [ir (CH$_2$Cl$_2$) 1780, 1745 cm$^{-1}$; $R_f$ 0.25, (4:1 chloroform:ethyl acetate)]. If desired, this product is further isolated by evaporation in vacuo, keeping the temperature as low as possible to minimize degradation.

By the same methods, the other alpha and beta-oxides of Preparation 3 are converted to solutions of the corresponding 1-oxocarbapen-2-em esters, and then to the corresponding acetoxymethyl, 1,3-dihydro-3-oxobenzo[c]furan-1-yl and 1-hydroxy-2-methylcarbapen-2-em-3-carboxylates.

EXAMPLE 5

Pivaloyloxymethyl 1-Acetoxy-2-methylcarbapen-2-em-3-carboxylate

Method A

To the freshly prepared methylene chloride solution of pivaloyloxymethyl 1-hydroxy-2-methylcarbapen-2-em-3-carboxylate of Example 4, cooled to −78° C. was added acetic anhydride (0.170 ml., 1.68 mmoles), pyridine (0.144 ml., 1.68 mmoles) and 4-dimethylaminopyridine (10.5 mg., 0.086 mmoles) in two aliquots over 2 hours. The reaction was monitored by tlc (3:1 chloroform:ethyl acetate). After maintaining the reaction mixture at dry ice temperature for approximately 16 hours, additional 4-dimethylaminopyridine (0.5 mg.) was added and reaction continued for 2 hours at −78° C. The reaction mixture was extracted twice with aqueous buffer (pH 7), dried over anhydrous sodium sulfate, filtered and evaporated in vacuo. The residue was chromatographed on 8 g. of silica gel (6:1 chloroform:ethyl acetate as eluant, monitored by tlc or ir spectral analysis) to yield pivaloyloxymethyl 1-acetoxy-2-methylcarbapen-2-em-3-carboxylate [15 mg.; ir (CH$_2$Cl$_2$) 1780, 1740 cm$^{-1}$; $R_f$ 0.75 (3:1 chloroform:ethyl acetate)].

By the same method, the other 1-hydroxycarbapen-2-em esters of Example 4 are converted to the corresponding acetoxymethyl, 1,3-dihydro-3-oxobenzo[c]furan-1-yl and 1-ethoxycarbonyloxyethyl 1-acetoxy-2-methylcarbapen-2-em-3-carboxylates.

Method B

By the method of Preparation 1, 12, 15, 21, etc., 1-acetoxy-2-methylcarbapen-2-em-3-carboxylic acid is esterified to produce pivaloyloxymethyl 1-acetoxy-2-methylcarbapen-2-em-3-carboxylate.

By the same method, but substituting an equivalent quantity of bromomethyl acetate, 1,3-dihydro-3-oxobenzo[c]furan-1-yl bromide or 1-ethoxycarbonyloxyethyl chloride as appropriate, acetoxymethyl, 1,3-dihydro-3-oxobenzo[c]furan-1-yl and 1-ethoxycarbonyloxyethyl 1-acetoxy-2-methylcarbapen-2-em-3-carboxylates are prepared.

EXAMPLE 6

Benzhydryl 2-Methyl-1-oxocarbapen-2-em-3-carboxylate

By the procedure of Example 1 (30–50 minutes irradiation time, incorporating a 500 mg. Raney nickel treatment), benzhydryl 2-diazo-3-methyl-1-beta-oxoceph-3-em-4-carboxylate (50 mg.) in 50 ml. of methylene chloride was converted to benzhydryl 2-methyl-1-oxocarbapen-2-em-3-carboxylate [ir ($CH_2Cl_2$) 1810 cm$^{-1}$].

EXAMPLE 7

Benzhydryl 2-Methyl-1-oxocarbapenam-3-carboxylate

The freshly prepared benzhydryl 2-methyl-1-oxocarbapen-2-em-3-carboxylate of Example 6 was reduced by the detailed procedure of Example 2, to yield benzhydryl 2-methyl-1-oxocarbapenam-3-carboxylate [37 mg., 86%; $R_f$ 0.59 (18:1 chloroform:ethyl acetate); recrystallization from methylene chloride/hexane gave product of mp 132°–133° C.].

An X-ray crystallographic analysis indicated this product to have the following structure and relative stereochemistry:

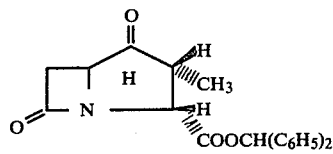

EXAMPLE 8

Benzhydryl 1-Hydroxy-2-methylcarbapenam-3-carboxylate

By the procedures of Example 3, benzhydryl 2-methyl-1-oxocarbapenam-3-carboxylate (53 mg. in 3 ml. of methylene chloride employing only the 10 mg. reducing agent initially charged) was converted to purified benzhydryl 1-hydroxy-2-methylcarbapenam-3-carboxylate [53 mg.; $R_f$ 0.30 (4:1 chloroform:ethyl acetate)].

EXAMPLE 9

Benzhydryl 1-Acetoxy-2-methylcarbapenam-3-carboxylate

Freshly prepared benzhydryl 1-hydroxy-2-methylcarbapenam-3-carboxylate (53 mg., 0.15 mmoles) was dissolved in 5 ml. of methylene chloride and cooled to −10° C. Pyridine (12 mg., 0.15 mmoles), acetic anhydride (15.4 mg., 0.15 mmoles) and 4-dimethylaminopyridine (18.4 mg., 0.15 mmoles) were added and the mixture stirred for 1 hour at −10° C., at which time tlc (4:1 chloroform:ethyl acetate) indicated clean conversion to the acetate ester. The reaction mixture was chromatographed on silicia gel (9:1 methylene chloride:ethyl acetate eluant), yielding purified benzhydryl 1-acetoxy-2-methylcarbapenam-3-carboxylate [$R_f$ 0.65 (4:1 chloroform:ethyl acetate)].

EXAMPLE 10

1-Acetoxy-2-methylcarbapenam-3-carboxylic Acid

Benzhydryl 1-acetoxy-2-methylcarbapenam-3-carboxylate (26 mg.) was dissolved in 3 ml. of ethyl acetate. Hydrogenation catalyst (10% palladium on carbon, 26 mg.) was added and the reaction mixture hydrogenated at room temperature and atmospheric pressure for 1 hour, at which time tlc (4:1 chloroform:ethyl acetate) indicated no starting material remained. The catalyst was recovered by filtration and the filtrate evaporated in vacuo to yield 1-acetoxy-2-methylcarbapenam-3-carboxylic acid [15 mg.; $R_f$ 0.0 (4:1 chloroform:ethyl acetate); ir ($CH_2Cl_2$) 1770, 1730 cm$^{-1}$].

The triethylammonium salt of the product was prepared by dissolving in methylene chloride, adding an equivalent of triethylamine and evaporating to dryness. Other, pharmaceutically acceptable amine salts are prepared in the same manner.

The sodium salt of this product is prepared by dissolving the free acid in water by the action of one equivalent of sodium bicarbonate and freeze drying the resultant solution.

By the same methods benzhydryl 2-methyl-1-oxocarbapenam-3-carboxylate and benzhydryl 1-hydroxy-2-methylcarbapenam-3-carboxylate are converted, respectively, to sodium 2-methyl-1-oxocarbapenam-3-carboxylate and sodium 1-hydroxy-2-methylcarbapenam-3-carboxylate.

EXAMPLE 11

2,2,2-Trichloroethyl 2-Methyl-1-oxocarbapen-2-em-3-carboxylate 2,2,2-Trichloroethyl 2-diazo-3-methyl-1-beta-oxoceph-3-em-4-carboxylate was converted to 2,2,2-trichloroethyl 2-methyl-1-oxocarbapen-2-em-3-carboxylate according to the procedure of Example 1, the reaction being monitored by ir spectral analysis. On a 10 mg. scale, 15 minutes were required to complete the reaction, while on a 100 mg. scale, 40 minutes were required. Product was isolated by evaporation of the reaction mixture in vacuo, without Raney nickel treatment.

EXAMPLE 12

2,2,2-Trichloroethyl 1-Hydroxy-2-methylcarbapen-2-em-3-carboxylate

Freshly prepared 2,2,2-trichloroethyl 2-methyloxocarbapen-2-em-3-carboxylate, made from 100 mg. (0.317 mmole) of the precursor oxide according to Example 11, was taken up in 2 ml. of methylene chloride and cooled to −78° C. Tetramethylammonium borohydride (23 mg., 0.079 mmole) was added. After 30 minutes, ir spectral analysis (1775 cm$^{-1}$) indicated a satisfactory reduction. The reaction was quenched with acetic acid (0.58 equivalent, 10 microl.), extracted twice with aqueous buffer solution (pH 7), dried over anhydrous magnesium sulfate and filtered to yield a solution of 2,2,2-trichloroethyl 1-hydroxy-2-methylcarbapen-2-em-3-carboxylate. If desired, this product is further isolated by evaporation to dryness in vacuo at reduced temperature.

By the same procedure, benzhydryl 2-methyl-1-oxocarbapen-2-em-3-carboxylate is converted to benzhydryl 1-hydroxy-2-methylcarbapen-2-em-3-carboxylate.

EXAMPLE 13

2,2,2-Trichloroethyl 1-Acetoxy-2-methylcarbapen-2-em-3-carboxylate

To a freshly prepared solution of 2,2,2-trichloroethyl 1-hydroxy-2-methylcarbapen-2-em-3-carboxylate in methylene chloride, prepared from 100 mg. (0.317 mmole) of the 1-beta-oxide by Examples 11 and 12) was added 24 microl. (0.317 mmole) of pyridine, 29 microl. (0.317 mmole) of acetic anhydride and 4 mg. of 4-dimethylaminopyridine. Infrared spectral analysis indicated clean conversion to the desired acetate. Following water wash and drying, evaporation to dryness gave 2,2,2-trichloroethyl 1-acetoxy-2-methylcarbapen-2-em-3-carboxylate [ir (CH$_2$Cl$_2$) 1780, 1725, 1700 cm$^{-1}$; R$_f$ 0.7–0.75 (4:1 chloroform:ethyl acetate].

By the same method, benzhydryl 1-hydroxy-2-methylcarbapen-2-em-3-carboxylate is converted to benzhydryl 1-acetoxy-2-methylcarbapen-2-em-3-carboxylate.

EXAMPLE 14

Sodium 1-Acetoxy-2-methylcarbapen-2-em-3-carboxylate

Method A

Selective, mild cleavage of the 2,2,2-trichloroethyl ester was achieved following the method of Just and Grozinger [Synthesis, 457 (1976)]. 2,2,2-Trichloroethyl 1-acetoxy-2-methylcarbapen-2-em-3-carboxylate (46 mg.) was dissolved in 0.812 ml. of tetrahydrofuran and cooled to 0° C. Zinc powder (85 mg.) was added, followed by aqueous phosphate buffer (0.162 ml., pH 5.5). The reaction mixture was stirred at 0° C. for 30 minutes, at which time tlc (4:1 chloroform:ethyl acetate) indicated no significant amount of reduction. The mixture was warmed to room temperature. Slow reaction was indicated by tlc. After 15 minutes, additional zinc power (85 mg.) was added and stirring continued for 3 hours, at which time tlc indicated reaction virtually complete. The reaction mixture was filtered and tetrahydrofuran was stripped from the filtrate in vacuo. The aqueous residue was adjusted to pH 7.0 with sodium bicarbonate and freeze dried to yield sodium 1-acetoxy-2-methylcarbapen-2-em-3-carboxylate [R$_f$ 0.0, (4:1 chloroform:ethyl acetate)].

Method B

By the methods of Example 10, benzhydryl 1-acetoxy-2-methylcarbapen-2-em-3-carboxylate is hydrogenolyzed to produce 1-acetoxy-2-methylcarbapen-2-em-3-carboxylic acid and its sodium salt.

EXAMPLE 15

Pivaloyloxymethyl 2-Acetoxymethyl-1-oxocarbapen-2-em-3-carboxylate

Pivaloyloxymethyl 2-diazo-1-beta-oxocephalosporanate (25 mg.) was dissolved in 25 ml. of methylene chloride, cooled to −78° C., and irradiated with a sun lamp. The reaction was monitored by infrared spectral analysis, following the disappearance of the diazo band. Reaction was essentially complete after 1 hour, resulting in a methylene chloride solution of pivaloyloxymethyl 2-acetoxymethyl-1-oxocarbapen-2-em-3-carboxylate [ir (CH$_2$Cl$_2$) 1810, 1740 cm$^{-1}$]. Product was isolated as an oil by evaporation in vacuo. Maintenance of a low temperature prevents undue decomposition during isolation.

EXAMPLE 16

Pivaloyloxymethyl 2-Methyl-1-oxo-6-(2-phenoxyacetamido)carbapen-2-em-3-carboxylate Following either one of the alternative methods of Example 1, pivaloyloxymethyl 2-diazo-3-methyl-1-beta-oxo-7-(2-phenoxyacetamido)ceph-3-em-4-carboxylate (5 mg.) in 5 ml. of methylene chloride (employing 30 minutes of irradiation time) was converted to pivaloyloxymethyl 2-methyl-1-oxo-6-(2-phenoxyacetamido)-carbapen-2-em-3-carboxylate [ir (CH$_2$Cl$_2$) 1805, 1740, 1715, 1680 cm$^{-1}$].

EXAMPLE 17

Pivaloyloxymethyl 2-Methyl-1-oxo-6-(2-phenoxyacetamido)carbapenam-3-carboxylate Freshly prepared pivaloyloxymethyl 2-methyl-1-oxo-6-(2-phenoxyacetamido)carbapen-2-em-3-carboxylate (prepared from 200 mg. of pivaloyloxymethyl 2-diazo-3-methyl-1-beta-oxo-7-(2-phenoxyacetamido)ceph-3-em-4-carboxylate (incorporating a 2 g. Raney nickel treatment into the isolation step) was taken up in 1 ml. of tetrahydrofuran and added to a stirred slurry of 2 g. of specially activated zinc powder (Example 2), in 6 ml. of acetic acid containing 30% tetrahydrofuran maintained at 0°–5° C. After stirring for 1 hour at this temperature, the reaction mixture was diluted with toluene and evaporated to dryness in vacuo to yield pivaloyloxymethyl 2-methyl-1-oxo-6-(2-phenoxyacetamido)carbapenam-3-carboxylate [R$_f$ 0.34 (9:1 chloroform:ethyl acetate; ir (CH$_2$Cl$_2$) 1790, 1750, 1680 cm$^{-1}$].

EXAMPLE 18

Pivaloyloxymethyl 1-Hydroxy-2-methyl-6-(2-phenoxyacetamido)carbapenam-3-carboxylate By the procedures of Examples 3 and 6, pivaloyloxymethyl 2-methyl-1-oxo-6-(2-phenoxyacetamido)carbapenam-3-carboxylate (102 mg., 0.23 mmole) in 3 ml. of methylene chloride was reduced by the action of tetrabutylammonium borohydride (15 mg., 0.06 mmole) and isolated to yield purified pivaloyloxymethyl 1-hydroxy-2-methyl-6-(2-phenoxyacetamido)carbapenam-3-carboxylate [68 mg.; R$_f$ 0.26 (4:1 chloroform:ethyl acetate; ir (CH$_2$Cl$_2$) 1775, 1750, 1675 cm$^{-1}$].

EXAMPLE 19

Pivaloyloxymethyl 1-Acetoxy-2-methyl-6-(2-phenoxyacetamido)carbapenam-3-carboxylate By the procedure of Example 18, pivaloyloxymethyl 2-methyl-1-oxo-6-(2-phenoxyacetamido)carbapenam-3-carboxylate (135 mg., 0.3 mmoles) was reduced with tetrabutylammonium borohydride and the isolation taken to the stage at which a washed, dried and filtered solution of pivaloyloxymethyl 1-hydroxy-2-methyl-6-(2-phenoxyacetamido)carbapenam-3-carboxylate in methylene chloride was in hand. This solution was cooled to −10° C. Pyridine (24 mg., 0.3 mmoles), acetic anhydride (31 mg., 0.3 mmoles) and 4-dimethylaminopyridine (4 mg., 0.3 mmoles) were added in sequence. After stirring for 1 hour at −10° C., tlc (4:1 chlorform:ethyl acetate) indicated complete acetylation. The reaction mixture was diluted with toluene and stripped to dryness in vacuo, with toluene chases. Chromatography on silica gel (20:1 methylene chloride:ethyl acetate) gave pivaloyloxymethyl 1-acetoxy-2-methyl-6-(2-phenoxyacetamido)carbapenam-3-carboxylate [10 mg.; R$_f$ 0.36 (4:1 chloroform:ethyl acetate); ir (CH$_2$Cl$_2$) 1780, 1750, 1685 cm$^{-1}$].

EXAMPLE 20

Benzhydryl 2-Methyl-1-oxo-6-(2-phenoxyacetamido)carbapen-2-em-3-carboxylate

Benzhydryl 2-diazo-3-methyl-1-beta-oxo-7-(2-phenoxyacetamido)ceph-3-em-4-carboxylate (200 mg.) in 200 ml. methylene chloride at −78° C. in a pyrex flask was irradiated with a sun lamp for 30 minutes. The reaction mixture was evaporated to dryness, yielding benzhydryl 2-methyl-1-oxo-6-(2-phenoxyacetamido)-carbapen-2-em-3-carboxylate [ir (CH$_2$Cl$_2$) 1810, 1720, 1690 cm$^{-1}$].

By the same procedure 2,2,2-trichloroethyl 2-diazo-1-beta-oxo-7-(2-phenoxyacetamido)ceph-3-em-4-carboxylate [Ebbinghaus et al., J. Org. Chem. 44, 4697 (1979)] is rearranged to 2,2,2-trichloroethyl 2-methyl-1-oxo-6-(2-phenoxyacetamido)carbapen-2-em-3-carboxylate and benzhydryl 2-diazo-1-beta-oxo-7-(2-phenoxyacetamido)cephalosporanate (Ebbinghaus et al., loc. cit.) is rearranged to benzhydryl 2-(acetoxymethyl-1-oxo-6-(2-phenoxyacetamido)carbapen-2-em-3-carboxylate.

EXAMPLE 21

Benzhydryl 2-Methyl-1-oxo-6-(2-phenoxyacetamido)carbapenam-3-carboxylate

Benzhydryl 2-methyl-1-oxo-6-(2-phenoxyacetamido)carbapen-2-em-2-carboxylate (freshly prepared from 200 mg. of benzhydryl 2-diazo-3-methyl-1-beta-oxo-7-(2-phenoxyacetamido)ceph-3-em-4-carboxylate according to the procedure of Example 20, was taken up in the minimum necessary tetrahydrofuran and added to a mixture of 2 g. of specially activated zinc powder (Example 2) slurried in a mixture 4 ml. of acetic acid and 2 ml. of tetrahydrofuran at −10° C. The reaction mixture was stirred for 1 hour at −10° C., diluted with toluene, evaporated to dryness in vacuo, with toluene chases, taken up in toluene, zinc and zinc salts removed by filtration, and reevaporated to yield benzhydryl 2-methyl-1-oxo-6-(2-phenoxyacetamido)carbapenam-3-carboxylate [140 mg., ir (CH$_2$Cl$_2$) 1790, 1745, 1680 cm$^{-1}$].

By the same procedure, with isolation according to the analogous zinc reduction of Example 34, method B, 2,2,2-trichloroethyl 2-methyl-1-oxo-6-(2-phenoxyacetamido)carbapen-2-em-3-carboxylate is converted to sodium 2-methyl-1-oxo-6-(2-phenoxyacetamido)carbapenam-3-carboxylate.

EXAMPLE 22

Benzhydryl 1-Hydroxy-2-methyl-6-(2-phenoxyacetamido)-carbapenam-3-carboxylate According to the procedures detailed in Example 3, benzhydryl 2-methyl-1-oxo-6-(2-phenoxyacetamido)-carbapenam-3-carboxylate (138 mg., 0.28 mmole) in 15 ml. of methylene chloride was reduced with tetrabutylammonium borohydride (18 mg., 0.07 mmole) at −78° C., monitored and isolated as a washed, dried methylene chloride solution of benzhydryl 1-hydroxy-2-methyl-6-(2-phenoxyacetamido)carbapenam-3-carboxylate [R$_f$ 0.24 (4:1 chloroform:ethyl acetate)]. If desired, the product is further isolated by evaporation to dryness in vacuo.

EXAMPLE 23

Benzhydryl 1-Acetoxy-2-methyl-6-(2-phenoxyacetamido)carbapenam-3-carboxylate The washed, dried methylene chloride solution of benzhydryl 1-hydroxy-2-methyl-6-(2-phenoxyacetamido)carbapenam-3-carboxylate, freshly prepared according to Example 22 was cooled to −10° C. Pyridine (22 mg., 0.28 mmole), acetic anhydride (29 mg., 0.28 mmole) and 4-dimethylaminopyridine (3.4 mg., 0.028 mmoles) were added in sequence. After stirring for 1 hour at −10° C., tlc (4:1 chloroform:ethyl acetate) indicated acetylation was complete. The reaction mixture was evaporated to dryness in vacuo with toluene chases. Chromatography on silica gel using a methylene chloride-ethyl acetate gradient (0 to 7.5% ethyl acetate) afforded benzhydryl 1-acetoxy-2-methyl-6-(2-phenoxyacetamido)carbapenam-3-carboxylate [18 mg.; R$_f$ 0.56 (4:1 chloroform:ethyl acetate; ir (CHCl$_3$) 1780, 1730, 1680 cm$^{-1}$].

EXAMPLE 24

1-Acetoxy-2-methyl-6-(2-phenoxyacetamido)carbapenam-3-carboxylic Acid

Benzhydryl 1-acetoxy-2-methyl-6-(2-phenoxyacetamido)carbapenam-3-carboxylate (18 mg.) was dissolved in 3 ml. of ethyl acetate. Hydrogenation catalyst (18 mg. of 10% palladium on carbon) was added and the mixture hydrogenated at atmospheric pressure and room temperature for 1 hour. When tlc (4:1 chloroform:ethyl acetate) indicated no change, a second aliquot of catalyst (18 mg.) was added. According to tlc assay, some conversion occurred during the next hour, at which time a third aliquot of catalyst (18 mg.) was added. At the end of another hour of hydrogenation, tlc assay indicated reduction to be complete. Catalyst was recovered by filtration with ethyl acetate wash. The combined filtrate and washes were evaporated to dryness in vacuo to yield 1-acetoxy-2-methyl-6-(2-phenoxyacetamido)carbapenam-3-carboxylic acid [R$_f$ 0.77 (18:1 acetone:water); ir (CH$_2$Cl$_2$) 1775, 1725, 1675 cm$^{-1}$].

EXAMPLE 25

Pivaloyloxymethyl 6-Methoxy-2-methyl-1-oxo-6-(2-phenoxyacetamido)-carbapen-2-em-3-carboxylate Method A Following Example 1, pivaloyloxymethyl 2-diazo-7-methoxy-3-methyl-1-beta-oxo-7-(2-phenoxyacetamido)-ceph-3-em-4-carboxylate (15 mg.) in 15 ml. of methylene chloride was irradiated with a sun lamp at −78° C. for 10 minutes at which time ir analysis indicated rearrangement was complete. Raney nickel (150 mg.) was added and stirring continued for 30 minutes at −78° C. Raney nickel was removed by filtration, and the filtrate evaporated in vacuo to yield pivaloyloxymethyl 6-methoxy-2-methyl-1-oxo-6-(2-phenoxyacetamido)carbapen-2-em-3-carboxylate [ir (CH$_2$Cl$_2$) 1810, 1750, 1715, 1690 cm$^{-1}$].

Method B

Following Example 1, pivaloyloxymethyl 2diazo-7-methoxy-3-methyl-1-beta-oxo-7-(2-phenoxyacetamido)-ceph-3-em-4-carboxylate (50 mg.) in 50 ml. of methylene chloride was irradiated with a sun lamp at −78° C.

for 15 minutes at which time ir analysis indicated rearrangement was complete. Evaporation of the reaction mixture in vacuo afforded pivaloyloxymethyl 6-methoxy-2-methyl-1-oxo-6-(2-phenoxyacetamido)carbapen-2-em-3-carboxylate suitable for further processing.

EXAMPLE 26

Pivaloyloxymethyl 6-Methoxy-2-methyl-1-oxo-6-(2-phenoxyacetamido)-carbapenam-3-carboxylate The freshly prepared pivaloyloxymethyl 6-methoxy-2-methyl-1-oxo-6-(2-phenoxyacetamido)carbapen-2-em-3-carboxylate of Method B, Example 25, was dissolved in the minimum necessary tetrahydrofuran and added to a slurry of specially activated zinc powder (Example 2; 500 mg.) in a mixture of 1 ml. acetic acid and 0.5 ml. of tetrahydrofuran maintained at 0° C. After stirring for 1 hour at 0° C., the reaction mixture was diluted with toluene, evaporated to dryness in vacuo and chased several times with toluene. The residue was redissolved in methylene chloride, zinc removed by filtration, and the filtrate reconcentrated to dryness in vacuo. The residue was taken up in ether, insoluble impurities removed by filtration and the filtrate again evaporated to dryness in vacuo to yield pivaloyloxymethyl 6-methoxy-2-methyl-1-oxo-6-(2-phenoxyacetamido)carbapenam-3-carboxylate [20 mg.; $R_f$ 0.70 (4:1 chloroform:ethyl acetate)].

EXAMPLE 27

Pivaloyloxymethyl 1-Hydroxy-6-methoxy-2-methyl-6-(2-phenoxyacetamido)carbapenam-3-carboxylate Pivaloyloxymethyl 6-methoxy-2-methyl-1-oxo-6-(2-phenoxyacetamido)carbapenam-3-carboxylate (79 mg., 0.17 mmole) in 10 ml. of methylene chloride was reduced at −78° C. with tetrabutylammonium borohydride (11 mg., 0.04 mmole), the reaction monitored, and crude product isolated according to Example 3. Chromatography on silica gel (3:1 methylene chloride:ethyl acetate as eluant), monitored by ir, gave pivaloyloxymethyl 1-hydroxy-6-methoxy-2-methyl-6-(2-phenoxyacetamido)carbapenam-3-carboxylate [9.8 mg., 12%; $R_f$ 0.3 (4:1 chloroform:ethyl acetate); ir ($CH_2Cl_2$) 1770, 1750, 1670 cm$^{-1}$].

EXAMPLE 28

Pivaloyloxymethyl 2-Methyl-1-oxo-6-[2-phenyl-2-(4-ethyl-2,3-dioxopiperazine-1-carboxamido)acetamido]carbapen-2-em-3-carboxylate Following Example 1 pivaloyloxymethyl 2-diazo-3-methyl-1-beta-oxo-7-[2-phenyl-2-(4-ethyl-2,3-dioxopiperazine-1-carboxamido)acetamido]ceph-3-em-4-carboxylate (10 mg.) was dissolved in 10 ml. of methylene chloride, cooled to −78° C., and irradiated with a sun lamp for 20 minutes. The reaction was evaporated to dryness in vacuo to yield pivaloyloxymethyl 2-methyl-1-oxo-6-[2-phenyl-2-(4-ethyl-2,3-dioxopiperazine-1-carboxamido)acetamido]carbapen-2-em-3-carboxylate [ir ($CH_2Cl_2$) 1815, 1750, 1700 cm$^{-1}$].

EXAMPLE 29

Pivaloyloxymethyl 2-Methyl-1-oxo-6-[2-phenyl-2-(4-ethyl-2,3-dioxopiperazine-1-carboxamido)acetamido]carbapenam-3-carboxylate Method A Pivaloyloxymethyl 2-methyl-1-oxo-6-[2-phenyl-2-(4-ethyl-2,3dioxopiperazine-1-carboxamido)acetamido]-carbapen-2-em-3-carboxylate [freshly prepared according to Example 28 from 127 mg. (0.19 mmole) of the ceph-3-em precursor] was taken up in a minimum of tetrahydrofuran and added to a slurry of activated zinc powder (1.27 g.) in a mixture of 26 ml. of acetic acid and 12 ml. of tetrahydrofuran at 0° C. Stirring at 0° C. was continued for 1 hour. Product was isolated according to procedures detailed in Example 2, followed by trituration with ether, yielding pivaloyloxymethyl 2-methyl-1-oxo-6-[2-phenyl-2-(4-ethyl-2,3-dioxopiperazine-1-carboxamido)acetamido]carbapenam-3-carboxylate [30 mg.; $R_f$ 0.91 (ethyl acetate)]. An additional 13 mg. of less pure product was obtained by evaporation of the ether triturate to dryness.

Method B

By method B of Example 69 below, sodium 2-methyl-1-oxo-6-[2-phenyl-2-(4-ethyl-2,3-dioxopiperazine-1-carboxamido)acetamido]carbapenam-3-carboxylate is esterified to produce pivaloyloxymethyl 2-methyl-1-oxo-6-[2-phenyl-2-(4-ethyl-2,3-dioxopiperazine-1-carboxamido)acetamido]carbapenam-3-carboxylate.

The same method, but substituting an equivalent quantity of bromomethyl acetate, 1,3-dihydro-3-oxobenzo[c]furan-1-yl bromide or 1-ethoxycarbonyloxyethyl chloride, as appropriate, is employed to prepare the corresponding acetoxymethyl, 1,3-dihydro-3-oxobenzo[c]furan-1-yl and 1-ethoxycarbonyloxyethyl 2-methyl-1-oxo-6-[2-phenyl-2-(4-ethyl-2,3-dioxopiperazine-1-carboxamido)acetamido]carbapenam-3-carboxylates.

EXAMPLE 30

Pivaloyloxymethyl 1-Hydroxy-2-methyl-6-[2-phenyl-2-(4-ethyl-2,3-dioxopiperazine-1-carboxamido)acetamido]carbapenam-3-carboxylate Method A Pivaloyloxymethyl 2-methyl-1-oxo-6-[2-phenyl-2-(4-ethyl-2,3dioxopiperazine-1-carboxamido)acetamido]-carbapenam-3-carboxylate (103 mg., 0.16 mmole) in 10 ml. of methylene chloride was reacted with tetrabutylammonium borohydride (11 mg., 0.04 mmole) at −78° C. After 15 minutes tlc (ethyl acetate) indicated reduction was complete. Isolation according to Example 3, except using 1:1 chloroform:ethyl acetate as eluant in the chromatography, afforded pivaloyloxymethyl 1-hydroxy-2-methyl-6-[2-phenyl-2-(4-ethyl-2,3-dioxopiperazine-1-carboxamido)acetamido]carbapenam-3-carboxylate [15 mg., 15%; ir ($CH_2Cl_2$) 1775, 1760, 1720, 1690 cm$^{-1}$; $R_f$ 0.0 (ethyl acetate)].

By the same method, the other esters of Example 29 are converted to the corresponding acetoxymethyl, 1,3-dihydro-3-oxobenzo[c]furan-1-yl and 1-ethoxycarbonyloxyethyl 1-hydroxy-2-methyl-6-[2-phenyl-2-(4-ethyl-2,3dioxopiperazine-1-carboxamido)acetamido]-carbapenam-3-carboxylates.

Method B

By Method B of Example 39 below, sodium 1-hydroxy-2-methyl-6-[2-phenyl-2-(4-ethyl-2,3-dioxopiperazine-1-carboxamido)acetamido]carbapenam-3-carboxylate is converted to pivaloyloxymethyl 1-hydroxy-2-methyl-6-[2-phenyl-2-(4-ethyl-2,3-dioxopiperazine-1-carboxamido)acetamido]carbapenam-3-carboxylate.

By the same method, but substituting an equivalent quantity of the appropriate bromomethyl acetate, 1,3-dihydro-3-oxobenzo[c]furan-1-yl bromide or 1-ethoxycarbonyloxyethyl chloride, the corresponding acetoxymethyl, 1,3-dihydro-3-oxobenzo[c]furan-1-yl and 1-ethoxycarbonyloxyethyl 1-hydroxy-2-methyl-6-[2-phenyl-2-(4-ethyl-2,3-dioxopiperazine-1-carboxamido)acetamido]carbapenam-3-carboxylates are prepared.

EXAMPLE 31

2-Naphthylmethyl 2-Methyl-4-oxo-6-[2-phenyl-2-(4-ethyl-2,3-dioxopiperazine-1-carboxamido)acetamido]carbapen-2-em-3-carboxylate Following the procedure of Example 1 (without Raney nickel treatment), 2-naphthylmethyl 2-diazo-3-methyl-1-beta-oxo-7-[2-phenyl-2-(4-ethyl-2,3-dioxopiperazine-1-carboxamido)acetamido]ceph-3-em-4-carboxylate (237 mg.) was converted to 2-naphthylmethyl 2-methyl-1-oxo-6-[2-phenyl-2-(4-ethyl-2,3-dioxopiperazine-1-carboxamido)acetamido]carbapen-2-em-3-carboxylate.

By the same method 2,2,2-trichloroethyl 2-diazo-3-methyl-1-beta-oxo-7-[2-phenyl-2-(4-ethyl-2,3-dioxopiperazine-1-carboxamido)acetamido]ceph-3-em-4-carboxylate is converted to 2,2,2-trichloroethyl 2-methyl-1-oxo-6-[2-phenyl-2-(4-ethyl-2,3dioxopiperazine-1-carboxamido)acetamido]carbapen-2-em-3-carboxylate.

EXAMPLE 32

2-Naphthylmethyl 2-Methyl-1-oxo-6-[2-phenyl-2-(4-ethyl-2,3-dioxopiperazine-1-carboxamido)acetamido]carbapenam-3-carboxylate The 2-naphthylmethyl 2-methyl-1-oxo-6-[2-phenyl-(4-ethyl-2,3-dioxopiperazine-1-carboxamido)acetamido]carbapen-2-em-3-carboxylate of Example 31 was taken up in a minimum of tetrahydrofuran, and added to a slurry of activated zinc (2.37 g.) in 5 ml. of acetic acid-30% tetrahydrofuran at 0° C. After 1 hour at 0° C., product was isolated according to procedures detailed in Example 2. The resulting product was taken up in ether, insolubles removed by filtration, and the filtrate evaporated to dryness in vacuo to yield 2-naphthylmethyl 2-methyl-1-oxo-6-[2-phenyl-2-(4-ethyl-2,3-dioxopiperazine-1-carboxamido)acetamido]carbapenam-3-carboxylate [36 mg., 16%; $R_f$ 0.48 (ethyl acetate)].

EXAMPLE 33

2-Naphthylmethyl 1-Hydroxy-2-methyl-6-[2-phenyl-2-(4-ethyl-2,3-dioxopiperazine-1-carboxamido)acetamido]carbapenam-3-carboxylate 2-Naphthylmethyl 2-methyl-1-oxo-6-[2-phenyl-2-(4-ethyl-2,3-dioxopiperazine-1-carboxamido)acetamido]carbapenam-3-carboxylate (36 mg., 0.056 mmole) in 3.6 ml. of methylene chloride at −78° C. was reduced with tetrabutylammonium borohydride (3.6 mg., 0.014 mmoles). After a 1 hour reaction time at −78° C., tlc (ethyl acetate) indicated conversion was complete. Isolation according to Example 3 (without chromatography) afforded 2-naphthylmethyl 1-hydroxy-2-methyl-6-[2-phenyl-2-(4-ethyl-2,3-dioxopiperazine-1-carboxamido)acetamido]carbapenam-3-carboxylate [36 mg.; $R_f$ 0.13 (ethyl acetate)].

EXAMPLE 34

Sodium 1-Hydroxy-2-methyl-6-[2-phenyl-2-(4-ethyl-2,3-dioxopiperazine-1-carboxamido)acetamido]carbapenam-3-carboxylate Method A 2-Naphthylmethyl 1-hydroxy-2-methyl-6-[2-phenyl-2-(4-ethyl-2,3-dioxopiperazine-1-carboxamido)acetamido]carbapenam-3-carboxylate (36 mg., 0.056 mmole) was dissolved in 2 ml. of dioxane. Water (1 ml.), sodium bicarbonate (4.7 mg., 0.056 mmole) and hydrogenation catalyst (36 mg. of 10% palladium on carbon) were added and the mixture was hydrogenated at 50 psig and room temperature for 30 minutes. Monitoring by tlc (9:1 acetone:water and 90:10:2 chloroform::ethanol:acetic acid) indicated that hydrogenation was incomplete. An additional 36 mg. of 10% palladium on carbon was added and hydrogenation, under the same conditions, resumed for 30 minutes, at which time tlc monitoring indicated reaction was complete. Catalyst was recovered by filtration and the filtrate freeze dried to yield sodium 1-hydroxy-2-methyl-6-[2-phenyl-2-(4-ethyl-2,3-dioxopiperazine-1-carboxamido)acetamido]carbapenam-3-carboxylate [10 mg., 34%; $R_f$ 0.3 (9:1 acetone:water; $R_f$ 0.3 (90:10:2 chloroform:ethanol:acetic acid); ir (nujol mull) 1770, 1750, 1710 cm$^{-1}$].

By the same method 2-naphthylmethyl 2-methyl-1-oxocarbapenam-3-carboxylate is converted to sodium 2-methyl-1-oxocarbapenam-3-carboxylate.

Method B

By the method of Examples 2, 7, 17, 21, etc., 2,2,2-trichloroethyl 2-methyl-1-oxo-6-[2-phenyl-2-(4-ethyl-2,3-dioxopiperazine-1-carboxamido)carbapen-2-em-3-carboxylate is reduced (with simultaneous deesterification) to yield 2-methyl-1-oxo-6-[2-phenyl-2-(4-ethyl-2,3-dioxopiperazine-1-carboxamido)acetamido]carbapenam-3-carboxylic acid, isolated as sodium salt by filtration of the reaction mixture, evaporation in vacuo, freeze drying of the filtrate, dissolution of the desired product in water at pH 7.0 (with sodium bicarbonate), filtration and freeze drying the filtrate.

By the same method 2,2,2-trichloroethyl2-methyl-1-oxocarbapen-2-em-3-carboxylate is converted to sodium 2-methyl-1-oxocarbapenam-3-carboxylate.

EXAMPLE 35

Pivaloyloxymethyl 2-Methyl-6-(5-methyl-3-phenylisoxazole-4-carboxamido)-1-oxocarbapen-2-em-3-carboxylate Employing methods detailed in Example 1, pivaloyloxymethyl 2-diazo-3-methyl-7-(5-methyl-3-phenylisoxazole-4-carboxamido)-1-beta-oxoceph-3-em-4-carboxylate (222 mg.) was irradiated, the reaction monitored and product isolated (without Raney nickel treatment), to yield pivaloyloxymethyl 2-methyl-6-(5-methyl-3-phenylisoxazole-4-carboxamido)-1-oxocarbapen-2-em-3-carboxylate [ir ($CH_2Cl_2$) 1810, 1750, 1710, 1680 cm$^{-1}$].

EXAMPLE 36

Pivaloyloxymethyl
2-Methyl-6-(5-methyl-3-phenylisoxazole-4-carboxamido)-1-oxocarbapenam-3-carboxylate The pivaloyloxymethyl 2-methyl-6-(5-methyl-3-phenylisoxazole-4-carboxamido)-1-oxocarbapen-2-em-3-carboxylate of Example 35 was reduced with zinc (2.22 g.) in 5.3 ml. of acetic acid-30% tetrahydrofuran, by methods detailed in Example 2, and isolated according to methods detailed in Examples 2 and 32, affording pivaloyloxymethyl 2-methyl-6-(5-methyl-3-phenylisoxazole-4-carboxamido)-1-oxocarbapenam-3-carboxylate [100 mg., 50% over-all; ir $(CH_2Cl_2)$ 1790, 1750, 1670 $cm^{-1}$].

EXAMPLE 37

Pivaloyloxymethyl
1-Hydroxy-2-methyl-6-(5-methyl-3-phenylisoxazole-4-carboxamido)carbapenam-3-carboxylate By the methods detailed in Example 33, pivaloyloxymethyl 2-methyl-6-(5-methyl-3-phenylisoxazole-4-carboxamido)-1-oxocarbapenam-3-carboxylate (100 mg., 0.2 mmole) in 10 ml. of methylene chloride at −78° C. was reduced with tetramethylammonium borohydride (13 mg., 0.05 mmole), the reaction monitored and the product isolated. Final purification by chromatography on silica gel (3:1 methylene chloride:ethyl acetate) afforded pivaloyloxymethyl 1-hydroxy-2-methyl-6-(5-methyl-3-phenylisoxazole-4-carboxamido)carbapenam-3-carboxylate [18 mg., ir $(CH_2Cl_2)$ 1775, 1750, 1660 $cm^{-1}$].

EXAMPLE 38

Pivaloyloxymethyl
6-D-(2-Benzyloxycarbonylamino-2-phenylacetamido)-2-methyl-1-oxocarbapen-2-em-3-carboxylate By the method of Examples 1, 6, 11, 15, 16, etc., pivaloyloxymethyl 7-D-(2-benzyloxycarbonylamino-2-phenylacetamido)-2-diazo-3-methyl-1-beta-oxoceph-3-em-4-carboxylate is rearranged to produce pivaloyloxymethyl 6-D-(2-benzyloxycarbonylamino-2-phenylacetamido)-2-methyl-1-oxocarbapen-2-em-3-carboxylate.

EXAMPLE 39

Pivaloyloxymethyl
6-D-(2-Benzyloxycarbonylamino-2-phenylacetamido)-2-methyl-1-oxocarbapenam-3-carboxylate By the method of Examples 2, 7, 17, 21, etc., pivaloyloxymethyl 6-D-(2-benzyloxycarbonylamino-2-phenylacetamido)-2-methyl-1-oxocarbapen-2-em-3-carboxylate is reduced to pivaloyloxymethyl 6-D-(2-benzyloxycarbonylamino-2-phenylacetamido)-2-methyl-1-oxocarbapenam-3-carboxylate.

EXAMPLE 40

Pivaloyloxymethyl
6-D-(2-Amino-2-phenylacetamido)-2-methyl-1-oxocarbapenam-3-carboxylate By the method of Example 10, pivaloyloxymethyl 6-D-(2-benzyloxycarbonylamino-2-phenylacetamido)-2-methyl-1-oxocarbapenam-3-carboxylate is hydrogenolyzed to pivaloyloxymethyl 6-D-(2-amino-2-phenylacetamido-2-methyl-1-oxocarbapenam-3-carboxylate. The catalyst is recovered by filtration, and product recovered by evaporation of the filtrate to dryness in vacuo, with toluene chase.

EXAMPLE 41

Pivaloyloxymethyl
6-D-(2-Benzyloxycarbonylamino-2-phenylacetamido)-1-hydroxy-2-methylcarbapenam-3-carboxylate By the method of Examples 3, 8, 18, 22, etc., pivaloyloxymethyl 6-D-(2-benzyloxycarbonylamino-2-phenylacetamido)-2-methyl-1-oxocarbapenam-3-carboxylate is reduced to pivaloyloxymethyl 6-D-(2-benzyloxycarbonylamino-2-phenylacetamido)-1-hydroxy-2-methylcarbapenam-3-carboxylate.

EXAMPLE 42

Pivaloyloxymethyl
6-D-(2-Amino-2-phenylacetamido)-1-hydroxy-2-methylcarbapenam-3-carboxylate Method A By the method of Example 40, pivaloyloxymethyl 6-D-(2-benzyloxycarbonylamino-2-phenylacetamido)-1-hydroxy-2-methylcarbapenam-3-carboxylate is hydrogenolyzed to produce pivaloyloxymethyl 6-D-(2-amino-2-phenylacetamido)-1-hydroxy-2-methylcarbapenam-3-carboxylate.

Method B

By the method of Examples 3, 8, 18, 22, etc., pivaloyloxymethyl 6-D-(2-amino-2-phenylacetamido)-2-methyl-1-oxocarbapenam-3-carboxylate is reduced to pivaloyloxymethyl 6-D-(2-amino-2-phenylacetamido)-1-hydroxy-2-methylcarbapenam-3-carboxylate.

EXAMPLE 43

Pivaloyloxymethyl
1-Acetoxy-6-D-(2-benzyloxycarbonylamino-2-phenylacetamido)-2-methylcarbapenam-3-carboxylate By the method of Examples 9, 19, 23, etc., pivaloyloxymethyl 6-D-(2-benzyloxycarbonylamino-2-phenylacetamido)-1-hydroxy-2-methylcarbapenam-3-carboxylate is acetylated to produce pivaloyloxymethyl 1-acetoxy-6-D-(2-benzyloxycarbonylamino-2-phenylacetamido)-2-methylcarbapenam-3-carboxylate.

EXAMPLE 44

Pivaloyloxymethyl
1-acetoxy-6-D-(2-amino-2-phenylacetamido)-2-methylcarbapenam-3-carboxylate By the method of Example 40, pivaloyloxymethyl 1-acetoxy-6-D-(2-benzyloxycarbonylamino-2-phenylacetamido)-2-methylcarbapenam-3-carboxylate is hydrogenolyzed to afford pivaloyloxymethyl 1-acetoxy-6-D-(2-amino-2-phenylacetamido)-2-methylcarbapenam-3-carboxylate.

EXAMPLE 45

Benzhydryl
6-D-(2-Benzyloxycarbonylamino-2-phenylacetamido)-2-methyl-1-1-oxocarbapen-2-em-3-carboxylate By the method of Examples 1, 6, 11, 15, etc., benzhydryl 7-D-(2-benzyloxycarbonylamino-2-phenylacetamido)-2-diazo-3-methyl-1-beta-oxoceph-3-em-4-carboxylate was rearranged to benzhydryl 6-D-(2-benzyloxycarbonylamino-2-phenylacetamido)-2-methyl-1-oxocarbapen-2-em-3-carboxylate.

EXAMPLE 46

Benzhydryl 6-D-(2-Benzyloxycarbonylamino-2-phenylacetamido)-2-methyl-1-oxocarbapenam-3-carboxylate By the method of Examples 2, 7, 17, 21, etc., benzhydryl 6-D-(2-benzyloxycarbonylamino-2-phenylacetamido)-2-methyl-1-oxocarbapen-2-em-3-carboxylate is reduced to benzhydryl 6-D-(2-benzyloxycarbonylamino-2-phenylacetamido)-2-methyl-1-oxocarbapenam-3-carboxylate.

EXAMPLE 47

6-D-(2-Amino-2-phenylacetamido)-2-methyl-1-oxocarbapenam-3-carboxylic Acid

By the method of Example 40 both ester groups of benzhydryl 6-D-(2-benzyloxycarbonylamino-2-phenylacetamido)-2-methyl-1oxocarbapenam-3-carboxylate are hydrogenolyzed to 6-D-(2-amino-2-phenylacetamido)-2-methyl-1-oxocarbapenam-3-carboxylic acid.

EXAMPLE 48

Benzhydryl 6-D-(2-Benzyloxycarbonylamino-2-phenylacetamido)-1-hydroxy-2-methylcarbapenam-3-carboxylate By the method of Examples 3, 8, 18, 22, etc., benzhydryl 6-D-(2-benzyloxycarbonylamino-2-phenylacetamido)-2-methyl-1-oxocarbapenam-3-carboxylate is reduced to benzhydryl 6-D-(2-benzyloxycarbonylamino-2-phenylacetamido)-1-hydroxy-2-methylcarbapenam-3-carboxylate.

EXAMPLE 49

6-D-(2-Amino-2-phenylacetamido)-1-hydroxy-2-methylcarbapenam-3-carboxylic Acid By the method of Example 40, benzhydryl 6-D-(2-benzyloxycarbonylamino-2-phenylacetamido)-1-hydroxy-2-methylcarbapenam-3-carboxylate is converted to 6-D-(2-amino-2-phenylacetamido)-1-hydroxy-2-methylcarbapenam-3-carboxylic acid.

EXAMPLE 50

Benzhydryl 1-Acetoxy-6-D-(2-benzyloxycarbonylamino-2-phenylacetamido)-2-methylcarbapenam-3-carboxylate By the method of Examples 9, 19, 23, etc., benzhydryl 6-D-(2-benzyloxycarbonylamino-2-phenylacetamido-1-hydroxy-2-methylcarbapenam-3-carboxylate is acetylated to yield benzhydryl 1-acetoxy-6-D-(2-benzyloxycarbonylamino-2-phenylacetamido)-2-methylcarbapenam-3-carboxylate.

EXAMPLE 51

1-Acetoxy-6-D-(2-amino-2-phenylacetamido)-2-methylcarbapenam-3-carboxylic Acid By the method of Example 40, benzhydryl 1-acetoxy-6-D-(2-benzyloxycarbonylamino-2-phenylacetamido)-2-methylcarbapenam-3-carboxylate is converted to 1-acetoxy-6-D-(2-amino-2-phenylacetamido)-2-methylcarbapenam-3-carboxylic acid.

EXAMPLE 52

Pivaloyloxymethyl 6-(2-benzhydryloxycarbonyl-2-phenylacetamido)-2-methyl-1-oxocarbapen-2-em-3-carboxylate By the method of Examples 1, 6, 11, 15, etc., pivaloyloxymethyl 7-(2-benzhydryloxycarbonyl-2-phenylacetamido)-2-diazo-3-methyl-1-beta-oxoceph-3-em-4-carboxylate is rearranged to pivaloyloxymethyl 6-(2-benzhydryloxycarbonyl-2-phenylacetamido)-2-methyl-1-oxocarbapen-2-em-3-carboxylate.

By the same method, the other esters of Preparation 47 are converted to the corresponding pivaloyloxymethyl 6-(2-benzyloxycarbonyl-2-phenylacetamido)-2-methyl-1-oxocarbapen-2-em-3-carboxylate and 2-methyl-6-[2-(2-naphthylmethoxycarbonyl)-2-phenylacetamido]-1-oxocarbapen-2-em-3-carboxylate.

EXAMPLE 53

Pivaloyloxymethyl 6-(2-Benzhydryloxycarbonyl-2-phenylacetamido)-2-methyl-1-oxocarbapenam-3-carboxylate By the method of Examples 2, 7, 17, 21, etc., pivaloyloxymethyl 6-(2-benzhydryloxycarbonyl-2-phenylacetamido)-2-methyl-1-oxocarbapen-2-em-3-carboxylate is reduced to pivaloyloxymethyl 6-(2-benzhydryloxycarbonyl-2-phenylacetamido)-2-methyl-1-oxocarbapenam-3-carboxylate.

By the same method the other carbapen-2-em esters of Example 52 are reduced to the corresponding pivaloyloxymethyl 6-(2-benzyloxycarbonyl-2-phenylacetamido)-2-methyl-1-oxocarbapenam-3-carboxylate and 2-methyl-6-[2-(2-naphthylmethoxycarbonyl)-2-phenylacetamido]-1-oxocarbapenam-3-carboxylate.

EXAMPLE 54

Pivaloyloxymethyl 6-(2-Carboxy-2-phenylacetamido)-2-methyl-1-oxocarbapenam-3-carboxylate By the method of Example 34, pivaloyloxymethyl 6-(2-benzhydryloxycarbonyl-2-phenylacetamido)-2-methyl-1-oxocarbapenam-3-carboxylate is hydrogenolyzed to pivaloyloxymethyl 6-(2-carboxy-2-phenylacetamido)-2-methyl-1-oxocarbapenam-3-carboxylate, isolated as the sodium salt.

By the same method, the corresponding benzyl and 2-naphthylmethyl esters are hydrogenolyzed to yield the same product.

EXAMPLE 55

Pivaloyloxymethyl 6-(2-Benzhydryloxycarbonyl-2-phenylacetamido)-1-hydroxy-2-methylcarbapenam-3-carboxylate By the method of Examples 3, 8, 18, 22, etc., pivaloyloxymethyl 6-(2-benzyloxycarbonyl-2-phenylacetamido)-2-methyl-1-oxocarbapenam-3-carboxylate is reduced to pivaloyloxymethyl 6-(2-benzyloxycarbonyl-2-phenylacetamido)-1-hydroxy-2-methylcarbapenam-3-carboxylate.

By the same method, the other 4-oxocarbapenam esters of Example 53 are converted to the corresponding pivaloyloxymethyl 6-(2-benzyloxycarbonyl-2-phenylacetamido)-1-hydroxy-2-methylcarbapenam-3-carboxylate and pivaloyloxymethyl 1-hydroxy-2-methyl-6-[2-(2-naphthylmethoxycarbonyl)-2-phenylacetamido]-carbapenam-3-carboxylate.

EXAMPLE 56

Pivaloyloxymethyl 6-(2-Carboxy-2-phenylacetamido)-1-hydroxy-2-methylcarbapenam-3-carboxylate By the method of Example 34, pivaloyloxymethyl 6-(2-benzhydryloxycarbonyl-2-phenylacetamido)-1-hydroxy-2-methylcarbapenam-3-carboxylate is hydrogenolyzed to pivaloyloxymethyl 6-(2-carboxy-2-phenylacetamido)-1-hydroxy-2-methylcarbapenam-3-carboxylate.

By the same method, the corresponding benzyl and 2-naphthylmethyl esters of Example 55 are converted to the same product.

EXAMPLE 57

Pivaloyloxymethyl 1-Acetoxy-6-(2-benzhydryloxycarbonyl-2-phenylacetamido)-2-methylcarbapenam-3-carboxylate By the method of Examples 9, 19, 23, etc., pivaloyloxymethyl 6-(2-benzhydryloxycarbonyl-2-phenylacetamido)-1-hydroxy-2-methylcarbapenam-3-carboxylate is acetylated to provide pivaloyloxymethyl 1-acetoxy-6-(2-benzhydryloxycarbonyl-2-phenylacetamido)-2-methylcarbapenam-3-carboxylate.

By the same method the other hydroxy esters of Example 56 are converted to the corresponding pivaloyloxymethyl 1-acetoxy-6-(2-benzyloxycarbonyl-2-phenylacetamido)-2-methylcarbapenam-3-carboxylate and 1-acetoxy-2-methyl-6-[2-(2-naphthylmethoxycarbonyl)-2-phenylacetamido]carbapenam-3-carboxylate.

EXAMPLE 58

Pivaloyloxymethyl 1-Acetoxy-6-(2-carboxy-2-phenylacetamido)-2-methylcarbapenam-3-carboxylate By the method of Example 34, pivaloyloxymethyl 1-acetoxy-6-(2-benzhydryloxycarbonyl-2-phenylacetamido)-2-methylcarbapenam-3-carboxylate is hydrogenolyzed to pivaloyloxymethyl 1-acetoxy-6-(2-carboxy-2-phenylacetamido)-2-methylcarbapenam-3-carboxylate.

By the same method the corresponding benzyl and 2-naphthylmethyl esters of Example 57 are converted to the same product.

EXAMPLE 59

Benzhydryl 6-(2-Benzhydryloxycarbonyl-2-phenylacetamido)-2-methyl-1-oxocarbapen-2-em-3-carboxylate By the method of Examples 1, 6, 11, 15, etc., benzhydryl 7-(2-benzhydryloxycarbonyl-2-phenylacetamido)-2-diazo-3-methyl-1-beta-oxoceph-3-em-4-carboxylate is rearranged to benzhydryl 6-(2-benzhydryloxycarbonyl-2-phenylacetamido)-2-methyl-1-oxocarbapenam-2-em-carboxylate.

By the same method the other diesters of Preparation 58 are converted to the corresponding benzhydryl, benzyl and 2-naphthylmethyl 6-(2-benzhydryloxycarbonyl-2-phenylacetamido)-2-methyl-1-oxocarbapen-2-em-3-carboxylates, 6-(2-benzyloxycarbonyl-2-phenylacetamido)-2-methyl-1-oxocarbapen-2-em-3-carboxylates and 2-methyl-6-[2-(2-naphthylmethoxycarbonyl)-2-phenylacetamido]-1-oxocarbapen-2-em-3-carboxylates.

EXAMPLE 60

Benzhydryl 6-(2-Benzhydryloxycarbonyl-2-phenylacetamido)-2-methyl-1-oxocarbapenam-3-carboxylate By the method of Examples 2, 7, 17, 21, etc., benzhydryl 6-(2-benzhydryloxycarbonyl-2-phenylacetamido)-2-methyl-1-oxocarbapen-2-em-3-carboxylate is reduced to benzhydryl 6-(2-benzhydryloxycarbonyl-2-phenylacetamido)-2-methyl-1-oxocarbapenam-3-carboxylate.

By the same method the other carbapen-2-em esters of Example 59 are converted to the corresponding benzhydryl, benzyl and 2-naphthylmethyl 6-(2-benzhydryloxycarbonyl-2-phenyl)-2-methyl-1-oxocarbapenam-3-carboxylates, 6-(2-benzyloxycarbonyl-2-phenylacetamido)-2-methyl-1-oxocarbapenam-3-carboxylates and 2-methyl-6-[2-(2-naphthylmethoxycarbonyl-2-phenylacetamido]-1-oxocarbapenam-3-carboxylates.

EXAMPLE 61

6-(2-Carboxy-2-phenylacetamido)-2-methyl-1-oxocarbapenam-3-carboxylic Acid

By the method of Example 34, both ester groups of benzhydryl 6-(2-benzhydryloxycarbonyl-2-phenylacetamido)-2-methyl-1-oxocarbapenam-3-carboxylate are hydrogenolyzed, yielding 6-(2-carboxy-2-phenylacetamido)-2-methyl-1-oxocarbapenam-3-carboxylate.

By the same method, the other benzhydryl, benzyl and 2-naphthylmethyl diesters of Example 60 are converted to the same product.

EXAMPLE 62

Benzhydryl 6-(2-Benzhydryloxycarbonyl-2-phenylacetamido)-1-hydroxy-2-methylcarbapenam-3-carboxylate By the method of Examples 3, 8, 18, 22, etc., benzhydryl 6-(2-benzhydryloxycarbonyl-2-phenylacetamido)-2-methyl-1-oxocarbapenam-3-carboxylate is reduced to benzhydryl-6-(2-benzhydryloxycarbonyl-2-phenylacetamido)-1-hydroxy-2-methylcarbapenam-3-carboxylate.

By the same method the other oxocarbapenams of Example 61 are converted to the corresponding benzhydryl, benzyl and 2-naphthylmethyl 6-(2-benzhydryloxycarbonyl-2-phenylacetamido)-1-hydroxy-2-methylcarbapenam-3-carboxylates, 6-(2-benzyloxycarbonyl-2-phenylacetamido)-1-hydroxy-2-methylcarbapenam-3-carboxylates and 1-hydroxy-2-methyl-6-[2-(2-naphthylmethoxycarbonyl)-2-phenylacetamido]carbapenam-3-carboxylates.

EXAMPLE 63

6-(2-Carboxy-2-phenylacetamido)-1-hydroxy-2-methylcarbapenam-3-carboxylic Acid

By the method of Example 34, the ester groups of benzhydryl 6-(2-benzhydryloxycarbonyl-2-phenylacetamido)-1-hydroxy-2-methylcarbapenam-3-carboxylate are hydrogenolyzed to yield 6-(2-carboxy-2-phenylacetamido)-1-hydroxy-2-methylcarbapenam-3-carboxylic acid.

EXAMPLE 64

Benzhydryl 1-Acetoxy-6-(2-benzhydryloxycarbonyl-2-phenylacetamido)-2-methylcarbapenam-3-carboxylate By the method of Examples 9, 19, 23, etc., benzhydryl 6-(2-benzhydryloxycarbonyl-2-phenylacetamido)-1-hydroxy-2-methylcarbapenam-3-carboxylate is acetylated, affording benzhydryl 1-acetoxy-6-(2-benzhydryloxycarbonyl-2-phenylacetamido)-2-methylcarbapenam-3-carboxylate.

By the same method the other hydroxycarbapenams of Example 62 are converted to the corresponding benzhydryl, benzyl and 2-naphthylmethyl 1-acetoxy-6-(2-benzhydryloxycarbonyl-2-phenylacetamido)-2-methylcarbapenam-3-carboxylates, 1-acetoxy-6-(2-benzyloxycarbonyl-2-phenylacetamido)-2-methylcarbapenam-3-carboxylates and 1-acetoxy-2-methyl-6-[2-(2-naphthylmethoxycarbonyl)-2-phenylacetamido]carbapenam-3-carboxylates.

EXAMPLE 65

1-Acetoxy-6-(2-carboxy-2-phenylacetamido)-2-methylcarbapenam-3-carboxylic Acid

By the method of Example 34, the benzhydryl ester groups of benzhydryl 1-acetoxy-6-(2-benzhydryloxycarbonyl-2-phenylacetamido)-2-methylcarbapenam-3-carboxylate are hydrogenolyzed, yielding 1-acetoxy-6-(2-carboxy-2-phenylacetamido)-2-methylcarbapenam-3-carboxylic acid.

By the same method the other benzhydryl, benzyl and 2-naphthylmethyl derivatives of Example 64 are converted to the same product.

EXAMPLE 66

Pivaloyloxymethyl 6-alpha-[1-(p-nitrobenzyloxycarbonyloxy)ethyl]-2-methyl-1-oxocarbapen-2-em-3-carboxylate By the procedure of Example 1, pivaloyloxymethyl 7-alpha-[1-(p-nitrobenzyloxycarbonyloxy)ethyl]-2-diazo-3-methyl-1-beta-oxoceph-3-em-4-carboxylate (120 mg.) was irradiated for 41 minutes in 120 ml. of methylene chloride at $-55°$ C. Evaporation to dryness gave pivaloyloxymethyl 6-alpha-[1-(p-nitrobenzyloxy)ethyl]-2-methyl-1-oxocarbapen-2-em-3-carboxylate in quantitative yield [ir ($CH_2Cl_2$) 1810 $cm^{-1}$].

By the same method pivaloyloxymethyl 7-alpha-(p-nitrobenzyloxycarbonyloxymethyl)-2-diazo-3-methyl-1-beta-oxoceph-3-em-4-carboxylate is rearranged to pivaloyloxymethyl 6-alpha-(p-nitrobenzyloxycarbonyloxymethyl)-3-methyl-1-oxocarbapen-2-em-3-carboxylate;

pivaloyloxymethyl 7-alpha-(1-acetoxyethyl)-2-diazo-3-methyl-1-beta-oxoceph-3-em-4-carboxylate and pivaloyloxymethyl 7-alpha-(1-acetoxyethyl)-2-diazo-3-methyl-1-alpha-oxoceph-3-em-4-carboxylate are rearranged to pivaloyloxymethyl 6-alpha-(1-acetoxyethyl)-2-methyl-1-oxocarbapen-2-em-3-carboxylate;

pivaloyloxymethyl 7-alpha-(acetoxymethyl)-2-diazo-3-methyl-1-beta-oxoceph-3-em-4-carboxylate and pivaloyloxymethyl 7-alpha-(acetoxymethyl)-2-diazo-1-alpha-oxoceph-3-em-4-carboxylate are rearranged to pivaloyloxymethyl 6-alpha-(acetoxymethyl)-2-methyl-1-oxocarbapen-2-em-3-carboxylate;

pivaloyloxymethyl 7-alpha-(2-acetoxy-2-propyl)-2-diazo-3-methyl-1-beta-oxoceph-3-em-4-carboxylate is rearranged to pivaloyloxymethyl 6-alpha-(2-acetoxy-2-propyl)-2-methyl-1-oxocarbapen-2-em-3-carboxylate; and pivaloyloxymethyl 7-alpha-(1-benzyloxycarbonyloxyethyl)-2-diazo-3-methyl-1-beta-oxoceph-3-em-4-carboxylate is rearranged to pivaloyloxymethyl 6-alpha-(1-benzyloxycarbonyloxyethyl)-2-methyl-1-oxocarbapen-2-em-3-carboxylate.

EXAMPLE 67

Pivaloyloxymethyl 6-alpha-[1-(p-Nitrobenzyloxycarbonyloxy)ethyl]-1-hydroxy-2-methylcarbapen-2-em-3-carboxylate By the procedure of Example 4, the freshly prepared pivaloyloxymethyl 6-alpha-[1-(p-nitrobenzyloxycarbonyloxy)ethyl]-2-methyl-1-oxocarbapen-2-em-3-carboxylate of the preceding Example was reduced to pivaloyloxymethyl 6-alpha-[1-(p-nitrobenzyloxycarbonyloxy)ethyl]-1-hydroxy-2-methylcarbapen-2-em-3-carboxylate. The crude product was chromatographed on silica gel with 20:1 chloroform:ethyl acetate as eluant and tlc monitoring; yield: 62.5 mg.; $R_f$ 0.25 (4:1 chloroform:ethyl acetate); $R_f$ 0.75 (ethyl acetate).

By the same method other 1-oxocarbapen-2-ems of the preceding Example are converted to:

pivaloyloxymethyl 6-alpha-(p-nitrobenzyloxycarbonyloxymethyl)-1-hydroxy-2-methylcarbapen-2-em-3-carboxylate;

pivaloyloxymethyl 6-alpha-(1-acetoxyethyl)-1-hydroxy-2-methylcarbapen-2-em-3-carboxylate;

pivaloyloxymethyl 6-alpha-(acetoxymethyl)-1-hydroxy-2-methylcarbapen-2-em-3-carboxylate;

6-alpha-(1-benzyloxycarbonyloxyethyl)-1-hydroxy-2-methylcarbapen-2-em-3-carboxylate.

EXAMPLE 68

Pivaloyloxymethyl 6-alpha-(1-Hydroxymethyl)-1-hydroxy-2-methylcarbapen-2-em-3-carboxylate By the procedure of Example 10, freshly prepared pivaloyloxymethyl 6-alpha-[1-(p-nitrobenzyloxycarbonyloxy)ethyl]-1-hydroxy-2-methylcarbapen-2-em-3-carboxylate (62.6 g.) was hydrogenolyzed over 30 mg. of 5% Pd/C to yield, after silica gel chromatography with ethyl acetate as eluant, purified pivaloyloxymethyl 6-alpha-(1-hydroxyethyl)-1-hydroxy-2-methylcarbapen-2-em-3-carboxylate [21.1 mg.; $R_f$ 0.6 (ethyl acetate); $R_f$ 0.0 (4:1 chloroform: ethyl acetate)].

By the same method, pivaloyloxymethyl 6-alpha-(1-benzyloxycarbonyloxyethyl)-1-hydroxy-2-methylcarbapen-2-em-3-carboxylate is converted to the same product, pivaloyloxymethyl 6-alpha-(p-nitrobenzyloxycarbonyloxymethyl)-1-hydroxy-2-methylcarbapen-2-em-3-carboxylate is converted to pivaloyloxymethyl 6-alpha-(hydroxymethyl)-1-hydroxy-2-methylcarbapen-2-em-3-carboxylate; and pivaloyloxymethyl 6-alpha-[1-(p-nitrobenzyloxycarbonyloxy)ethyl]-2-methyl-1-oxocarbapen-2-em-3-carboxylate is converted to pivaloyloxymethyl 6-alpha-(1-hydroxyethyl)-2-methyl-1-oxocarbapen-2-em-3-carboxylate.

EXAMPLE 69

Pivaloyloxymethyl 6-(1-Acetoxyethyl)-2-methyl-1-oxocarbapenam-3-carboxylate

Method A

By the method of Examples 2, 7, 17, 21, etc., pivaloyloxymethyl 6-(1-acetoxyethyl)-2-methyl-1-oxocarbapen-2-em-3-carboxylate (Example 66) is reduced to pivaloyloxymethyl 6-(1-acetoxyethyl)-2-methyl-1-oxocarbapenam-3-carboxylate.

By the same method, other esters of Example 66, as appropriate, are converted to:

pivaloyloxymethyl 6-alpha-(1-benzyloxycarbonyloxyethyl)-2-methyl-1-oxocarbapenam-3-carboxylate;

pivaloyloxymethyl 6-alpha-(acetoxymethyl)-2-methyl-1-oxocarbapenam-3-carboxylate; and pivaloyloxymethyl 6-alpha-(2-acetoxy-2-propyl)-2-methyl-1-oxocarbapenam-3-carboxylate.

Method B

Sodium 6-(1-acetoxyethyl)-2-methyl-1-oxocarbapenam-3-carboxylate (Example 80) is dissolved in water, the pH adjusted to approximately 2.0 and the free acid extracted into methylene chloride. Following the method of Preparations 1, 12, 15, 21, etc.,the free acid is esterified to form pivaloyloxymethyl 6-(1-acetoxyethyl)-2-methyl-1-oxocarbapenam-3-carboxylate.

By the same method, but substituting an equivalent amount of bromomethyl acetate, 1,3-dihydro-3-oxobenzo[c]furan-1-yl bromide or 1-ethoxycarbonyloxyethyl chloride, as appropriate, the following esters are prepared: acetoxymethyl, 1,3-dihydro-3-oxobenzo[c]furan-1-yl and 1-ethoxycarbonyloxyethyl 6-(1-acetoxyethyl)-2-methyl-1-oxocarbapenam-3-carboxylates.

EXAMPLE 70

Pivaloyloxymethyl 6-(1-Acetoxyethyl)-1-hydroxy-2-methylcarbapenam-3-carboxylate

Method A

By the method of Examples 3, 8, 18, 22, etc., pivaloyloxymethyl 6-(1-acetoxyethyl)-2-methyl-1-oxocarbapenam-3-carboxylate is reduced to pivaloyloxymethyl 6-(1-acetoxyethyl)-1-hydroxy-2-methylcarbapenam-3-carboxylate.

By the same method the other esters of Example 69 are converted to the corresponding acetoxymethyl, 1,3-dihydro-3-oxobenzo[c]furan-1-yl and 1-ethoxycarbonyloxyethyl 6-alpha-(1-acetoxyethyl)--hydroxy-2-methylcarbapenam-3-carboxylates; and pivaloyloxymethyl 6-alpha-(1-benzyloxycarbonyloxyethyl)-1-hydroxy-2-methylcarbapenam-3-carboxylate;

6-alpha-(acetoxymethyl)-1-hydroxy-2-methylcarbapenam-3-carboxylate and 6-alpha-(2-acetoxy-2-propyl)-1-hydroxy-2-methylcarbapenam-3-carboxylate.

Method B

By method B of Example 69 sodium 6-(1-acetoxyethyl)-1-hydroxy-2-methylcarbapenam-3-carboxylate (Example 81) is converted to pivaloyloxymethyl 6-(1-acetoxyethyl)-1-hydroxy-2-methylcarbapenam-3-carboxylate.

EXAMPLE 71

Pivaloyloxymethyl 6-alpha-(1-Hydroxyethyl)-1-hydroxy-2-methylcarbapenam-3-carboxylate By the method of Example 68, pivaloyloxymethyl 6-alpha-(1-benzyloxycarbonyloxyethyl)-1-hydroxy-2-methylcarbapenam-3-carboxylate is hydrogenolyzed to pivaloyloxymethyl 6-alpha-(1-hydroxyethyl)-1-hydroxy-2-methylcarbapenam-3-carboxylate.

EXAMPLE 72

Benzyl 6-alpha-[1-(p-Nitrobenzyloxycarbonyloxy)ethyl]-2-methyl-1-oxocarbapen-2-em-3-carboxylate By the method of Example 1, using an irradiation time of 31 minutes and without Raney nickel treatment, benzyl 7-alpha-[1-(p-nitrobenzyloxycarbonyloxy)ethyl]-2-diazo-3-methyl-1-beta-oxoceph-3-em-4-carboxylate (100 mg.) was converted to benzyl 6-alpha-[1-(p-nitrobenzyloxycarbonyloxy)ethyl]-2-methyl-1-oxocarbapen-2-em-3-carboxylate in essentially quantitative yield; ir (CH$_2$Cl$_2$) 1810 cm$^{-1}$.

By the same method, benzyl 6-alpha-[1-(p-nitrobenzyloxycarbonyloxy)propyl]-2-diazo-3-methyl-1-beta-oxoceph-3-em-4-carboxylate is rearranged to benzyl 6-alpha-[1-(p-nitrobenzyloxycarbonyloxy)-1-propyl]-2-methyl-1-oxocarbapen-2-em-3-carboxylate.

EXAMPLE 73

Benzyl 6-alpha-[1-(p-Nitrobenzyloxycarbonyloxy)ethyl]-1-hydroxy-2-methylcarbapen-2-em-3-carboxylate By the procedure of Example 4, the freshly prepared benzyl 6-alpha-[1-(p-nitrobenzyloxycarbonyloxy)ethyl]-2-methyl-1-oxocarbapen-2-em-3-carboxylate of the preceding Example was reduced to benzyl 6-alpha-[1-(p-nitrobenzyloxycarbonyloxy)ethyl]-1-hydroxy-2-methylcarbapen-2-em-3-carboxylate, chromatographed on 5 g. of silica gel with 20:1 chloroform:ethyl acetate as eluant; yield 52.2 mg., R$_f$ 0.5 (3:1 chloroform:ethyl acetate).

By the same procedure benzyl 6-alpha-[1-(p-nitrobenzyloxycarbonyloxy)-1-propyl]-2-methyl-oxocarbapen-2-em-3-carboxylate is reduced to benzyl 6-alpha-[1-(p-nitrobenzyloxycarbonyloxy)-1-propyl]-1-hydroxy-2-methylcarbapen-2-em-3-carboxylate.

EXAMPLE 74

Benzyl 6-alpha-[1-(p-Nitrobenzyloxycarbonyloxy)ethyl]-1-acetoxy-2-methylcarbapen-2-em-3-carboxylate The two preceding Examples were repeated to the stage at which a dried methylene chloride solution of crude benzyl 6-alpha-[1-(p-nitrobenzyloxycarbonyloxy)ethyl]-1-hydroxy-2-methylcarbapen-2-em-3-carboxylate was in hand. The latter was cooled to −78° C. and acetic anhydride (18.7 microl.), pyridine (15.8 microl.) and 4-dimethylaminopyridine (4 mg.) were added. After stirring for 1 hour at −78° C., the reaction mixture was extracted with water, dried over anhydrous sodium sulfate, filtered and evaporated to dryness. The residue was chromatographed on silica gel with 10:1 chloroform:ethyl acetate as eluant; yield 32 mg., R$_f$ 0.7 (3:1 chloroform:ethyl acetate).

By the same method, benzyl 6-alpha-[1-(p-nitrobenzyloxycarbonyloxy)-1-propyl]-1-hydroxy-2-methylcarbapen-2-em-3-carboxylate is acetylated to yield benzyl 6-alpha-[1-(p-nitrobenzyloxycarbonyloxy)-1-propyl]-1-acetoxy-2-methylcarbapen-2-em-3-carboxylate.

EXAMPLE 75

Sodium 6-alpha-(1-Hydroxymethyl)-1-hydroxy-2-methylcarbapen-2-em-3-carboxylate

Benzyl 6-alpha-[1-(p-nitrobenzyloxycarbonyloxy)ethyl]-1-hydroxy-2-methylcarbapen-2-em-3-carboxylate (30 mg.) in 6 ml. of tetrahydrofuran and 6 ml. of water was hydrogenolyzed over 150 mg. 5% Pd/C in the presence of 5.1 mg. of sodium bicarbonate according to Example 34. Following catalyst recovery, tetrahydrofuran was removed by vacuum evaporation. The aqueous residue was extracted with ethyl acetate and freeze dried to yield sodium 6-alpha-(1-hydroxyethyl)-1-hydroxy-3-methylcarbapen-2-em-3-carboxylate [20 mg.; $R_f$ 0.9 (9:1 acetone:water); $R_f$ 0.0 (4:1 chloroform:ethyl acetate)].

By the same method benzyl 6-alpha-[1-(p-nitrobenzyloxycarbonyloxy)-1-propyl]-2-methyl-1-hydroxycarbapen-2-em-3-carboxylate is converted to sodium 6-alpha-(1-hydroxy-1-propyl)-1-hydroxy-2-methylcarbapen-2-em-3-carboxylate.

EXAMPLE 76

Sodium 6-alpha-(1-Hydroxyethyl)-1-acetoxy-2-methylcarbapen-2-em-3-carboxylate

By the procedure of the preceding Example, benzyl 6-alpha-[1-p-nitrobenzyloxycarbonyloxy)ethyl]-1-acetoxy-2-methylcarbapen-2-em-3-carboxylate (10 mg.) was converted to sodium 6-alpha-(1-hydroxyethyl)-1-acetoxy-2-methylcarbapen-2-em-3-carboxylate [12 mg.; $R_f$ 0.0 (4:1 chloroform:ethyl acetate); $R_f$ 0.0 (ethyl acetate)].

By the same method 6-alpha-[1-(p-nitrobenzyloxycarbonyloxy)-1-propyl]-1-acetoxy-2-methylcarbapen-2-em-3-carboxylate is hydrogenolyzed to sodium 6-alpha-(1-hydroxy-1-propyl)-1-acetoxy-2-methylcarbapen-2-em-3-carboxylate.

EXAMPLE 77

Benzyl 6-alpha-(1-Acetoxyethyl)-2-methyl-1-oxocarbapen-2-em-3-carboxylate

Method A

By the method of Example 1, benzyl 7-alpha-(1-acetoxyethyl)-2-diazo-3-methyl-1-beta-oxoceph-3-em-4-carboxylate (40 mg.) was irradiated for 34 minutes. Raney nickel (0.4 g.) was added and the mixture stirred at −78° C. for 30 minutes. Raney nickel was recovered by filtration. Evaporation of mother liquor to dryness gave benzyl 6-alpha-(1-acetoxyethyl)-2-methyl-1-oxocarbapen-2-em-3-carboxylate, entirely used without weighing in the next step [ir $(CH_2Cl_2)$ 1805 cm$^{-1}$].

Method B

Method A was repeated on 90 mg. of starting material, omitting the Raney nickel treatment. The same product was obtained in essentially quantitative yield [ir $(CH_2Cl_2)$ 1805 cm$^{-1}$].

By the same methods, benzyl 7-alpha-(1-acetoxy-1-propyl)-2-diazo-3-methyl-1-beta-oxoceph-3-em-4-carboxylate is converted to benzyl 6-alpha-(1-acetoxy-1-propyl)-2-methyl-1-oxocarbapen-2-em-3-carboxylate.

EXAMPLE 78

Benzyl 6-alpha-(1-Acetoxyethyl)-1-hydroxy-2-methylcarbapen-2-em-3-carboxylate

The entire batch of benzyl 6-alpha-(1-acetoxyethyl)-2-methyl-1-oxocarbapen-2-em-3-carboxylate of method A of the preceding Example was taken up in 10 ml. of methylene chloride, cooled to −78° C. and reacted with tetrabutylammonium borohydride according to Example 4 and chromatographed on silica gel with 1:1 chloroform:ethyl acetate as eluant to yield purified benzyl 6-alpha-(1-acetoxyethyl)-1-hydroxy-2-methylcarbapen-2-em-3-carboxylate [21 mg.; pnmr/CDCl$_3$/delta includes 1.5 (d, 3H, J=6), 2.0 (s, 3H) and 5.4 ppm (s, 2H)].

By the same method the corresponding propyl analog of the preceding Example is reduced to benzyl 6-alpha-(1-acetoxy-1-propyl)-1-hydroxy-2-methylcarbapen-2-em-3-carboxylate.

EXAMPLE 79

Benzyl 6-alpha-(1-Acetoxyethyl)-1-acetoxy-2-methylcarbapen-2-em-3-carboxylate

By the method of Example 74, repeating method B of Example 77 and Example 78, a dried solution of crude benzyl 6-alpha-(1-acetoxyethyl)-1-hydroxy-2-methylcarbapen-2-em-3-carboxylate was acetylated to benzyl 6-alpha-(1-acetoxyethyl)-1-acetoxy-2-methylcarbapen-2-em-3-carboxylate, chromatographed on silica gel with 4:1 chloroform:ethyl acetate as eluant; yield 12.7 mg.; pnmr/CDCl$_3$/delta 3.5 ppm (q, 1H).

By the same method the propyl analog of the preceding Example is acetylated to benzyl 6-alpha-(1-acetoxy-1-propyl)-1-acetoxy-2-methylcarbapen-2-em-3-carboxylate.

EXAMPLE 80

Sodium 6-alpha-(1-Acetoxyethyl)-1-hydroxy-2-methylcarbapen-2-em-3-carboxylate

By the procedure of Example 75, benzyl 6-alpha-(1-acetoxy)-1-hydroxy-2-methylcarbapen-2-em-3-carboxylate (5.3 mg.) in 2 ml. of dioxane and 1 ml. water was hydrogenated over 10.6 mg. of 5% Pd/C in the presence of sodium bicarbonate (1.24 mg.). The yield of sodium 6-alpha-(1-acetoxyethyl)-1-hydroxy-2-methylcarbapen-2-em-3-carboxylate was essentially quantitative and the product demonstrated the antimicrobial properties detailed in Table I.

By the same procedure the corresponding propyl analog is converted to sodium 6-alpha-(1-acetoxy-1-propyl)-1-hydroxy-2-methylcarbapen-2-em-3-carboxylate.

EXAMPLE 81

Sodium 6-alpha-(1-Acetoxyethyl)-1-acetoxy-2-methylcarbapen-2-em-3-carboxylate

By the same procedure as the preceding Example, benzyl 6-alpha-(1-acetoxyethyl)-1-acetoxy-2-methylcarbapen-2-em-3-carboxylate (4 mg.) was converted in essentially quantitative yield to sodium 6-alpha-(1- acetoxyethyl)-1-acetoxy-2-methylcarbapen-2-em-3-carboxylate, having the antimicrobial properties detailed in Table I.

By the same procedure, the corresponding propyl analog is converted to sodium 6-alpha-(1-acetoxy-1-propyl)-1-acetoxy-2-methylcarbapen-2-em-3-carboxylate.

EXAMPLE 82

Benzyl 6-alpha-[1-(p-Nitrobenzyloxycarbonyloxy)ethyl]-2-methoxy-1-oxocarbapen-2-em-3-carboxylate By the method of Example 1, benzyl 6-alpha-[1-(p-nitrobenzyloxycarbonyloxy)ethyl]-2-diazo-3-methoxy-1-beta-oxoceph-3-em (31 mg.) in 30 ml. of methylene chloride was irradiated at $-50°$ C. for 10 minutes. Evaporation to dryness in vacuo gave benzyl 6-alpha-[1-(p-nitrobenzyloxycarbonyloxy)ethyl]-2-methoxy-1-oxocarbapen-2-em-3-carboxylate in quantitative yield [ir $(CH_2Cl_2)$ 1810 cm$^{-1}$].

EXAMPLE 83

Benzyl 6-alpha-[1-(p-Nitrobenzyloxycarbonyloxy)ethyl]-1-hydroxy-2-methoxycarbapen-2-em-3-carboxylate By the method of Example 4, the freshly prepared benzyl 6-alpha-[1-(p-nitrobenzyloxycarbonyloxy)ethyl]-2-methyl-1-oxocarbapen-2-em-3-carboxylate of the preceding Example was reduced to benzyl 6-alpha-[1-(p-nitrobenzyloxycarbonyloxy)ethyl]-1-hydroxy-2-methoxycarbapen-2-em-3-carboxylate, chromatographed on silica gel with 100:1 chloroform:ethyl acetate as eluant; yield 5.8 mg.; ir $(CH_2Cl_2)$ 1780 cm$^{-1}$.

EXAMPLE 84

Sodium 6-alpha-(1-Hydroxyethyl)-1-hydroxy-2-methoxycarbapen-2-em-3-carboxylate

By the procedure of Example 75, benzyl 6-alpha(1-hydroxyethyl)-1-hydroxy-2-methoxycarbapen-2-em-3-carboxylate (5.8 mg.) was hydrogenolyzed over 17.4 mg. of 5% Pd/C in 3 ml. of 1:1 dioxane:water in the presence of sodium bicarbonate (1 mg.). Yield of solids 8 mg. containing 2.6 mg. of product. The product demonstrated the antimicrobial properties detailed in Table I.

EXAMPLE 85

Benzyl 6-alpha-[1-(p-Nitrobenzyloxycarbonyloxy)ethyl]-2-mesyloxy-1-oxocarbapen-2-em-3-carboxylate By the method of Examples 1, 6, 11, 15, etc., benzyl 7-alpha-[1-(p-nitrobenzyloxycarbonyloxy)ethyl]-2-diazo-3-mesyl-1-beta-oxoceph-3-em-4-carboxylate is rearranged to benzyl 6-alpha-[1-(p-nitrobenzyloxycarbonyloxy)ethyl]-2-mesyloxy-1-oxocarbapen-2-em-3-carboxylate.

EXAMPLE 86

Benzyl 6-alpha-[1-(p-Nitrobenzyloxycarbonyloxy)ethyl]-1-hydroxy-2-mesyloxy-1-oxocarbapen-2-em-3-carboxylate By the method of Example 4, benzyl 6-alpha-[1-(p-nitrobenzyloxycarbonyloxy)ethyl]-2-mesyloxy-1-oxocarbapen-2-em-3-carboxylate is reduced to benzyl 6-alpha-[1-(p-nitrobenzyloxycarbonyloxy)ethyl]-1-hydroxy-2-mesyloxycarbapen-2-em-3-carboxylate.

EXAMPLE 87

Sodium 6-alpha-(1-Hydroxyethyl)-1-hydroxy-2-mesyloxycarbapen-2-em-3-carboxylate

By the method of Example 75, benzyl 6-alpha-[1-(p-nitrobenzyloxycarbonyloxy)ethyl]-1-hydroxy-1-mesyloxycarbapen-2-em-3-carboxylate is hydrogenolyzed to yield sodium 6-alpha-(1-hydroxyethyl)-1-hydroxy-2-mesyloxycarbapen-2-em-3-carboxylate.

EXAMPLE 88

Benzyl 6-alpha-[1-(p-Nitrobenzyloxycarbonyloxy)ethyl]-2-[2-(p-nitrobenzyloxycarbonylamino)ethylthio]-1-oxocarbapen-2-em-3-carboxylate By the method of Examples 1, 6, 11, 15, etc., benzyl 7-alpha-[1-(p-nitrobenzyloxycarbonyloxy)ethyl]-3-[2-(p-nitrobenzyloxycarbonylamino)ethyl]-2-diazo-1-beta-oxoceph-3-em-4-carboxylate is converted to benzyl 6-alpha-[1-(p-nitrobenzyloxycarbonyloxy)ethyl]-2-[2-(p-nitrobenzylamino)ethyl]-1-oxocarbapen-2-em-3-carboxylate.

By the same method the other compounds of Preparation 85 are converted to:

benzyl 6-alpha-[1-(p-nitrobenzyloxycarbonyloxy)ethyl]-2-ethoxy-1-oxocarbapen-2-em-3-carboxylate;

benzyl 6-alpha-[1-(p-nitrobenzyloxycarbonyloxy)ethyl]-2-isopropoxy-1-oxocarbapen-2-em-3-carboxylate, benzyl 6-alpha-[1-(p-nitrobenzyloxycarbonyloxy)ethyl]-2-(2-benzyloxycarbonylaminoethoxy)-1-oxocarbapen-2-em-3-carboxylate;

benzyl 6-alpha-[1-(p-nitrobenzyloxycarbonyloxy)ethyl]-1-oxo-2-propylthiocarbapen-2-em-3-carboxylate, and benzyl 6-alpha-[1-(p-nitrobenzyloxycarbonyloxy)ethyl]-2-(2-acetamidoethylthio)-1-oxocarbapen-2-em-3-carboxylate.

EXAMPLE 89

Benzyl 6-alpha-[1-(p-Nitrobenzyloxycarbonyloxy)ethyl]-2-[2-(p-nitrobenzyloxycarbonylamino)ethylthio]-1-hydroxycarbapen-2-em-3-carboxylate By the method of Example 4, benzyl 6-alpha-[1-(p-nitrobenzyloxycarbonyloxy)ethyl]-2-[2-(p-nitrobenzyloxycarbonylamino)ethylthio]-1-oxocarbapen-2-em-3-carboxylate is reduced to benzyl 6-alpha-[1-(p-nitrobenzyloxycarbonyloxy)ethyl]-2-[2-(p-nitrobenzyloxycarbonylamino)ethylthio]-1-hydroxycarbapen-2-em-3-carboxylate.

By the same method the other oxo compounds of the preceding Example are reduced to:

benzyl 6-alpha-[1-(p-nitrobenzyloxycarbonyloxy)ethyl]-2-ethoxy-1-hydroxycarbapen-2-em-3-carboxylate;

benzyl 6-alpha-[1-(p-nitrobenzyloxycarbonyloxy)ethyl]-2-isopropoxy-1-hydroxycarbapen-2-em-3-carboxylate;

benzyl 6-alpha-[1-(p-nitrobenzyloxycarbonyloxy)ethyl]-2-(2-benzyloxycarbonylaminoethoxy)-1-hydroxycarbapen-2-em-3-carboxylate;

benzyl 6-alpha-[1-(p-nitrobenzyloxycarbonyloxy)ethyl]-1-hydroxy-2-propylthiocarbapen-2-em-3-carboxylate; and benzyl 6-alpha-[1-(p-nitrobenzyloxycarbonyloxy)ethyl]-2-(2-acetamidoethylthio)-1-hydroxycarbapen-2-em-3-carboxylate.

EXAMPLE 90

Sodium 6-alpha-(1-Hydroxyethyl)-2-(2-aminoethyl)-1-hydroxycarbapen-2-em-3-carboxylate By the method of Example 75, benzyl 6-alpha-[1-(p-nitrobenzyloxycarbonyloxy)ethyl]-2-[2-(p-nitrobenzyloxycarbonyloxy)ethylthio]-1-hydroxycarbapen-2-em-3-carboxylate is hydrogenolyzed to yield sodium 6-alpha-(1-hydroxyethyl)-2-(2-aminoethyl)-1-hydroxycarbapen-2-em-3-carboxylate.

By the same method, the other compounds of the preceding Example are hydrogenolyzed to yield:

sodium 6-alpha-(1-hydroxyethyl)-2-ethoxy-1-hydroxycarbapen-2-em-3-carboxylate;

sodium 6-alpha-(1-hydroxyethyl)-2-(2-aminoethoxy)-1-hydroxycarbapen-2-em-3-carboxylate;

sodium 6-alpha-(1-hydroxyethyl)-2-propylthio-1-hydroxycarbapen-2-em-3-carboxylate; and sodium 6-alpha-(1-hydroxyethyl)-2-(2-acetamidoethyl)-1-hydroxycarbapen-2-em-3-carboxylate.

EXAMPLE 91

6-alpha-[1-Hydroxyethyl]-2-(2-amidinoethylthio)-1-hydroxycarbapen-2-em-3-carboxylic Acid A solution of sodium 6-alpha-[1-hydroxyethyl]-2-(2-aminoethyl)-1-hydroxycarbapen-2-em-3-carboxylate (78 mg., 0.25 mmole) in 5 ml. of a 2:1 mixture of 0.05 N phosphate buffer and dimethylformamide is adjusted to pH 9.5 with 2.5 N sodium hydroxide. While stirring at room temperature, ethyl formamidate.HCl, 24 mg., 0.25 mmole is added and the reaction mixture kept at room temperature for 1 hour. The pH of the reaction mixture is adjusted to 6.0 and evaporated to dryness. If desired, the resulting salt contaminated 6-alpha-[1-hydroxyethyl]-2-(2-amidinoethyl)-1-hydroxycarbapen-2-em-3-carboxylic acid is purified by chromatography on silica gel.

By the same method, the other aminoethyl compound of the preceding Example is converted to 6-alpha-(1-hydroxyethyl)-2-(2-amindinoethoxy)-1-hydroxycarbapen-2-em-3-carboxylic acid.

PREPARATION 1

Pivaloyloxymethyl 3-Methylceph-3-em-4-carboxylate

3-Methylceph-3-em-4-carboxylic acid [12.9 g., 65 mmoles; Kemp et al., Tetrahedron Letters, 3785 (1979)] was dissolved in 100 ml. of dimethylformamide. Triethylamine (6.6 g., 65 mmoles) was added (mild exotherm noted) and the mixture stirred for 0.5 hour at room temperature. Potassium bicarbonate (13 g., 130 mmoles) was added and stirring continued for an additional hour. Finally, chloromethyl pivalate (10.8 g., 70 mmoles) was added and the reaction mixture stirred for ca. 16 hours, at which time tlc (silica gel; 4:1 chloroform:ethyl acetate as eluant; detection by alkaline permanganate spray) indicated that reaction was complete. The reaction mixture was poured into 1.5 l. of ether, washed with multiple portions of water, then with 1 N hydrochloric acid, again with water and finally brine, dried over magnesium sulfate and evaporated to dryness in vacuo with methylene chloride chase to yield pivaloyloxymethyl 3-methylceph-3-em-4-carboxylate [15.8 g., 79%; ir (CH$_2$Cl$_2$) 1770, 1750 cm$^{-1}$].

The same method, but substituting an equivalent amount of bromomethyl acetate, 1,3-dihydro-3-oxobenzo[c]furan-1-yl bromide or 1-ethoxycarbonyloxyethyl chloride, as appropriate, is used to prepare the corresponding acetoxymethyl, 1,3-dihydro-3-oxobenzo[c]furan-1-yl and 1-ethoxycarbonyloxyethyl 3-methylceph-3-em-4-carboxylates.

PREPARATION 2

Pivaloyloxymethyl 3-Methyl-1-beta-oxoceph-3-em-4-carboxylate

Pivaloyloxymethyl 3-methyl-3-em-4-carboxylate (15.4 g., 49 mmoles) was dissolved in 1 l. of methylene chloride and cooled to 0° C. While maintaining this temperature, 80% m-chloroperbenzoic acid (10.6 g., 49 mmoles) was added in five equal portions over 1 hour. After addition was complete, reaction was continued until tlc (method and eluant of Preparation 1) indicated that complete conversion to the corresponding alpha- and beta-oxides had occurred (about 0.5 hour). The reaction mixture was washed several times with water, then saturated bicarbonate, again with water and finally with brine, dried over magnesium sulfate and stripped of solvent in vacuo. The resulting product was chromatographed on silica gel (20 parts by weight) with ethyl acetate-10% methanol as eluant to yield pivaloyloxymethyl 3-methyl-1-beta-oxoceph-3-em-4-carboxylate (4.0 g.; tlc: R$_f$0.14 with 4:1 chloroform:ethyl acetate as eluant).

The corresponding 1-alpha-oxide of lower polarity also resulted from the column chromatography, but in less than pure form. The latter compound is purified by rechromatography, using a higher weight of silica gel to weight of solids (e.g. 50 to 1) and somewhat less polar eluant (e.g. ethyl acetate-4% methanol).

By the same method the other esters of Preparation 1 are converted to the corresponding acetoxymethyl, 1,3-dihydro-3-oxobenzo[c]furan-1-yl and 1-ethoxycarbonyloxyethyl 3-methyl-1-beta-oxoceph-3-em-4-carboxylates and 3-methyl-1-alpha-oxoceph-3-em-4-carboxylates.

PREPARATION 3

Pivaloyloxymethyl 2-diazo-3-methyl-1-beta-oxoceph-3-em-4-carboxylate

Pivaloyloxymethyl 3-methyl-1-beta-oxoceph-3-em-4-carboxylate (674 mg., 2.05 mmoles) was dissolved in 75 ml. of methylene chloride and cooled to 0° C. Diisopropylethylamine (397 mg., 3.08 mmoles) and potassium tert-butoxide (345 mg., 3.08 mmoles) were added, followed after a few minutes by picryl azide [1.04 g., 4.1 mmoles; E. Schrader, Ber. 50, 777 (1917)]. After stirring for 30 minutes, ir spectral analysis indicated a strong diazo band to be present. Trifluoroacetic acid (2 equivalents) was added, the mixture filtered, and the filtrate stripped to a gum. The gum was chromatographed on silica gel with 3:1 chloroform:ethyl acetate as eluant to yield pivaloyloxymethyl 2-diazo-3-methyl-1-beta-oxoceph-3-em-4-carboxylate [384 mg.; ir (CH$_2$Cl$_2$) 2080, 1790, 1725 cm$^{-1}$].

By the same method the other 1-beta-oxide esters of Preparation 2 are converted to the corresponding acetoxymethyl, 1,3-dihydro-3-oxobenzo[c]furan-1-yl and 1-ethoxycarbonyloxyethyl 2-diazo-3-methyl-1-beta-oxoceph-3-em-4-carboxylates.

By the same method, except to use the somewhat more vigorous conditions of temperature and time of Preparation 24, the 1-alpha-oxide esters of Preparation 2 are converted to the corresponding pivaloyloxymethyl, acetoxymethyl, 1,3-dihydro-3-oxobenzo[c]furan-1-yl and 1-ethoxycarbonyloxyethyl 2-diazo-3-methyl-1-alpha-oxoceph-3-em-4-carboxylates.

PREPARATION 4

Benzhydryl 3-Methylceph-3-em-4-carboxylate

3-Methylceph-3-em-4-carboxylic acid (7.56 g., 38 mmoles) was dissolved in 100 ml. of methylene chloride. Diphenyldiazomethane (ca. 16.6 g., 85 mmoles) was added dropwise until tlc (4:1 chloroform:ethyl acetate) indicated reaction was complete. The reaction was evaporated to dryness, the residue taken up in 50% aqueous ethyl acetate and the pH adjusted to 2.5. The ethyl acetate layer was separated, washed several times with water, mixed with an equal volume of water and the pH adjusted to 7.8. The ethyl acetate layer was again separated, washed several times with water and then with brine, dried over anhydrous magnesium sulfate, filtered, and evaporated to yield benzhydryl 3-methylceph-3-em-4-carboxylate [11.4 g., 82%; tlc: $R_f$ 0.75 with 4:1 chloroform:ethyl acetate as eluant; ir ($CH_2Cl_2$) 1775, 1725 cm$^{-1}$].

PREPARATION 5

Benzhydryl 3-Methyl-1-beta-oxoceph-3-em-4-carboxylate

Benzhydryl 3-methylceph-3-em-4-carboxylate (11.4 g., 31 mmoles) was oxidized with 85% m-chloroperbenzoic acid (7.0 g., 34 mmoles, the 10% excess being used to drive the reaction to completion) and a mixture of the alpha- and beta-oxides isolated according to the procedures of Preparation 2. Crude product was recrystallized from ethyl acetate, yielding benzhydryl 3-methyl-1-beta-oxoceph-3-em-4-carboxylate [2.63 g., 22%; m.p. 180°–181° C. (dec.); tlc: $R_f$ 0.05 (4:1 chloroform:ethyl acetate eluant)]. The filtrate was evaporated to dryness and chromatographed on silica gel (same eluant) to yield 3-methyl-1-alpha-oxoceph-3-em-4-carboxylate [2.7 g., 22%; m.p. 163°–165° C. (dec.); tlc: $R_f$ 0.15 (same eluant)] and an additional 0.8 g. (7%) of the 1-beta-oxide.

PREPARATION 6

Benzhydryl 2-Diazo-3-methyl-1-beta-oxoceph-3-em-4-carboxylate

Benzhydryl 3-methyl-1-beta-oxoceph-3-em-4-carboxylate (1.5 g., 4 mmoles) in 160 ml. methylene chloride, diisopropylethylamine (568 mg., 4.4 mmoles), potassium tert-butoxide (493 mg., 4.4 mmoles) and picryl azide (2.03 g., 8 mmoles) were reacted following the methods of Preparation 3. The reaction was monitored by tlc (18:1 chloroform:ethyl acetate). After stirring for 1 hour at 0° C., only a trace of starting material remained. Trifluoroacetic acid (2 equivalents) was added, the reaction mixture filtered, and the filtrate stripped to a gum. The residue was triturated several times with ether and the residue dried under high vacuum for 10 minutes. The residue was crystallized from 3:1 methylene chloride:ethyl acetate to yield benzhydryl 2-diazo-3-methyl-1-beta-oxoceph-3-em-4-carboxylate [1 g., 62%; $R_f$ 0.4 (4:1 chloroform:ethyl acetate); ir ($CH_2Cl_2$) 2080, 1805, 1745, 1680 cm$^{-1}$].

In another preparation wherein the product did not crystallize, the crude product was chromatographed on silica gel (3:1 methylene chloride:ethyl acetate as eluant), producing a product in the same yield. The product is alternatively prepared by the similar procedure of Ebbinghaus et al. [J. Org. Chem. 44, 4697 (1979)].

PREPARATION 7

2,2,2-Trichloroethyl 3-Methylceph-3-em-4-carboxylate

3-Methylceph-3-em-4-carboxylic acid (4 g., 20 mmoles) was dissolved in 200 ml. of methylene chloride containing pyridine (2.05 g., 26 mmoles). 2,2,2-Trichloroethanol (3 g., 20 mmoles) was added, followed by dicyclohexylcarbodiimide (4.5 g., 22 mmoles). The reaction mixture was stirred for approximately 16 hours at room temperature. Precipitated solids were removed by filtration and the filtrate evaporated to dryness in vacuo. The residue was taken up in ethyl acetate and reevaporated, the residue triturated with hexane, and filtered to yield 2,2,2-trichloroethyl 3-methylceph-3-em-4-carboxylate [ir ($CH_2Cl_2$) 1775, 1730 cm$^{-1}$].

PREPARATION 8

2,2,2-Trichloroethyl 3-Methyl-1-beta-Oxoceph-3-em-4-carboxylate 2,2,2-Trichloroethyl 3-methylceph-3-em-4-carboxylate (3.1 g., 9 mmoles) in 300 ml. of methylene chloride with 85% m-chloroperbenzoic acid (1.9 g., 9 mmoles) and a mixture of the alpha- and beta-oxides isolated according to the procedures detailed in Preparation 2. Recrystallization of crude product gave 2,2,2-trichloroethyl 3-methyl-1-beta-oxoceph-3-em-4-carboxylate (539 mg., m.p. 166°–170° C.). The filtrate, evaporated to dryness and chromatographed on silica gel (9:1 ethyl acetate:methanol) gave additional 1-beta-oxide [482 mg.; m.p. 169°–170° C.; $R_f$ 0.10 (4:1 chloroform:ethyl acetate)].

PREPARATION 9

2,2,2-Trichloroethyl 2-Diazo-3-methyl-1-beta-oxoceph-3-em-4-carboxylate 2,2,2-Trichloroethyl 3-methyl-1-beta-oxoceph-3-em-4-carboxylate (1.04 g., 3 mmoles) in 75 ml. of methylene chloride, was reacted with diisopropylethylamine, potassium tert-butoxide and picryl azide, using the equivalents and procedures of Preparation 3. Isolation and purification by methods identical to the same Preparation gave 2,2,2-trichloroethyl 2-diazo-3-methyl-1-beta-oxoceph-3-em-4-carboxylate [659 mg., 58%; $R_f$ 0.4 (4:1 chloroform:ethyl acetate); ir ($CH_2Cl_2$) 2080, 1790, 1730 cm$^{-1}$].

PREPARATION 10

7-Bromocephalosporanic Acid

7-Aminocephalosporanic acid (54.4 g., 0.20 mmole) was suspended in a mixture of 1 l. of water and 0.25 L l. of methanol and cooled to 0°−5° C. While stirring and maintaining this temperature range, hydrobromic acid (48%, 338 ml., 0.20 mmole) was added dropwise, followed by the portionwise addition of sodium nitrite (20.7 g., 0.30 ml.) Copious gas evolution was noted. After an additional 60 minutes of stirring at 0°–5° C., the reaction mixture was stripped of methanol in vacuo, and the product extracted with eight 250 ml. portions of chloroform. The chloroform extracts were combined, back-washed with brine, dried over anhydrous sodium sulfate, filtered and the filtrate evaporated in vacuo to yield 7-bromocephalosporanic acid [25.2 g.; pale yellow foam; pnmr (CDCl$_3$/TMS/delta): includes 2.0 (s, 3H); 3.0–4.0 (m, 2H)].

PREPARATION 11

Cephalosporanic Acid

Hydrogenation catalyst (25.2 g. of 5% palladium on calcium carbonate) was prereduced in 25 ml. of water on a Paar shaker. 7-Bromocephalosporanic acid was taken up in a mixture of 50 ml. of tetrahydrofuran and 50 ml. of water and added to the catalyst slurry. The pH was adjusted to 4.5 and the mixture hydrogenated until hydrogen uptake ceased. The catalyst was recovered by filtration on diatomaceous earth and tetrahydrofuran stripped from the filtrate in vacuo. To the aqueous residue an equal volume of ethyl acetate was added and the pH adjusted to 1.5. The ethyl acetate layer was separated and the aqueous layer extracted with four additional portions of ethyl acetate. The ethyl acetate extracts were combined, back-washed with brine, dried over anhydrous sodium sulfate, filtered, and evaporated to dryness in vacuo to yield cephalosporanic acid [13.2 g.; foam; pnmr (CDCl$_3$/TMS/delta): includes 2.0 (s, 3H); 2.5–4.2 (m, 4H)].

PREPARATION 12

Pivaloyloxymethyl Cephalosporanate

Cephalosporanic acid (5.0 g., 19.4 mmoles), dissolved in 50 ml. of dimethylformamide, was reacted with triethylamine (1.96 g., 19.4 mmoles), potassium bicarbonate (3.89 g., 38.9 mmoles) and chloromethyl pivalate (3.21 g., 3.07 ml., 21.4 mmoles) according to the procedures detailed in Preparation 1. After stirring for ca. 16 hours at room temperature, tlc indicated reaction was incomplete. Additional potassium carbonate (1.95 g.) and chloromethyl pivalate (3.21 g.) were added and reaction continued for an additional 6 hours, at which time only a small amount of starting material remained. Isolation also according to Preparation 1 gave pivaloyloxymethyl cephalosporanate [5.31 g.; oil; ir (CH$_2$Cl$_2$) 1775, 1750 cm$^{-1}$; R$_f$ 0.7 (4:1 chloroform:ethyl acetate)].

PREPARATION 13

Pivaloyloxymethyl 1-beta-Oxocephalosporanate

Pivaloyloxymethyl cephalosporanate (5.31 g., 14.3 mmoles) in 50 ml. of chloroform was reacted with 85% m-chloroperbenzoic acid (2.46 g., 12.2 mmoles) at 0° C. for 1 hour. The reaction mixture was filtered, the filtrate washed in sequence with saturated sodium bicarbonate, water and brine, dried over anhydrous sodium sulfate, filtered and the filtrate evaporated in vacuo to yield product as an oil (4.97 g.). The oil was chromatographed on 150 g. of silica gel with 12 ml. fractions of the ethyl acetate eluant collected. Fractions 38–64 were combined and evaporated in vacuo to yield pivaloyloxymethyl 1-alpha-oxocephalosporanate (625 mg.). Fractions 110–183 were combined and evaporated in vacuo to yield pivaloyloxymethyl 1-beta-oxocephalosporanate [984 mg.; ir (CH$_2$Cl$_2$) 1790, 1745 cm$^{-1}$].

PREPARATION 14

Pivaloyloxymethyl 2-Diazo-1-beta-oxocephalosporanate

Following essentially the procedure of Ebbinghaus et al. [J. Org. Chem. 44, 4697 (1979)], pivaloyloxymethyl 1-beta-oxo-2-diazocephalosporanate (120 mg., 0.31 mmoles) was dissolved in 12 ml. of methylene chloride and cooled to −10° C. Picryl azide (158 mg., 62 mmoles) and diisopropylethylamine (80 mg., 62 mmoles) were added and the mixture stirred at −10° C. for 90 minutes, at which time tlc (4:1 chloroform:ethyl acetate) indicated reaction to be complete. The reaction mixture was stripped of solvent in vacuo and chromatographed on silica gel (3:1 methylene chloride:ethyl acetate as eluant) to yield pivaloyloxymethyl 2-diazo-1-beta-oxocephalosporanate [89 mg., 61%; R$_f$ 0.2 (4:1 chloroform: ethyl acetate); ir (CH$_2$Cl$_2$) 1795, 1750 cm$^{-1}$].

PREPARATION 15

Pivaloyloxymethyl 3-Methyl-7-(2-phenoxyacetamido)ceph-3-em-4-carboxylate

3-Methyl-7-(2-phenoxyacetamido)ceph-3-em-4-carboxylic acid (69.6 g., 0.2 mole) was dissolved in 300 ml. of dimethylformamide and reacted in sequence with triethylamine (20.2 g., 0.2 mole), potassium bicarbonate (40 g., 0.4 mole) and chloromethyl pivalate (33 g., 0.22 mole) according to procedures detailed in Preparation B 1. To isolate the product, the reaction mixture was diluted with 3 l. of ether, and the organic solution washed, dried and evaporated to dryness, as detailed in Preparation 1, affording pivaloyloxymethyl 3-methyl-7-(2-phenoxyacetamido)ceph-3-em-4-carboxylate [75.5 g., 82%; ir (CH$_2$Cl$_2$) 1776, 1750, 1685 cm$^{-1}$].

PREPARATION 16

Pivaloyloxymethyl 3-Methyl-1-beta-oxo-7-(2-phenoxyacetamido)ceph-3-em-4-carboxylate Pivaloyloxymethyl 3-methyl-7-(2-phenoxyacetamido)-ceph-3-em-4-carboxylate (76.5 g., 0.16 moles) in 2 l. of methylene chloride, maintained at 0°–5° C., was oxidized with 85% m-chloroperbenzoic acid (32.5 g., 0.16 mole) added in two portions over ca. 1 hour. The reaction was monitored by tlc (method and eluant as Preparation 1). Once reaction was complete, isolation followed procedures detailed in Preparation 2, yielding pivaloyloxymethyl 3-methyl-1-beta-oxo-7-(2-phenoxyacetamido)ceph-3-em-4-carboxylate (41 g., 54%; m.p. 138°–140° C.), of purity such that column chromatography was unnecessary.

PREPARATION 17

Pivaloyloxymethyl 2-Diazo-3-methyl-1-beta-oxo-7-(2-phenoxyacetamido)-ceph-3-em-4-carboxylate Pivaloyloxymethyl 3-methyl-1-beta-oxo-7-(2-phenoxyacetamido)ceph-3-em-4-carboxylate (4.78 g., 10 mmoles) in 400 ml. of methylene chloride was reacted at 0° C. with diisopropylamine (1.9 g., 15 mmoles), potassium tert-butoxide (1.7 g., 15 mmoles) and picryl azide (5.08 g., 20 mmoles) according to procedures detailed in Preparation 3. The reaction was monitored by tlc (method and eluant as in Preparation 1). Thirty minutes after addition of the azide, tlc indicated all starting material was consumed. Crude product, isolated according to Preparation 3, was chromatographed on silica gel (4:1 methylene chloride:ethyl acetate as eluant) to yield pivaloyloxymethyl 2-diazo-3-methyl-1-beta-oxo-7-(2-phenoxyacetamido)ceph-3-em-4-carboxylate [1.5 g., 29%; $R_f$ 0.33 (4:1 chloroform: ethyl acetate; ir (CH$_2$Cl$_2$) 2080, 1800, 1725, 1720, 1690 cm$^{-1}$].

PREPARATION 18

Benzhydryl 3-Methyl-7-(2-phenoxyacetamido)ceph-3-em-4-carboxylate

3-Methyl-7-(2-phenoxyacetamido)ceph-3-em-4-carboxylic acid (17.75 g., 51 mmoles) was dissolved in 100 ml. methylene chloride. Diphenyldiazomethane (ca. 75 mmoles) was added dropwise with stirring until purple color persisted in the reaction mixture. After an additional 30 minutes of stirring at room temperature, the methylene chloride was evaporated in vacuo. The residue was taken up in a mixture of 100 ml. of water and further processed according to Preparation 4 to yield benzhydryl 3-methyl-7-(2-phenoxyacetamido)ceph-3-em-4-carboxylate [5.03 g.; pnmr (CDCl$_3$/TMS/delta): includes 2.0 (s, 3H), 3.2 (m, 2H), 4.5 (s, 2H), 6.9–7.6 (m, 11H)].

PREPARATION 19

Benzhydryl 3-Methyl-1-beta-oxo-7-(2-phenoxyacetamido)ceph-3-em-4-carboxylate Benzhydryl 3-methyl-7-(2-phenoxyacetamido)ceph-3-em-4-carboxylate (18.0 g., 35 mmoles) was dissolved in 100 ml. of chloroform, cooled to 0°–5° C., and 85% m-chloroperbenzoic acid (7.1 g., 35 mmoles) added portionwise. The mixture was warmed to room temperature and stirred for 1 hour, at which time tlc indicated incomplete reaction. Additional 85% m-chloroperbenzoic acid (0.71 g., 3.5 mmoles) was added and stirring continued for 1.5 hours, at which time no starting material was present by tlc. Isolation according to the procedure of Preparation 3 gave benzhydryl 3-methyl-1-beta-oxo-7-(2-phenoxyacetamido)ceph-3-em-4-carboxylate [14.0 g.; pnmr (CDCl$_3$/TMS/delta): includes 2.0 (s, 3H), 3.3 (m, 2H), 6.1 (dd, 1H, J=5, 12)].

PREPARATION 20

Benzhydryl 2-Diazo-3-methyl-1-beta-oxo-7-(2-phenoxyacetamido)-ceph-3-em-4-carboxylate Benzhydryl 3-methyl-1-beta-oxo-7-(2-phenoxyacetamido)ceph-3-em-4-carboxylate (5.3 g., 10 mmoles) in 250 ml. of methylene chloride was reacted with reagents and reagent quantities as in Preparation 17, as detailed in Preparation 3. Thirty minutes after addition of azide, crude product was isolated according to Preparation 3. Chromatography according to Preparation 17 gave benzhydryl 2-diazo-3-methyl-1-beta-oxo-7-(2-phenoxyacetamido)ceph-3-em-4-carboxylate [1.1 to 1.7 g.; ir (CH$_2$Cl$_2$) 2080, 1800, 1700 cm$^{-1}$].

PREPARATION 21

Pivaloyloxymethyl 7-Methoxy-3-methyl-7-(2-phenoxyacetamido)ceph-3-em-4-carboxylate Method A Following a procedure analogous to that of Koppel and Koehler [J. Am. Chem. Soc. 95, 2403 (1973)], phenyl lithium solution (4.76 ml. of 2.1 M in benzene-ether, 10 mmoles) was added to 80 ml. of dry tetrahydrofuran at 0° C. Methanol (8.5 ml.) was added and the solution stirred 2 minutes at 0° C., then cooled to −46° C., at which point pivaloyloxymethyl 3-methyl-7-(2-phenoxyacetamido)ceph-3-em-4-carboxylate (924 mg., 2 mmoles) was added followed, after 1 minute, by tert-butyl hypochlorite (0.286 ml., 2.4 mmoles), and after a further 2 minutes, a mixture of 8.5 ml. of acetic acid and 8.5 ml. of tetrahydrofuran. The reaction mixture was allowed to warm to room temperature, diluted with toluene and evaporated in vacuo to dryness. The residue was taken up in toluene, washed in sequence with 10% aqueous sodium bisulfite, aqueous phosphate buffer (pH 8) and brine, dried over anhydrous magnesium sulfate, filtered and concentrated to dryness in vacuo. The resulting crude product was chromatographed on silica gel using a methylene chloride-ethyl acetate gradient (0–10% ethyl acetate) to yield pivaloyloxymethyl 7-methoxy-3-methyl-7-(2-phenoxyacetamido)ceph-3-em-4-carboxylate [316 mg.; $R_f$ 0.67 (ethyl acetate); ir (CH$_2$Cl$_2$) 1775, 1740, 1690 cm$^{-1}$].

Method B

Method A was repeated, substituting n-butyl lithium (0.65 g., 20 mmoles) for phenyl lithium. The yield from the column was 416 mg. (42%).

PREPARATION 22

Pivaloyloxymethyl 7-Methoxy-3-methyl-1-beta-oxo-7-(2-phenoxyacetamido)ceph-3-em-4-carboxylate According to the method of Preparation 2, pivaloyloxymethyl 7-methoxy-3-methyl-7-(2-phenoxyacetamido)ceph-3-em-4-carboxylate (316 mg., 0.64 mmoles) in 9 ml. of methylene chloride at 0° C. was oxidized with 80% m-chloroperbenzoic acid (138 mg., 0.64 mmoles) added in 10 equal portions over 1 hour. A mixture of alpha- and beta-oxides was isolated according to Preparation 2 and chromatographed on silica gel (3:1 methylene chloride:ethyl acetate) to yield pivaloyloxymethyl 7-methoxy-3-methyl-1-beta-oxo-7-(2-phenoxyacetamido)ceph-3-em-4-carboxylate [52–64 mg., 16–20%; $R_f$ 0.1 (4:1 chloroform:ethyl acetate)] and pivaloyloxymethyl 7-methoxy-3-methyl-1-alpha-oxo-7-(2-phenoxyacetamido)ceph-3-em-4-carboxylate [65–67 mg., 20–21%; $R_f$ 0.2 (4:1 chloroform:ethyl acetate)].

PREPARATION 23

Pivaloyloxymethyl 2-Diazo-7-methoxy-3-methyl-1-beta-oxo-7-(2-phenoxyacetamido)ceph-3-em-4-carboxylate According to methods detailed in Preparation 3, pivaloyloxymethyl 7-methoxy-3-methyl-1-beta-oxo-(2-phenoxyacetamido)ceph-3-em-4-carboxylate (136 mg., 0.27 mmole) in 12 ml. of methylene chloride at −10° C. was reacted with diisopropylethylamine (52 mg., 0.4 mmole), potassium tert-butoxide (45 mg., 0.4 mmole) and picryl azide (136 mg., 0.54 mmole). Maintaining the reaction at −10° C., infrared spectral analysis indicated incomplete conversion to azide 0.5 hour after azide addition, but complete conversion 1 hour thereafter. Crude product was isolated and chromatographed, also according to Preparation 3, to yield 2-diazo-7-methoxy-3-methyl-1-beta-oxo-7-(2-phenoxyacetamido)ceph-3-em-4-carboxylate [65 mg., 45%; ir (CH$_2$Cl) 2080, 1790, 1725, 1690 cm$^{-1}$].

PREPARATION 24

Pivaloyloxymethyl 2-Diazo-7-methoxy-3-methyl-1-alpha-oxo-7-(2-phenoxyacetamido)ceph-3-em-4-carboxylate Following the procedure detailed in Preparation 23, pivaloyloxymethyl 7-methoxy-3-methyl-1-alpha-oxo-(2-phenoxyacetamido)ceph-3-em-4-carboxylate (178 mg., 0.35 mmoles) in 15 ml. of methylene chloride at −10° C. was reacted with diisopropylethylamine (68 mg., 0.525 mmole), potassium tert-butoxide (59 mg., 0.525 mmole) and picryl azide (178 mg., 0.7 mmole). After 1 hour at −10° C., ir spectral analysis indicated appreciable conversion to the diazo compound. The reaction was warmed to room temperature, at which time ir and tlc (4:1 chloroform:ethyl acetate) indicated complete conversion. Isolation and chromatography according to Preparations 3 and 23 gave pivaloyloxymethyl 2-diazo-7-methoxy-3-methyl-1-alpha-oxo-7-(2-phenoxyacetamido)ceph-3-em-4-carboxylate [54 mg., 29%; ir ($CH_2Cl_2$) 2075, 1795, 1750, 1700, 1690 $cm^{-1}$].

PREPARATION 25

3-Methyl-7-[2-phenyl-2-(4-ethyl-2,3-dioxopiperazine-1-carboxamido)acetamido]ceph-3-em-4-carboxylic Acid Cephalexin (696 mg., 2 mmoles) was dissolved in 10 ml. of water at 5° C. by the action of potassium carbonate (304 mg., 2.2 mmoles). Ethyl acetate (5 ml.) was added and then 4-ethyl-2,3-dioxopiperazine-1-carbonyl chloride (450 mg., 2.2 mole) was added over a period of 15 minutes at 0°–5° C. After addition was complete, the reaction mixture was stirred for an additional 30 minutes, at which time the ethyl acetate layer was separated and the aqueous phase washed with an additional portion of ethyl acetate. The aqueous phase was adjusted to 2.5 and the product extracted into several portions of fresh ethyl acetate. The acidic ethyl acetate extracts were combined, back-washed with water, washed with brine, dried over anhydrous magnesium sulfate, evaporated to dryness in vacuo, and the residue crystallized from methylene chloride to yield 3-methyl-7-[2-phenyl-2-(4-ethyl-2,3-dioxopiperazine-1-carboxamido)acetamido]ceph-3-em-4-carboxylic acid (568 mg., m.p. 199°–200° C.).

PREPARATION 26

Pivaloyloxymethyl 3-Methyl-7-[2-phenyl-2-(4-ethyl-2,3-dioxopiperazine-1-carboxamido)acetamido]ceph-3-em-4-carboxylate 3-Methyl-7-[2-phenyl-2-(4-ethyl-2,3-dioxopiperazine-1-carboxamido)acetamido]ceph-3-em-4-carboxylic acid (3.5 g., 6.8 mmoles) in 15 ml. of dry dimethylformamide, triethylamine (0.69 g., 6.8 mmoles), potassium bicarbonate (1.36 g., 13.6 mmoles) and chloromethyl pivalate were both reacted and product isolated according to the procedures of Preparation 1, resulting in pivaloyloxymethyl 3-methyl-7-[2-phenyl-2-(4-ethyl-2,3-dioxopiperazine-1-carboxamido)acetamido]ceph-3-em-4-carboxylate [1.62 g.; $R_f$ 0.48 (ethyl acetate)].

PREPARATION 27

Pivaloyloxymethyl 3-Methyl-1-beta-oxo-7-[2-phenyl-2-(4-ethyl-2,3-dioxopiperazine-1-carboxamido)acetamido]ceph-3-em-4-carboxylate Pivaloyloxymethyl 3-methyl-7-[2-phenyl-2-(4-ethyl-2,3-dioxopiperazine-1-carboxamido)acetamido]ceph-3-em-4-carboxylate was dissolved in 60 ml. of methylene chloride and cooled to 0° C. m-Chloroperbenzoic acid (80%, 720 mg., 3.3 mmoles) was added in 7 equal portions over a period of 1 hour, maintaining the temperature at 0° C. Following the final addition, tlc (ethyl acetate) indicated oxidation was complete. Isolation as detailed in Preparation 2 (chromatography being unnecessary) afforded pivaloyloxymethyl 3-methyl-1-beta-oxo-7-[2-phenyl-2-(4-ethyl-2,3-dioxopiperazine-1-carboxamido)acetamido]ceph-3-em-4-carboxylate [1.5 g., 70%; $R_f$ 0.19 (ethyl acetate)].

PREPARATION 28

Pivaloyloxymethyl 2-Diazo-3-methyl-1-beta-oxo-7-[2-phenyl-2-(4-ethyl-2,3-dioxopiperazine-1-carboxamido)acetamido]ceph-3-em-4-carboxylate Pivaloyl 3-methyl-1-beta-oxo-7-[2-phenyl-2-(4-ethyl-2,3-dioxopiperazine-1-carboxamido)acetamido]ceph-3-em-4-carboxylate (1.3 g., 2 mmoles) in 130 ml. of methylene chloride was reacted with diisopropylethylamine (387 mg., 3 mmoles), potassium tert-butoxide (336 mg., 3 mmoles) and picryl azide, following the procedures detailed in Preparation 3. Isolation of crude product and chromatography on silica gel (ethyl acetate as eluant) afforded pivaloyloxymethyl 2-diazo-3-methyl-1-beta-oxo-7-[2-phenyl-2-(4-ethyl-2,3-dioxopiperazine-1-carboxamido)acetamido]ceph-3-em-4-carboxylate [750 mg.; $R_f$ 0.25 (ethyl acetate)].

PREPARATION 29

2-Naphthylmethyl 3-Methyl-7-[2-phenyl-2-(4-ethyl-2,3-dioxopiperazine-1-carboxamido)acetamido]ceph-3-em-4-carboxylate 3-Methyl-7-[2-phenyl-2-(4-ethyl-2,3-dioxopiperazine-1-carboxamido)acetamido]ceph-3-em-4-carboxylic acid (4.48 g., 8.7 mmoles) was dissolved in 30 ml. of dimethylformamide. Triethylamine (8.79 mg., 8.7 mmoles) was added and the mixture stirred for 30 minutes. Potassium bicarbonate (1.74 g., 17.4 mmoles) was added and stirring continued for 1 hour. Finally sodium iodide (1.3 g., 8.7 mmoles) and 2-(bromomethyl)naphthalene (2.11 g., 9.6 mmoles) were added (a slight exotherm was noted), and the mixture allowed to stir about 16 hours at room temperature. Since tlc (9:1 acetone:water) monitoring of the reaction mixture over the next 8 hours indicated that reaction had ceased prior to complete conversion to the ester, one-tenth quantities of potassium bicarbonate, sodium iodide and 2-(bromomethyl)naphthalene were added and the reaction allowed to proceed for a further 16 hours. The reaction mixture was diluted with 1:1 ethyl acetate:water, and the organic layer was separated and back-washed several times with water. The organic phase was layered with fresh water, the pH lowered to 2.5, and the organic layer separated, washed with several portions of water, washed with brine, dried over anhydrous magnesium sulfate, filtered and evaporated in vacuo to yield 2-naphthylmethyl 3-methyl-7-[2-phenyl-2-(4-ethyl-2,3-dioxopiperazine-1-carboxamido)acetamido]ceph-3-em-4-carboxylate [4.8 g., 84%; $R_f$ 0.39 (ethyl acetate)].

By the method of Preparation 7, 3-methyl-7-[2-phenyl-2-(4-ethyl-2,3-dioxopiperazine-1-carboxamido)acetamido]ceph-3-em-4-carboxylic acid is esterified, yielding the corresponding 2,2,2-trichloroethyl ester; viz. 2,2,2-trichloroethyl 3-methyl-7-[2-phenyl-2-

(4-ethyl-2,3-dioxopiperazine-1-carboxamido)acetamido]ceph-3-em-4-carboxylate.

PREPARATION 30

2-Naphthylmethyl 3-Methyl-1-beta-oxo-7-[2-phenyl-2-(4-ethyl-2,3-dioxopiperazine-1-carboxamido)acetamido]ceph-3-em-4-carboxylate 2-Naphthylmethyl 3-methyl-7-[2-phenyl-2-(4-ethyl-2,3-dioxopiperazine-1-carboxamido)acetamido]ceph-3-em-4-carboxylate (4.8 g., 7.3 mmoles) in 480 ml. of methylene chloride was reacted at 0° C. with 80% m-chloroperbenzoic acid (1.6 g., 7.3 mmoles) added in 5 equal portions over 1 hour. Tlc (ethyl acetate) indicated starting material had been consumed. Isolation according to Preparation 27 afforded 2-naphthylmethyl 3-methyl-1-beta-oxo-7-[2-phenyl-2-(4-ethyl-2,3-dioxopiperazine-1-carboxamido)acetamido]ceph-3-em-4-carboxylate [3.3 g., 67%; $R_f$ 0.13 (ethyl acetate)].

By the same method 2,2,2-trichloroethyl 3-methyl-7-[2-phenyl-(4-ethyl-2,3-dioxopiperazine-1-carboxamido)acetamido]ceph-3-em-4-carboxylate is converted to 2,2,2-trichloroethyl 3-methyl-1-beta-oxo-7-[2-phenyl-2-(4-ethyl-2,3-dioxopiperazine-1-carboxamido)acetamido]ceph-3-em-4-carboxylate.

PREPARATION 31

2-Naphthylmethyl 2-Diazo-3-methyl-1-beta-oxo-7-[2-phenyl-2-(4-ethyl-2,3-dioxopiperazine-1-carboxamido)acetamido]ceph-3-em-4-carboxylate 2-Naphthylmethyl 3-methyl-1-beta-oxo-7-[2-phenyl-2-(4-ethyl-2,3-dioxopiperazine-1-carboxamido)acetamido]ceph-3-em-4-carboxylate (382 mg., 0.57 mmole) in 38 ml. of methylene chloride at −10° C. was reacted with diisopropylethylamine (110 mg., 0.86 mmole), potassium tert-butoxide (96 mg., 0.86 mmole) and picryl azide (290 mg., 1.14 mmoles) according to procedures detailed in Preparation 3. After 0.5 hour at −10° C., ir and tlc (ethyl acetate) analyses indicated conversion was complete. Product was isolated and chromatographed on silica gel (ethyl acetate eluant) according to Preparation 3 to yield 2-naphthylmethyl 2-diazo-3-methyl-1-beta-oxo-7-[2-phenyl-2-(4-ethyl-2,3-dioxopiperazine-1-carboxamido)acetamido]ceph-3-em-4-carboxylate [237 mg., 60%; ir (CH$_2$Cl$_2$) 2080, 1800, 1760, 1740 cm$^{-1}$; $R_f$ 0.25 (ethyl acetate)].

By the same method, 2,2,2-trichloroethyl 3-methyl-1-beta-oxo-7-[2-phenyl-2-(4-ethyl-2,3-dioxopiperazine-1-carboxamido)acetamido]ceph-3-em-4-carboxylate is converted to 2,2,2-trichloroethyl 2-diazo-3-methyl-1-beta-oxo-7-[2-phenyl-2-(4-ethyl-2,3-dioxopiperazine-1-carboxamido)acetamido]ceph-3-em-4-carboxylate.

PREPARATION 32

3-Methyl-7-(5-methyl-3-phenylisoxazole-4-carboxamido)ceph-3-em-4-carboxyic Acid 7-Aminodesacetoxycephalosporanic acid (7-amino-3-methylceph-3-em-4-carboxylic acid; 21.4 g., 0.1 mmole) was dissolved in 800 ml. of water by the action of sodium bicarbonate (27.9 g., 0.33 mmole). The solution was diluted with 800 ml. of acetone, and cooled to 0° C. 5-Methyl-3-phenylisoxazole-4-carbonyl chloride (27.7 g., 0.33 mmole) was added and the reaction mixture stirred for 2 hours at 0° C., then held at refrigerator temperature for approximately 16 hours. The acetone was removed by evaporation in vacuo, the aqueous residue extracted several times with ethyl acetate. Layering the aqueous phase with ethyl acetate and adjusting down to 2.0 precipitated the desired product. Filtration with ethyl acetate wash gave 3-methyl-7-(5-methylphenylisoxazole-4-carboxamido)ceph-3-em-4-carboxylic acid [27.5 g., pnmr (TMS/DMSO-d$_6$) delta: includes 2.0 (s, 3H); 2.4 (s, 3H); 3.4 (m, 2H); 7.2–7.8 (m, 5H)].

PREPARATION 33

Pivaloyloxymethyl 3-Methyl-7-(5-methyl-3-phenylisoxazole-4-carboxamido)ceph-3-em-4-carboxylate 3-Methyl-7-(5-methyl-3-phenylisoxazole-4-carboxamido)ceph-3-em-4-carboxylic acid (25.9 g., 65 mmoles) was dissolved in anhydrous dimethylformamide (150 ml.). Triethylamine (19.7 g., 195 mmoles), potassium bicarbonate (19.5 g., 195 mmoles), sodium iodide (29.3 g., 195 mmoles) and chloromethyl pivalate (29.3 g., 195 mmoles) were added. An exotherm was noted, the temperature rising to approximately 35° C. After stirring for 6 hours at ambient temperature, monitoring by tlc (4:1 chloroform:ethyl acetate) indicated considerable starting material remained. Additional chloromethyl pivalate (8.4 g., 65 mmoles) was added and stirring at ambient temperature continued for 16 hours. Isolation as detailed in Preparation 1 gave pivaloyloxymethyl 3-methyl-7-(5-methyl-3-phenylisoxazole-4-carboxamido)ceph-3-em-4-carboxylate [25.3 g., 76%; $R_f$ 0.8 (4:1 chloroform:ethyl acetate; ir (CH$_2$Cl$_2$) 1780, 1750, 1670 cm$^{-1}$].

PREPARATION 34

Pivaloyloxymethyl 3-Methyl-7-(5-methyl-3-phenylisoxazole-4-carboxamido)-1-beta-oxoceph-3-em-4-carboxylate Pivaloyloxymethyl 3-methyl-7-(5-methyl-3-phenylisoxazole-4-carboxamido)ceph-3-em-4-carboxylate (24.6 g., 48 mmoles) in 1200 ml. of methylene chloride at 0° was reacted with 80% m-chloroperbenzoic acid (10.4 g., 48 mmoles). After 1 hour, isolation according to Preparation 2 (without chromatography) gave pivaloyloxymethyl 3-methyl-7-(5-methyl-3-phenylisoxazole-4-carboxamido)-1-beta-oxoceph-3-em-4-carboxylate [10.9 g., 43%; $R_f$ 0.4 (4:1 chloroform:ethyl acetate)].

PREPARATION 35

Pivaloyloxymethyl 2-Diazo-3-methyl-7-(5-methyl-3-phenylisoxazole-4-carboxamido)-1-beta-oxoceph-3-em-4-carboxylate According to the procedures detailed in Preparation 3, pivaloyloxymethyl 3-methyl-7-(5-methyl-3-phenylisoxazole-4-carboxamido)-1-beta-oxoceph-3-em-4-carboxylate (2.1 g., 4 mmoles) in 200 ml. of methylene chloride at −10° C. was reacted with diisopropylethylamine (774 mg., 6 mmoles), potassium tert-butoxide (672 mg., 6 mmoles) and picryl azide (2.0 g., 8 mmoles), the reaction monitored, and product isolated (except that 3:1 methylene chloride:ethyl acetate was employed as eluant in the silica gel chromatography), affording pivaloyloxymethyl 2-diazo-3-methyl-7-(5-methyl-3-phenylisoxazole-4-carboxamido)-1-beta-oxoceph-3-em-4-carboxylate [1.09 g., 49%; ir (CH$_2$Cl$_2$) 2080, 1800, 1750, 1680 cm$^{-1}$].

PREPARATION 36

7-D-(2-Benzyloxycarbonylamino-2-phenylacetamido)-3-methylceph-3-em-4-carboxylic Acid Cephalexin (3.47 g., 10 mmoles), is dissolved in 250 ml. of dimethylformamide by the action of diisopropylethylamine (2.58 g., 20 mmoles). The solution is cooled to 0° C. and 4-dimethylaminopyridine (0.24 g., 2 mmoles) added. Maintaining the temperature at 0°–5° C., carbobenzoxy chloride (1.78 g., 10.5 mmoles) is added dropwise. The reaction mixture is allowed to warm to room temperature and stirred for 30 minutes. The reaction mixture is evaporated to dryness in vacuo and the residue taken up in 250 ml. of methylene chloride. The methylene chloride solution is layered with an equal volume of water and the pH adjusted to 2. The organic layer is washed with brine, dried over anhydrous sodium sulfate, filtered, and evaporated to dryness in vacuo to yield 7-(2-benzyloxycarbonylamino-2-phenylacetamido)-4-methylceph-3-em-4-carboxylic acid.

PREPARATION 37

Pivaloyloxymethyl 7-D-(2-Benzyloxycarbonylamino-2-phenylacetamido)-3-methylceph-3-em-4-carboxylate By the method of Preparation 1, 12, 15, etc., 7-D-(2-benzyloxycarbonylamino-2-phenylacetamido)-3-methylceph-3-em-4-carboxylic acid is esterified to produce pivaloyloxymethyl 7-D-(2-benzyloxycarbonylamino-2-phenylacetamido)-3-methylceph-3-em-4-carboxylate.

PREPARATION 38

Pivaloyloxymethyl 7-D-(2-Benzyloxycarbonylamino-2-phenylacetamido)-3-methyl-1-beta-oxoceph-3-em-4-carboxylate By the method of Preparation 16, pivaloyloxymethyl 7-D-(2-benzyloxycarbonylamino-2-phenylacetamido)-3-methylceph-3-em-4-carboxylate is oxidized to pivaloyloxymethyl 7-D-(2-benzyloxycarbonylamino-2-phenylacetamido)-3-methyl-1-beta-oxoceph-3-em-4-carboxylate.

PREPARATION 39

Pivaloyloxymethyl 7-D-(2-Benzyloxycarbonylamino-2-phenylacetamido)-2-diazo-3-methyl-1-beta-oxoceph-3-em-4-carboxylate By the method of Preparation 3, 6, 9, etc., pivaloyloxymethyl 7-D-(2-benzyloxycarbonylamino-2-phenylacetamido)-3-methyl-1-beta-oxoceph-3-em-4-carboxylate is converted to pivaloyloxymethyl 7-D-(2-benzyloxycarbonylamino-2-phenylacetamido)-2-diazo-3-methyl-1-beta-oxoceph-3-em-4-carboxylate.

PREPARATION 40

Benzhydryl 7-D-(2-Benzyloxycarbonylamino-2-phenylacetamido)-3-methylceph-3-em-4-carboxylate By the method of Preparation 4, 18, etc., 7-D-(2-benzyloxycarbonylamino-2-phenylacetamido)-3-methylceph-3-em-4-carboxylic acid is esterified, affording benzhydryl 7-D-(2-benzyloxycarbonylamino-2-phenylacetamido)-3-methylceph-3-em-4-carboxylate.

PREPARATION 41

Benzhydryl 7-D-(2-Benzyloxycarbonylamino-2-phenylacetamido)-3-methyl-1-beta-oxoceph-3-em-4-carboxylate By the method of Preparation 16, benzhydryl 7-D-(2-benzyloxycarbonylamino-2-phenylacetamido)-3-methylceph-3-em-4-carboxylate is oxidized to benzhydryl 7-D-(2-benzyloxycarbonylamino-2-phenylacetamido)-3-methyl-1-beta-oxoceph-3-em-4-carboxylate.

PREPARATION 42

Benzhydryl 7-D-(2-Benzyloxycarbonylamino-2-phenylacetamido)-2-diazo-3-methyl-1-beta-oxoceph-3-em-4-carboxylate By the method of Preparation 3, 6, 9, etc., benzhydryl 7-D-(2-benzyloxycarbonylamino-2-phenylacetamido)-3-methyl-1-beta-oxoceph-3-em-4-carboxylate is converted to benzhydryl 7-D-2-benzyloxycarbonylamino-2-phenylacetamido)-2-diazo-3-methyl-1-beta-oxoceph-3-em-4-carboxylate.

PREPARATION 43

2-Phenyl-2-benzhydryloxycarbonylacetyl Chloride

Following the procedure of Goldman et al. (U.S. Pat. No. 3,773,757), phenylmalonic acid (72 g., 0.40 mole), thionyl chloride (52.4 g., 0.44 mole) and dimethylformamide (0.070 ml.) are mixed in diisopropyl ether and refluxed for 2 hours. The resulting solution of phenylmalonic acid-half acid chloride is cooled and stored under an inert atmosphere until use. Following a procedure analogous to that of Goldman et al., benzhydryl alcohol (73.6 g., 0.40 mole) is added to the half-acid chloride solution and the mixture again refluxed for 2 hours. The volume is reduced by half, providing a diisopropylether solution of 2-phenyl-2-benzhydryloxycarbonylacetyl chloride used directly in the next step.

By the same procedure, but substituting an equivalent quantity of benzyl alcohol or 2-naphthylmethanol, the corresponding 2-phenyl-2-benzyloxycarbonylacetyl and 2-(2-naphthylmethoxycarbonyl)-2-phenylacetyl chlorides are prepared.

PREPARATION 44

7-(2-Benzhydryloxycarbonyl-2-phenylacetamido)-3-methylceph-3-em-4-carboxylic Acid Following a procedure analogous to that of Goldman et al. (loc. cit.), 7-aminodesacetoxycephalosporanic acid (7-amino-3-methylceph-3-em-4-carboxylic acid; 74.9 g., 0.35 mole) is dissolved in well-stirred water (200 ml.) by the slow addition of sodium hydroxide (approximately 75 ml. of 4 N) to a pH of 7.5. To this solution is added 200 ml. of acetone. Keeping the temperature at 10° to 15° C., the isopropyl ether solution of 2-phenyl-2-benzhydryloxycarbonylacetyl chloride prepared above is added with continued strong stirring over 3 minutes. The pH is maintained near 6.5 by the addition of 4 N NaOH (about 160 ml.). Organic solvents are removed by evaporation in vacuo. The aqueous layer is diluted with an equal volume of ethyl acetate and the pH adjusted to 2. The ethyl acetate layer is separated, washed with brine, dried over anhydrous sodium sulfate, filtered and evaporated in vacuo to yield 7-(2-benzhydryloxycarbonyl-2-phenylacetamido)-3-methylceph-3-em-4-carboxylic acid.

The same method is used to convert the other acid chlorides of Preparation 43 to the corresponding 7-(2-benzyloxycarbonyl-2-phenylacetamido)-3-methylceph-3-em-4-carboxylic acid and 3-methyl-7-[2-(2-naphthylmethoxycarbonyl)-2-phenylacetamido]ceph-3-em-4-carboxylic acid.

PREPARATION 45

Pivaloyloxymethyl 7-(2-Benzhydryloxycarbonyl-2-phenylacetamido)-3-methylceph-3-em-4-carboxylate By the method of Preparation 1, 12, 15, etc., 7-(2-benzhydryloxycarbonyl-2-phenylacetamido)-3-methylceph-3-em-4-carboxylic acid is esterified, producing pivaloyloxymethyl 7-(2-benzhydryloxycarbonyl-2-phenylacetamido)-3-methylceph-3-em-4-carboxylate.

By the same method, the other acids of Preparation 44 are converted to the corresponding pivaloyloxymethyl 7-(2-benzyloxycarbonyl-2-phenylacetamido)-3-methylceph-3-em-4-carboxylate and 3-methyl-7-[2-(2-naphthylmethoxycarbonyl)-2-phenylacetamido]ceph-3-em-4-carboxylate.

PREPARATION 46

Pivaloyloxymethyl 7-(2-Benzhydryloxycarbonyl-2-phenylacetamido)-3-methyl-1-beta-oxoceph-3-em-4-carboxylate By the method of Preparation 16, pivaloyloxymethyl 7-(2-benzhydryloxycarbonyl-2-phenylacetamido)-3-methylceph-3-em-4-carboxylate is oxidized to pivaloyloxymethyl 7-(2-benzhydryloxycarbonyl-2-phenylacetamido)-3-methyl-1-beta-oxoceph-3-em-4-carboxylate.

By the same method, the other esters of Preparation 45 are oxidized to the corresponding pivaloyloxymethyl 7-(2-benzyloxycarbonyl-2-phenylacetamido)-3-methyl-1-beta-oxoceph-3-em-4-carboxylate and 3-methyl-7-[2-(2-naphthylmethoxycarbonyl)-2-phenylacetamido]-1-beta-oxoceph-3-em-4-carboxylate.

PREPARATION 47

Pivaloyloxymethyl 7-(2-Benzhydryloxycarbonyl-2-phenylacetamido)-2-diazo-3-methyl-1-beta-oxoceph-3-em-4-carboxylate By the method of Preparation 3, 6, 9, etc., pivaloyloxymethyl 7-(2-benzhydryloxycarbonyl-2-phenylacetamido)-3-methyl-1-beta-oxoceph-3-em-4-carboxylate is converted to pivaloyloxymethyl 7-(2-benzhydryloxycarbonyl-2-phenylacetamido)-2-diazo-3-methyl-1-beta-oxoceph-3-em-4-carboxylate.

By the same method the other 1-beta-oxides of Preparation 46 are converted to the corresponding pivaloyloxymethyl 7-(2-benzyloxycarbonyl-2-phenylacetamido)-2-diazo-3-methyl-1-beta-oxoceph-3-em-4-carboxylate and 2-diazo-3-methyl-7-[2-(2-naphthylmethoxycarbonyl)-2-phenylacetamido]-1-beta-oxoceph-3-em-4-carboxylate.

PREPARATION 48

Benzhydryl 7-(2-Benzhydryloxycarbonyl-2-phenylacetamido)-3-methylceph-3-em-4-carboxylate By the method of Preparation 4, 18, etc., 7-(2-benzhydryloxycarbonyl-2-phenylacetamido)-3-methylceph-3-em-4-carboxylic acid is esterified, providing benzhydryl 7-(2-benzhydryloxycarbonyl-2-phenylacetamido)-3-methylceph-3-em-4-carboxylate.

By the same method, the other acids of Preparation 44 are converted to the corresponding benzhydryl 7-(2-benzyloxycarbonyl-2-phenylacetamido)-3-methylceph-3-em-4-carboxylate and 3-methyl-7-[2-(2-naphthylmethoxycarbonyl)-2-phenylacetamido]ceph-3-em-4-carboxylate.

By the method of Preparation 29 (substituting an equivalent quantity of benzyl bromide for 2-bromomethylnaphthalene, when the benzyl ester is desired), the three acids of Preparation 44 are converted to the corresponding benzyl and 2-naphthylmethyl 7-(2-benzhydryloxycarbonyl-2-phenylacetamido)-3-methylceph-3-em-4-carboxylates, 7-(2-benzyloxycarbonyl-2-phenylacetamido)-3-methylceph-3-em-4-carboxylates and 3-methyl-7-[2-(2-naphthylmethoxycarbonyl)-2-phenylacetamido]ceph-3-em-4carboxylates.

PREPARATION 49

Benzhydryl 7-(2-Benzhydryloxycarbonyl-2-phenylacetamido)-3-methyl-1-beta-oxoceph-3-em-4-carboxylate By the method of Preparation 16, benzhydryl 7-(2-benzhydryloxycarbonyl-2-phenylacetamido)-3-methylceph-3-em-4-carboxylate is oxidized to prepare benzhydryl 7-(2-benzhydryloxycarbonyl-2-phenylacetamido)-3-methyl-1-beta-oxoceph-3-em-4-carboxylate.

By the same method the other esters of Preparation 48 are converted to the corresponding benzhydryl, benzyl and 2-naphthylmethyl 7-(2-benzhydryloxycarbonyl-2-phenylacetamido)-3-methyl-1-beta-oxoceph-3-em-4-carboxylates, 7-(2-benzyloxycarbonyl-2-phenylacetamido)-3-methyl-1-beta-oxoceph-3-em-4-carboxylates and 3-methyl-7-[2-(2-naphthylmethoxycarbonyl)-2-phenylacetamido]-1-beta-oxoceph-3-em-4-carboxylates.

PREPARATION 50

Benzhydryl 7-(2-Benzhydryloxycarbonyl-2-phenylacetamido)-2diazo-3-methyl-1-beta-oxoceph-3-em-4-carboxylate By the method of Preparation 3, 6, 9, etc., benzhydryl 7-(2-benzhydryloxycarbonyl-2-phenylacetamido)-3-methyl-1-beta-oxoceph-3-em-4-carboxylate is converted to benzhydryl 7-(2-benzhydryloxycarbonyl-2-phenylacetamido)-2-diazo-3-methyl-1-beta-oxoceph-3-em-4-carboxylate.

By the same procedure the other esters of Preparation 49 are converted to the corresponding benzhydryl, benzyl and 2-naphthylmethyl 7-(2-benzhydryloxycarbonyl-2-phenylacetamido)-2-diazo-3-methyl-1-beta-oxoceph-3-em-4-carboxylates, 7-(2-benzyloxycarbonyl-2-phenylacetamido)-2-diazo-3-methyl-1-beta-oxoceph-3-em-4-carboxylates and 2-diazo-3-methyl-7-[2-(2-naphthylmethoxycarbonyl)-2-phenyl]-1-beta-oxoceph-3-em-4-carboxylates.

PREPARATION 51

Pivaloyloxymethyl 6,6-Dibromopenicillanate 6,6-Dibromopenicillanic acid [Clayton, J. Chem. Soc. C, 2123 (1969); 10 g., 30 mmoles] in 200 ml. of dimethylformamide was reacted with triethylamine (4.17 ml, 30 mmoles), potassium bicarbonate (3.0 g., 30 mmoles) and chloromethyl pivalate (4.3 ml., 30 mmoles). After stirring for 5 hours at room temperature, tlc (18:1 acetone:-water) indicated appreciable starting material. Further portions of chloromethyl pivalate (4.3 ml., 30 mmoles) and potassium bicarbonate (3.0 g., 30 mmoles) were added and the reaction allowed to proceed for an additional 16 hours at room temperature. The reaction mixture was evaporated to dryness in vacuo and the residue chromatographed on silica gel using 30:1 methylene chloride:ethyl acetate as eluant, monitored by tlc and ir analysis. There resulted pivaloyloxymethyl 6,6-dibromopenicillanate [1.73 g.; $R_f$ 0.77 (18:1 acetone:water); ir ($CH_2Cl_2$) 1790, 1750 cm$^{-1}$].

PREPARATION 52

Pivaloyloxymethyl 6-alpha-Bromo-6-beta-(1-hydroxyethyl)penicillanic Acid

Under a nitrogen atmosphere and in a flame dried, 50 ml., 3-necked flask, pivaloyloxymethyl 6,6-dibromopenicillanic acid (1.0 g., 2.33 mmoles) was dissolved in dry, freshly distilled tetrahydrofuran and cooled to $-78°$ C. tert-Butyl magnesium chloride solution (1.03 ml. of 2.7 M, 2.79 mmoles) in ether was added via a syringe and the reaction mixture stirred for 1 hour at $-78°$ C. Acetaldehyde (0.29 ml., 5.23 mmoles) was then added, and the reaction allowed to proceed for an additional hour at $-78°$ C. The reaction mixture was quenched by the addition of acetic acid (0.22 ml., 3.9 mmoles), allowed to warm to room temperature, and evaporated to dryness in vacuo. The residue was distributed between equal volumes of chloroform and water. The aqueous phase was extracted with two fresh portions of chloroform. The chloroform phase and washes were combined, backwashed with water, washed with brine, dried over anhydrous sodium sulfate, filtered and evaporated to dryness to yield pivaloyloxymethyl 6-alpha-bromo-6-beta-(1-hydroxyethyl)-penicillanic acid [1.01 g.; oil; ir ($CH_2Cl_2$) 1775, 1750 cm$^{-1}$].

By the same method, but substituting an equivalent of formaldehyde (as a tetrahydrofuran solution) for acetaldehyde, pivaloyloxymethyl 6,6-dibromopenicillanates is converted to the corresponding pivaloyloxymethyl 6-alpha-bromo-6-beta-(hydroxymethyl)penicillanate. Substituting acetone for acetaldehyde, 6-alpha-bromo-6-beta-(2-hydroxy-2-propyl)penicillanate is obtained.

PREPARATION 53

Pivaloyloxymethyl 6-alpha-(1-Hydroxyethyl)penicillanate

Hydrogenation catalyst (1.01 g. of 10% palladium on carbon) was slurried in 10 ml. of water and prehydrogenated for 10 minutes (50 psig, room temperature). Pivaloyloxymethyl 6-alpha-bromo-6-beta-(1-hydroxyethyl)penicillanate (1.01 g.) in 10 ml. of tetrahydrofuran was added and hydrogenation resumed for 1.5 hours. The catalyst was recovered by filtration, with aqueous tetrahydrofuran wash. The tetrahydrofuran was evaporated in vacuo from the combined filtrate and washes. Product was extracted from the aqueous residue into 4 portions of ethyl acetate, and the ethyl acetate extracts were combined, washed with brine, dried over anhydrous sodium sulfate, filtered and evaporated to yield pivaloyloxymethyl 6-alpha-(1-hydroxyethyl)penicillanate (249 mg.). The catalyst cake was repulped in approximately 100 ml. of tetrahydrofuran, the catalyst recovered by filtration, and the filtrate evaporated in vacuo to yield an additional 278 mg. of the desired product [ir ($CH_2Cl_2$) 1770, 1760 cm$^{-1}$; $R_f$ 0.48 (4:1 chloroform:ethyl acetate)].

By the same method pivaloyloxymethyl 6-alpha-bromo-6-beta-(hydroxymethyl)penicillanate is converted to pivaloyloxymethyl 6-alpha-(hydroxymethyl)-penicillanate and pivaloyloxymethyl 6-alpha-bromo-6-beta-(2-hydroxy-2-propyl)penicillanate is converted to pivaloyloxymethyl 6-alpha-(2-hydroxy-2-propyl)-penicillanate.

PREPARATION 54

Pivaloyloxymethyl 6-alpha-(1-Acetoxyethyl)penicillanate

Pivaloyloxmethyl 6-alpha-(1-hydroxyethyl)penicillanate (468 mg., 1.49 mmoles) and diisopropylethylamine (0.30 ml.) were dissolved in 50 ml. of methylene chloride. The solution was cooled to 0° C., 4-dimethylaminopyridine (18.7 mg.) and acetic anhydride (0.17 ml.) were added, and the reaction mixture stirred for 30 minutes at room temperature, at which time monitoring by tlc indicated acetylation was complete. The reaction mixture was extracted with aqueous buffer (pH 7.0), dried over anhydrous sodium sulfate, filtered and evaporated to yield the desired product. Chromatography (30:1 chloroform:ethyl acetate) afforded purified pivaloyloxymethyl 6-alpha-(1-acetoxyethyl)penicillanate [120 mg.; ir ($CH_2Cl_2$) 1770, 1750 cm$^{-1}$; $R_f$ 0.35 (30:1 chloroform:ethyl acetate); 0.80 (15:1 methylene chloride:ethyl acetate)].

By the same method, the other hydroxy esters of Preparation 53 are acetylated to form pivaloyloxymethyl 6-alpha-(acetoxymethyl)penicillanate and pivaloyloxymethyl 6-alpha-(2-acetoxy-2-propyl)penicillanate.

PREPARATION 55

Pivaloyloxymethyl 6-alpha-(1-Acetoxyethyl)-1-beta-oxopenicillanate

Pivaloyloxymethyl 6-alpha-(1-acetoxyethyl)penicillanate (120 mg., 0.31 mmole) was dissolved in 10 ml. of methylene chloride and cooled to $-78°$ C. m-Chloroperbenzoic acid (85%, 62 mg., 0.31 mmole) was added in three portions over 1 hour. After 2.5 hours stirring at $-78°$ C., monitoring by tlc (15:1 chloroform:ethyl acetate) indicated oxidation was complete. Isolation according to Preparation 2 (chromatography being unnecessary) afforded pivaloyloxymethyl 6-alpha-(1-acetoxyethyl)-1-beta-oxopenicillanate [91 mg.; ir ($CH_2Cl_2$) 1780, 1750 cm$^{-1}$; $R_f$ 0.22 (15:1 methylene chloride:ethyl acetate)].

By the same method the other ester products of Preparation 54 are oxidized to pivaloyloxymethyl 6-alpha-(acetoxymethyl)-1-beta-oxopenicillanate and pivaloyloxymethyl 6-alpha-(2-acetoxy-2-propyl)-1-beta-oxopenicillanate.

PREPARATION 56

Pivaloyloxymethyl 7-alpha-(1-Acetoxyethyl)-3-methylceph-3-em-4-carboxylate

Following a procedure analogous to that of Morris et al. [J. Am. Chem. Soc. 85, 1896 (1973)], pivaloyloxymethyl 6-alpha-(1-acetoxyethyl)-1-beta-oxopenicillanic acid (90.5 mg.) dissolved in 20 ml. of dry dioxane was placed in the flask of a Soxhlet extraction apparatus, under nitrogen, with a 50/50 mixture of 4 A molecular sieves and neutral alumina in the thimble. Pyridine (2 drops) and 80% phosphoric acid (1 drop) were added, and the mixture refluxed for 23 hours. The reaction mixture was evaporated in vacuo to an oil which was taken up in 50/50 methylene chloride/water. A pH of approximately 2.5 was noted. The methylene chloride phase was separated, backwashed with water, diluted with additional water, and the pH adjusted to 7-7.5. The methylene chloride phase was again separated, washed with fresh water and then brine, dried over anhydrous sodium sulfate, filtered and evaporated in vacuo to yield the desired product (61 mg.). Preparative thin layer chromatography (250 micron thickness of silica gel), developed with 30:1 methylene chloride-:ethyl acetate, the main band being extracted into acetone and evaporated to dryness, afforded pivaloyloxymethyl 7-alpha-(1-acetoxyethyl)-3-methylceph-3-em-4-carboxylate [15.6 mg.; ir $(CH_2Cl_2)$ 1770, 1745 $cm^{-1}$].

By the same method the other penicillanates of Preparation 55 are rearranged to the corresponding pivaloyloxymethyl 7-alpha-(acetoxymethyl)-3-methylceph-3-em-4-carboxylate and pivaloyloxymethyl 7-alpha-(2-acetoxy-2-propyl)-3-methylceph-3-em-4-carboxylate.

PREPARATION 57

Pivaloyloxymethyl 7-alpha-(1-Acetoxyethyl)-3-methyl-1-beta-oxoceph-3-em-4-carboxylate By the method of Preparation 55, pivaloyloxymethyl 7-(1-acetoxymethyl)-3-methylceph-3-em-4-carboxylate (15.6 mg., 0.04 mmole) was oxidized and isolated to provide a mixture of pivaloyloxymethyl 7-alpha-(1-acetoxyethyl)-3-methyl-1-beta-oxoceph-3-em-4-carboxylate and pivaloyloxymethyl 7-alpha-(1-acetoxyethyl)-3-methyl-1-alpha-oxoceph-3-em-4-carboxylate [16 mg.; ir $(CH_2Cl_2)$ 1780, 1745 $cm^{-1}$]. These isomers are separated by chromatography, employing the methods of Preparations 54 and 56.

By the same method, the other ceph-3-em-4-carboxylates of Preparation 56 are oxidized to the corresponding alpha- and beta-oxides: pivaloyloxymethyl 7-alpha-(acetoxymethyl)-3-methyl-1-oxoceph-3-em-4-carboxylate and pivaloyloxymethyl 7-alpha-(2-acetoxy-2-propyl)-3-methyl-1-oxoceph-3-em-4-carboxylate.

PREPARATION 58

Pivaloyloxymethyl 7-(1-Acetoxyethyl)-2-diazo-3-methyl-1-beta-oxoceph-3-em-4-carboxylate Method A The mixture of pivaloyloxymethyl 7-alpha-(1-acetoxyethyl)-3-methyl-1-beta-oxoceph-3-em-4-carboxylate and pivaloyloxymethyl 7-alpha-(1-acetoxyethyl)-3-methyl-1-alpha-oxoceph-3-em-4-carboxylate (16 mg., 0.039 mmole) of Preparation 57 was dissolved in 2 ml. of methylene chloride and cooled to −10° C. Diisopropylethylamine (13 microl., 0.078 mmole) and then picryl azide (19.9 mg., 0.078 mmole) were added. The reaction mixture was stirred for 5 hours, maintaining the temperature between 0° and −10° C., at which time ir analysis indicated extensive diazo formation. After holding at refrigerator temperature for about 16 hours, the reaction mixture was evaporated to dryness to yield a mixture of pivaloyloxymethyl 7-(1-acetoxyethyl)-2-diazo-3-methyl-1-beta-oxoceph-3-em-4-carboxylate [ir $(CH_2Cl_2)$ 2080, 1785, 1750 $cm^{-1}$] and unreacted pivaloyloxymethyl 7-alpha-(1-acetoxyethyl)-3-methyl-1-alpha-oxoceph-3-em-4-carboxylate. These compounds are separated by chromatography employing the methods of Preparations 54 and 56.

Method B

Pivaloyloxymethyl 7-alpha-(1-acetoxymethyl)-3-methyl-1-beta-oxoceph-3-em-4-carboxylate (separated from the corresponding alpha-oxide) is converted to the 2-diazo derivative by Method A immediately above, but preferably by the method which also employs potassium tert-butoxide as in Preparations 3, 6, 9, etc. described above. The latter method is also adapted using the somewhat more vigorous conditions of Preparation 24, to the conversion of pivaloyloxymethyl 7-alpha-(1-acetoxymethyl)-3-methyl-1-alpha-oxoceph-3-em-4-carboxylate to pivaloyloxymethyl 7-(1-acetoxymethyl)-2-diazo-3-methyl-1-alpha-oxoceph-3-em-4-carboxylate.

Methods A and B of this Example are employed, as appropriate, to convert the other 1-oxoceph-3-em-4-carboxylates of Preparation 57 to the corresponding 2-diazo derivatives: pivaloyloxymethyl 7-alpha-(1-acetoxymethyl)-3-methyl-1-beta-oxoceph-3-em-4-carboxylate, 7-alpha-(1-acetoxymethyl)-3-methyl-1-alpha-oxoceph-3-em-4-carboxylate, pivaloyloxymethyl 7-alpha-(2-acetoxy-2-propyl)-3-methyl-1-beta-oxoceph-3-em-4-carboxylate and pivaloyloxymethyl 7-alpha-(2-acetoxy-2-propyl)-3-methyl-1-alpha-oxoceph-3-em-4-carboxylate.

PREPARATION 59

Pivaloyloxymethyl 6-alpha-[1-(p-Nitrobenzyloxycarbonyloxy)ethyl]-penicillanate

Pivaloyloxymethyl 6-alpha-(1-hydroxyethyl)penicillanate (3.2 g.) was dissolved in 100 ml. of methylene chloride and cooled to 0° C. Diisopropylamine (2.19 ml.), 4-dimethylaminopyridine (1.28 g.) and 2.5 g. of p-nitrobenzyloxycarbonyl chloride (p-nitrocarbobenzoxy chloride, 2.72 g.) were added. The reaction mixture was stirred for 16 hours at room temperature. The reaction mixture was washed with water, dried over anhydrous sodium sulfate, filtered and evaporated to crude product. The crude was chromatographed on silica gel with 15:1 chloroform:ethyl acetate as eluant to yield purified pivaloyloxymethyl 6-alpha-[1-(p-nitrobenzyloxycarbonyloxy)ethyl]penicillanate [5 g.; $R_f$ 0.75 (4:1 chloroform:ethyl acetate; $R_f$ 0.7 (ether); pnmr/$CDCl_3$/delta includes 1.0 (s, 9H), 1.5 (d, 3H, J=7), 4.2 ppm (s, 1H)].

By the same procedure the other alcohol of Preparation 53 is converted to pivaloyloxymethyl 6-alpha-(p-nitrobenzyloxycarbonyloxymethyl)penicillanate.

Substituting an equivalent amount of benzyloxycarbonyl chloride for p-nitrobenzyloxycarbonyl chloride produces pivaloyloxymethyl 6-alpha-(1-benzyloxycarbonyloxyethyl)penicillanate.

PREPARATION 60

Pivaloyloxymethyl 6-alpha-[1-(p-Nitrobenzyloxycarbonyloxy)ethyl]-1-beta-oxopenicillanate By the procedure of Preparation 2, pivaloyloxymethyl 6-alpha-[1-(p-nitrobenzyl)ethyl]penicillanate (5 g.) was reacted with m-chloroperbenzoic acid (2.2 g.) in 200 ml. of methylene chloride using a 16 hour reaction time at 0° C. The eluant on chromatography was 4:1 chloroform:ethyl acetate. The yield of pivaloyloxymethyl 6-alpha-[1-(p-nitrobenzyloxycarbonyloxy)e- thyl]-1-beta-oxopenicillanate was 2.55 g., R*f* 0.6 (4:1 chloroform:ethyl acetate).

By the same method the other compounds of the preceding Preparation are converted to pivaloyloxymethyl 6-alpha-(p-nitrobenzyloxycarbonyloxymethyl)-1-beta-oxopenicillanate and 6-alpha-(1-benzyloxycarbonyloxyethyl)-1-beta-oxopenicillanate.

PREPARATION 61

Pivaloyloxymethyl
7-alpha-[1-(p-Nitrobenzyloxycarbonyloxy)ethyl]-3-methylceph-3-em-4-carboxylate Pivaloyloxymethyl 6-alpha-[1-(p-nitrobenzyloxycarbonyloxy)ethyl]-1-beta-oxopenicillanate (2.5 g.) in 400 ml. of dioxane, 22 drops of 80% phosphoric acid and 62 drops of pyridine were reacted according to Preparation 56. Chromatography on a silica gel column with 30:1 chloroform:ethyl acetate as eluant and tlc monitoring gave 380 mg. of clean product. Fractions (558 mg.) containing a minor contaminant were chromatographed on a thick layer plate to yield an additional 190 mg. of purified product. The total yield of pivaloyloxymethyl 7-alpha-[1-(p-nitrobenzyloxycarbonyloxy)ethyl]-3-methylceph-3-em-4-carboxylate was 570 mg., pnmr/CDCl$_3$/delta includes 1.5 (d, 3H, J=7), 2.0 (s, 3H), 4.8 ppm (d, 1H, J=2).

By the same method, the other compounds of the preceding Preparation are converted to pivaloyloxymethyl 7-alpha-(p-nitrobenzyloxycarbonyloxymethyl)-3-methylceph-3-em-4-carboxylate and pivaloyloxymethyl 7-alpha-(1-benzyloxycarbonyloxyethyl)-3-methylceph-3-em-4-carboxylate.

PREPARATION 62

Pivaloyloxymethyl
7-alpha-[1-(p-Nitrobenzyloxycarbonyloxy)ethyl]-3-methyl-1-beta-oxoceph-3-em-4-carboxylate Pivaloyloxymethyl 7-alpha-[1-(p-nitrobenzyloxycarbonyloxy)ethyl]-ceph-3-em-4-carboxylate (570 mg.) was dissolved in 75 ml. of methylene chloride. Formic acid (0.30 ml.) and 30% hydrogen peroxide (0.22 ml.) were added and the reaction stirred for 2 days at room temperature. The reaction mixture was extracted with water, dried over anhydrous sodium sulfate, filtered and evaporated in vacuo. The residue was chromatographed on silica gel, using 1:3 chlorform:ethyl acetate as eluant and tlc monitoring. The yield of pivaloyloxymethyl 7-alpha-[1-p-nitrobenzyloxycarbonyloxy)ethyl]-3-methyl-1-beta-oxoceph-3-em-4-carboxylate was 224 mg., R*f* 0.1 (4:1 chloroform:ethyl acetate); ir (CH$_2$Cl$_2$) 1775 cm$^{-1}$.

By the same method the other compounds of the preceding Preparation are converted to pivaloyloxymethyl 7-alpha-(p-nitrobenzyloxycarbonyloxymethyl)-3-methyl-1-beta-oxoceph-3-em-4-carboxylate and pivaloyloxymethyl 7-alpha-(1-benzyloxycarbonyloxyethyl)-3-methyl-1-beta-oxoceph-3-em-4-carboxylate.

PREPARATION 63

Pivaloyloxymethyl
7-alpha-[1-(p-Nitrobenzyloxycarbonyloxy)ethyl]-2-diazo-3-methyl-1-beta-oxoceph-3-em-4-carboxylate By the method of Preparation 58, pivaloyloxymethyl 7-alpha-[1-(p-nitrobenzyloxycarbonyloxy)ethyl]-3-methyl-1-beta-oxoceph-3-em-4-carboxylate (49.8 mg.) was reacted with picryl azide (77.1 mg.) in the presence of diisopropylethylamine (28.8 microl.) in 15 ml. of methylene chloride for 16 hours at −10° to 0° C. Additional reagents (azide, 35 mg. and amine, 10.8 microl.) were added over the next two days. After a total reaction time of 2.3 days, product was isolated according to the same Example and the crude product chromatographed on silica gel using 10:1 chloroform:ethyl acetate as eluant to yield purified pivaloyloxymethyl 7-alpha-[1-(p-nitrobenzyloxycarbonyloxy)ethyl]-2-diazo-3-methyl-1-beta-oxoceph-3-em-4-carboxylate [120 mg.; ir (CH$_2$Cl$_2$) 2080 cm$^{-1}$].

By the same method the other compounds of the preceding Preparation are converted to pivaloyloxymethyl 7-alpha-(p-nitrobenzyloxycarbonyloxymethyl)-2-diazo-3-methyl-1-beta-oxoceph-3-em-4-carboxylate and pivaloyloxymethyl 7-alpha-(1-benzyloxycarbonyloxymethyl)-2-diazo-3-methyl-1-beta-oxoceph-3-em-4-carboxylate.

PREPARATION 64

Benzyl 6,6-Dibromopenicillanate

Dibromopenicillanic acid (50 g., 0.30 mole) was dissolved in 150 ml. of dimethylformamide. The solution was cooled to 0°–5° C., triethylamine (21.3 ml., 0.30 mole) and then benzyl bromide (18.2 ml., 0.30 ml.) were added, and the reaction mixture stirred for 16 hours at room temperature. The reaction mixture was quenched into ice and water and extracted with four portions of ethyl acetate. The combined organic layers were washed in sequence with 0.1 N hydrochloric acid, water and brine, dried over anhydrous sodium sulfate and evaporated to dryness. Crystallization from ether gave benzyl 6,6-dibromopenicillanate (61 g.).

PREPARATION 65

Benzyl
6-alpha-Bromo-6-beta-(1-hydroxyethyl)penicillanic Acid

By the method of Preparation 52, benzyl 6,6-dibromopenicillanic acid (30 g.) was converted to benzyl 6-alpha-bromo-6-beta-(1-hydroxyethyl)penicillanic acid [31.4 g.; oil; pnmr/CDCl$_3$/delta includes 5.2 (s, 2H), 4.5 (s, 1H)].

By the same method, substituting an equivalent of propionaldehyde for acetaldehyde, benzyl 6-alpha-bromo-6-beta-(1-hydroxy-1-propyl)penicillanic acid is prepared.

PREPARATION 66

Benzyl 6-alpha-(1-Hydroxyethyl)penicillanate

By the procedure of Preparation 53, benzyl 6-alpha-bromo-6-beta-(1-hydroxyethyl)penicillanate (31.4 g.) was hydrogenated over 15.7 g. of 5% Pd/CaCO$_3$ in 150 ml. of 2:1 tetrahydrofuran:water, being careful to stop the hydrogenation at the break-point when essentially one molar equivalent of hydrogen had been consumed. The crude product (19.6 g.), isolated as an oil, was chromatographed on 400 mg. of silica gel with 3:2 chloroform:ethyl acetate as eluant. After an initial 500 ml. of eluate, 12 ml. fractions were collected. Fractions 41–70 were combined and evaporated to yield purified benzyl 6-alpha-(1-hydroxyethyl)penicillanate [7.72 g.; pnmr/CDCl$_3$/delta 1.4 (s, 3H), 1.6 (s, 3H), 4.5 (s, 1H), 5.1 (s, 1H), 5.8 (s, 1H), 7.3 ppm (s, 5H)].

By the same method the other bromo ester of the preceding Preparation is converted to benzyl 6-alpha-(1-hydroxy-1-propyl)penicillanate.

PREPARATION 67

Benzyl 6-alpha-[1-(p-Nitrobenzyloxycarbonyloxy)ethyl]-penicillanate

Benzyl 6-alpha-(1-hydroxyethyl)penicillanate (7.7 g., 0.023 mole) was dissolved in 125 ml. of methylene chloride and the solution cooled to 0° C. Diisopropylethylamine (4.8 ml., 0.028 mole), dimethylaminopyridine (2.8 g., 0.023 mole) and p-nitrobenzyl chloroformate (6.0 g., 0.028 mole) were added in sequence and the reaction mixture stirred at room temperature for 16 hours. The reaction mixture was washed sequentially with 100 ml. of 1 N hydrochloric acid, 100 ml. of water, 100 ml. of saturated sodium bicarbonate, 100 ml. of water and 100 ml. of brine, dried over anhydrous sodium sulfate, filtered and evaporated in vacuo to yield crude product. Chromatography on silica gel using 15:1 chloroform:ethyl acetate gave purified benzyl 6-alpha-[1-(p-nitrobenzyloxycarbonyloxy)ethyl]penicillanate [11.1 g.; oil; pnmr/CDCl$_3$/delta includes 4.5 (s, 1H), 5.2 ppm (s, 2H)].

By the same method the other alcohol of the preceding Preparation is converted to benzyl 6-alpha-[1-(p-nitrobenzyloxycarbonyloxy)-1-propyl]penicillanate.

PREPARATION 68

Benzyl 6-alpha-[1-(p-Nitrobenzyloxycarbonyloxy)ethyl]-1-beta-oxopenicillanate Benzyl 6-alpha-[1-(p-nitrobenzyloxycarbonyloxy)ethyl]penicillanate (10.95 g., 0.022 mole) was reacted with m-chloroperbenzoic acid in 400 ml. of methylene chloride by the procedure of Preparation 2, using an initial reaction temperature of −78° C. followed by 16 hours at 0° C. The crude yield was 11.6 g. Silica gel chromatography employing 10:1 chloroform:ethyl acetate as eluant gave purified benzyl 6-alpha-[1-(p-nitrobenzyloxycarbonyloxy)ethyl]-1-beta-oxopenicillanate [4.1 g., ir (CH$_2$Cl$_2$) 1770 cm$^1$].

By the same method the other compound of the preceding Preparation is converted to benzyl 6-alpha-[1-(p-nitrobenzyloxycarbonyloxy)-1-propyl]-1-beta-oxopenicillanate.

PREPARATION 69

Benzyl 7-alpha-[1-(p-Nitrobenzyloxycarbonyloxy)ethyl]-3-methylceph-3-em-4-carboxylate Following the procedure of Preparation 56, benzyl 6-alpha-[1-(p-nitrobenzyloxycarbonyloxy)ethyl]-1-beta-oxopenicillanate was converted to benzyl 7-alpha-[1-(p-nitrobenzyloxycarbonyloxy)ethyl]-3-methylceph-3-em-4-carboxylate, purified by silica gel chromatography employing 30:1 chloroform:ethyl acetate as eluant [1.4 g., pnmr/CDCl$_3$/delta includes 2.0 (s, 3H) and 4.5 ppm (d, 1H, J=2 Hz)].

By the same method the other compound of the preceding Preparation is converted to benzyl 7-alpha-[1-(p-nitrobenzyloxycarbonyloxy)-1-propyl]-3-methylceph-3-em-4-carboxylate.

PREPARATION 70

Benzyl 7-alpha-[1-(p-Nitrobenzyloxycarbonyloxy)ethyl]-3-methyl-1-beta-oxoceph-3-em-4-carboxylate Benzyl 7-alpha-[1-(p-nitrobenzyloxycarbonyloxy)ethyl]-3-methylceph-3-em-4-carboxylate (1.40 g., 2.82 mmoles) was dissolved in 150 ml. of methylene chloride. Formic acid (0.42 ml.) and 30% hydrogen peroxide (0.42 ml., 3.1 mmoles) were added and the reaction mixture was stirred for 2 days. The reaction mixture was extracted with water, dried over anhydrous sodium sulfate, filtered and evaporated to yield a mixture of alpha- and beta-oxides. The mixture was chromatographed on silica gel using 1:3 chloroform:ethyl acetate as eluant. The less polar alpha-oxide eluted first [R$_f$ 0.5 (1:3 chloroform:ethyl acetate)], followed by the more polar beta-oxide (R$_f$ 0.3). Additional beta-oxide was isolated by thick layer chromatography of the middle cuts containing both isomers. The total yield of purified benzyl 7-alpha-[1-(p-nitrobenzyloxycarbonyloxy)ethyl]-3-methyl-1-beta-oxoceph-3-em-4-carboxylate was 509 mg. [ir(CH$_2$Cl$_2$) 1780 cm$^{-1}$].

By the same procedure, the other compound of the preceding Preparation is converted to benzyl 7-alpha-[1-(p-nitrobenzyloxycarbonyloxy)-1-propyl]-3-methyl-1-beta-oxoceph-3-em-4-carboxylate.

PREPARATION 71

Benzyl 7-alpha-[1-(p-Nitrobenzyloxycarbonyloxy)ethyl]-2-diazo-3-methyl-1-beta-oxoceph-3-em-4-carboxylate By the procedure of Preparation 14, benzyl 7-alpha-[1-(p-nitrobenzyloxycarbonyloxy)ethyl]-3-methyl-1-beta-oxoceph-3-em-4-carboxylate (509 mg.) was converted to benzyl 7-alpha-[1-(p-nitrobenzyloxycarbonyloxy)ethyl]-2-diazo-3-methyl-1-beta-oxoceph-3-em-4-carboxylate, purified by chromatography on silica gel with 10:1 chloroform:ethyl acetate as eluant. Yield: 318 mg.; R$_f$ 0.4 (10:1 chloroform:ethyl acetate); ir (CH$_2$Cl$_2$) 1780, 2060 cm$^{-1}$.

By the same procedure the other compound of the preceding Preparation is converted to benzyl 7-alpha-[1-(p-nitrobenzyloxycarbonyloxy)-1-propyl]-2-diazo-3-methyl-1-beta-oxoceph-3-em-4-carboxylate.

PREPARATION 72

Benzyl 6-alpha-(1-Acetoxyethyl)penicillanate

By the procedure of Preparation 54, benzyl 6-alpha-(1-hydroxyethyl)penicillanate (4 g.) was acetylated, using a reaction time 7 hours, to yield, without chromatography, benzyl 6-alpha-(1-acetoxymethyl)penicillanate [3.72 g.; pnmr/CDCl$_3$/delta includes 5.2 (s, 2H) and 7.4 ppm (s, 5H)].

By the same method the other compound of the preceding Preparation is converted to benzyl 6-alpha-(1-acetoxy-1-propyl)penicillanate.

PREPARATION 73

Benzyl 6-alpha-(1-Acetoxyethyl)-1-beta-oxopenicillanate

By the same procedure as Preparation 56, benzyl 6-alpha-(1-acetoxyethyl)penicillanate (3.72 g.) was oxidized to benzyl-6-alpha-(1-acetoxyethyl)-1-beta-oxopenicillanate [3.7 g.; pnmr/CDCl$_3$/delta includes 2.0 ppm (s, 3H)].

PREPARATION 74

Benzyl 7-alpha-(1-Acetoxyethyl)-3-methylceph-3-em-4-carboxylate

By the procedure of Preparation 56, benzyl 6-alpha-(1-acetoxyethyl)-1-beta-oxopenicillanate (3.7 g.) was reacted with pyridine (2.5 ml.) and phosphoric acid (42 drops, 0.84 ml.) in 500 ml. of dioxane, and crude product column chromatographed on silica gel with 10:1 chloroform:ethyl acetate as eluant to yield purified benzyl 7-alpha-(1-acetoxyethyl)-3-methylceph-3-em-4-carboxylate [922 mg.; pnmr/CDCl$_3$/delta includes 1.4 (s, 3H, J=6), 1.9 (s, 3H), 4.5 ppm (d, 1H, J=1)].

By the same method the other compound of the preceding Preparation is converted to benzyl 7-alpha-(1-acetoxy-1-propyl)-3-methylceph-3-em-4-carboxylate.

PREPARATION 75

Benzyl 7-alpha-(1-Acetoxyethyl)-3-methyl-1-beta-oxoceph-3-em-4-carboxylate

By the procedure of Preparation 55, benzyl 7-alpha-(1-acetoxyethyl)-3-methylceph-3-em-4-carboxylate (922 mg.) was oxidized with m-chloroperbenzoic acid in methylene chloride for 20 hours at −78° C. Column chromatography on silica gel gave benzyl 7-alpha-(1-acetoxyethyl)-3-methyl-1-beta-oxoceph-3-em-4-carboxylate [331 mg.; pnmr/CDCl$_3$/delta includes 2.0 (br. s, 6H), 5.2 ppm (s, 2H)] and, separately, the corresponding alpha-oxide (265 mg.).

By the same procedure the other compound of the preceding Example is converted to benzyl 7-alpha-(1-acetoxy-1-propyl)-3-methyl-1-beta-oxoceph-3-em-4-carboxylate.

PREPARATION 76

Benzyl 7-alpha-(1-Acetoxyethyl)-2-diazo-3-methyl-1-beta-oxoceph-3-em-4-carboxylate By the procedure of Preparation 3, benzyl 7-alpha-(1-acetoxyethyl)-3-methyl-1-beta-oxoceph-3-em-4-carboxylate (331 mg.) was converted to benzyl 7-alpha-(1-acetoxyethyl)-2-diazo-3-methyl-1-beta-oxoceph-3-em-4-carboxylate, purified by silica gel chromatography with 1:1 methylene chloride:ethyl acetate as eluant [130 mg.; ir (CHCl$_3$) 2080 cm$^{-1}$].

By the same method the other compound of the preceding Preparation is converted to benzyl 7-alpha-(1-acetoxy-1-propyl)-2-diazo-3-methyl-1-beta-oxoceph-3-em-4-carboxylate.

PREPARATION 77

Benzyl 7-alpha-[1-(p-Nitrobenzyloxycarbonyloxy]-3-methylene-1-beta-oxocepham-4-carboxylate Benzyl 6-alpha-[1-(p-nitrobenzyloxycarbonyloxy)ethyl]-1-beta-oxopenicillanate (1.0 g.) was combined with N-chlorosuccinimide (286 mg.) in 200 ml. of chloroform and refluxed for 16 hours. The reaction mixture was cooled to 0° C. and stannic chloride (SnCl$_4$; 0.24 ml.) added. After 8 hours, the reaction mixture was diluted with ethyl acetate to dissolve precipitated solids, washed in sequence with saturated sodium bicarbonate, water and brine, dried over anhydrous sodium sulfate and evaporated in vacuo. The residue was chromatographed on silica gel with 3:1 chloroform:ethyl acetate as eluant and tlc monitoring. Clean product fractions were combined and evaporated to yield purified benzyl 7-alpha-[1-(p-nitrobenzyloxycarbonyloxy]-3-methylene-1-beta-oxocephem-4-carboxylate [0.51 g.; pnmr/CDCl$_3$/delta includes 1.5 (d, 3H, J=6), 4.7 (br. s., 1H), 5.3 (s, 1H), 5.7 ppm (s, 1H)].

PREPARATION 78

Benzyl 7-alpha-[1-(p-Nitrobenzyloxycarbonyloxy)ethyl]-3-hydroxy-1-beta-oxoceph-3-em-4-carboxylate Benzyl 7-alpha-[1-(p-nitrobenzyloxycarbonyloxy)ethyl]-3-methylene-1-beta-oxocepham-4-carboxylate (491 mg.) was dissolved in 50 ml. of methylene chloride and the solution cooled to −78° C. Ozone was bubbled into the solution for a few minutes until a blue color persisted. The mixture was purged with nitrogen for 10 minutes and then dimethyl sulfide (0.2 ml.) was added. The mixture was warmed to above 0° C., washed with water. The water phase was back-washed with methylene chloride and the two organic layers combined, washed with brine, dried over anhydrous sodium sulfate, filtered and evaporated to yield benzyl 7-alpha-[1-(p-nitrobenzyloxycarbonyloxy)ethyl]-3-hydroxy-1-beta-oxoceph-3-em-4-carboxylate.

PREPARATION 79

Benzyl 7-alpha-[1-(p-Nitrobenzyloxycarbonyloxy)ethyl]-3-methoxy-1-beta-oxoceph-3-em-4-carboxylate Benzyl 7-alpha-[1-(p-nitrobenzyloxycarbonyloxy)ethyl]-3-hydroxy-1-beta-oxoceph-3-em-4-carboxylate (300 mg.) was dissolved in 25 ml. of methylene chloride and cooled to 0° C. Diazomethane (5 equivalents) in ether (30 ml.) was added dropwise and the mixture maintained at 0° C. for 1 hour. Sufficient acetic acid was added to destroy excess diazomethane, and the mixture washed with water, washed with brine, dried over anhydrous sodium sulfate, filtered and evaporated in vacuo. The residue was chromatographed on silica gel using 10:1 chloroform:ethyl acetate as eluant and tlc monitoring to yield purified benzyl 7-alpha-[1-(p-nitrobenzyloxycarbonyloxy)ethyl]-3-methoxy-1-beta-oxoceph-3-em-4-carboxylate [133 mg.; R$_f$ 0.2 (4:1 chloroform:ethyl acetate); pnmr/CDCl$_3$/delta includes 1.4 (d, 3H, J=6), 3.4 (s, 3H), 4.4 ppm (d, 1H, J=2)].

PREPARATION 80

Benzyl 7-alpha-[1-(p-Nitrobenzyloxycarbonyloxy)ethyl]-3-methoxy-1-beta-oxoceph-3-em-4-carboxylate By the procedure of Preparation 14, benzyl 7-alpha-[1-p-nitrobenzyloxycarbonyloxy)ethyl]-3-methoxy-1-beta-oxoceph-3-em-4-carboxylate (134 mg., 0.24 mmole) was converted to benzyl 7-alpha-[1-(p-nitrobenzyloxycarbonyloxy)ethyl]-2-diazo-3-methoxy-1-beta-oxoceph-3-em-4-carboxylate, purified by chromatography on silica gel using 30:1 chloroform:ethyl acetate as eluant. Clean product fractions were combined and evaporated in vacuo to yield 28 mg. of purified product [R$_f$ 0.5 (ethyl acetate), ir (CH$_2$Cl$_2$) 1800, 2090 cm$^{-1}$]. Repeat chromatography of fractions contaminated with more polar impurity (19 mg.) gave an additional 3 mg. of purified product.

PREPARATION 81

Benzyl 7-alpha-[1-(p-Nitrobenzyloxycarbonyloxy)ethyl]-3-mesyloxy-1-beta-oxoceph-3-em-4-carboxylate Benzyl 7-alpha-[1-p-nitrobenzyloxycarbonyloxy)ethyl]-3-hydroxy-1-beta-oxoceph-3-em-4-carboxylate (439 mg.) was dissolved in 60 ml. of methylene chloride and the solution cooled to 0° C. Diisopropylethylamine (0.25 ml.) and mesyl chloride (0.15 ml.) were added and the reaction mixture stirred at 0° C. for 8 hours, then washed with saturated sodium bicarbonate, washed with brine and evaporated to dryness (0.56 g.). The crude was chromatographed on silica gel with 10:1 chloroform: ethyl acetate as eluant to yield purified benzyl 7-alpha-[1-(p-nitrobenzyloxycarbonyloxy)ethyl]-3-mesyloxy-1-beta-oxoceph-3-em-4-carboxylate [0.27 g.; $R_f$ 0.42 (1:1 chloroform:ethyl acetate); pnmr/CDCl$_3$/delta includes 3.1 ppm (s, 3H)].

PREPARATION 82

Benzyl 7-alpha-[1-(p-Nitrobenzyloxycarbonyloxy)ethyl]-2-diazo-3-mesyloxy-1-beta-oxoceph-3-em-4-carboxylate By the method of Preparation 80, benzyl 7-alpha-[1-(p-nitrobenzyloxycarbonyloxy)ethyl]-3-mesyloxy-1-beta-oxoceph-3-em-4-carboxylate is converted to benzyl 7-alpha-[1-(p-nitrobenzyloxycarbonyloxy)ethyl]-2-diazo-3-mesyloxy-1-beta-oxoceph-3-em-4-carboxylate.

PREPARATION 83

Benzyl 7-alpha-[1-(p-Nitrobenzyloxycarbonyloxy)ethyl]-3-[2-(p-nitrobenzyloxycarbonylamino)ethylthio]-1-beta-oxoceph-3-em-4-carboxylate 2-(p-Nitrobenzyloxycarbonylamino)ethylmercaptan (23.1 mg., 0.05 mmole) and triethylbenzylammonium chloride (11 mg., 0.04 mole) were combined with a mixture of 0.1 N sodium hydroxide (0.5 ml.), water (2 ml.) and methylene chloride (2.5 ml.). Benzyl 7-alpha-[1-(p-nitrobenzyloxycarbonyloxy)ethyl]-3-mesyloxy-1-beta-oxoceph-3-em-4-carboxylate (25 mg., 0.04 mmole) was added and the reaction stirred at room temperature for 16 hours. The layers were separated and the aqueous layer washed with fresh methylene chloride. The organic layers were combined, back-washed with water, dried over anhydrous sodium sulfate, filtered and evaporated to yield product (41 mg.). Chromatography on silica gel (10:1 chloroform:ethyl acetate as eluant) gave purified benzyl 7-alpha-[1-(p-nitrobenzyloxycarbonyloxy)ethyl]-3-[2-(p-nitrobenzyloxycarbonylamino)ethylthio]-1-oxoceph-3-em-4-carboxylate [16 mg.; pnmr/CDCl$_3$/delta includes 2.9 ppm (m, 2H)].

By the same method, substituting the appropriate alcohol/mercaptan for 2-(p-nitrobenzyloxycarbonylamino)ethylmercaptan, the following compounds are prepared:

benzyl 7-alpha-[1-(p-nitrobenzyloxycarbonyloxy)ethyl]-3-ethoxy-1-beta-oxoceph-3-em-4-carboxylate;

benzyl 7-alpha-[1-(p-nitrobenzyloxycarbonyloxy)ethyl]-3-isopropoxy-1-beta-oxoceph-3-em-4-carboxylate;

benzyl 7-alpha-[1-(p-nitrobenzyloxycarbonyloxy)ethyl]-3-(2-benzyloxycarbonylaminoethoxy)-1-beta-oxoceph-3-em-4-carboxylate;

benzyl 7-alpha-[1-(p-nitrobenzyloxycarbonyloxy)ethyl]-3-propylthio-1-beta-oxoceph-3-em-4-carboxylate; and benzyl 7-alpha-[1-(p-nitrobenzyloxycarbonyloxy)ethyl]-3-(2-acetamidoethylthio)-1-beta-oxoceph-3-em-4-carboxylate.

PREPARATION 84

Benzyl 7-alpha-[1-(p-Nitrobenzyloxycarbonyloxy)ethyl]-3-ethylthio-1-beta-oxoceph-3-em-4-carboxylate Mesyloxy oxide of Preparation 81 (25 mg.) was added at 0° C. to a stirred mixture of 5.5 microliters of ethyl mercaptan in a two phase mixture of 3 ml. of methylene chloride, 1 ml. of 0.1 N sodium hydroxide and 2.5 ml. of water and stirred for 8 hours at room temperature. An additional 5.5 microliters of ethyl mercaptan was added and the mixture stored at −78° C. for 16 hours. There was then added 5.5 microliters of ethyl mercaptan, 0.5 ml. of sodium hydroxide and 11 mg. of benzyltriethyl ammonium chloride as catalyst. The reaction was complete within 1 hour at room temperature. The layers were separated and the aqueous layer washed with 3 portions of methylene chloride. The methylene chloride layers were combined and back-washed with water and then brine, dried over anhydrous sodium sulfate, filtered and evaporated to dryness. The residue was chromatographed on silica gel, with 10:1 chloroform:ethyl acetate as eluant and tlc monitoring. Yield 10.6 mg. of title product, $R_f$ 0.5 (ethyl acetate).

PREPARATION 85

Benzyl 7-alpha-[1-(p-Nitrobenzyloxycarbonyloxy)ethyl]-3-[2-(p-nitrobenzylcarbonylamino)ethoxy]-2-diazo-1-beta-oxoceph-3-em-4-carboxylate By the method of Preparation 80, benzyl 7-alpha-[1-(p-nitrobenzyloxycarbonyloxy)ethyl]-3-[2-(p-nitrobenzyloxycarbonylamino)ethoxy]-1-beta-oxoceph-3-em-4-carboxylate is converted to benzyl 7-alpha-[1-(p-nitrobenzyloxycarbonyloxy)ethyl]-3-[2-(p-nitrobenzylcarbonylamino)ethoxy]-2-diazo-1-beta-oxoceph-3-em-4-carboxylate.

By the same method, the other oxy-compounds of Preparation 83 are converted to:

benzyl 7-alpha-[1-(p-nitrobenzyloxycarbonyloxy)ethyl]-2-diazo-3-ethoxy-1-beta-oxoceph-3-em-4-carboxylate; and benzyl 7-alpha-[1-(p-nitrobenzyloxycarbonyloxy)ethyl]-2-diazo-3-isopropoxy-1-beta-oxoceph-3-em-4-carboxylate.

PREPARATION 86

Benzyl 7-alpha-[1-(p-Nitrobenzyloxycarbonyloxy)ethyl]-3-ethylthio-2-diazo-1-1-beta-oxoceph-3-em-4-carboxylate The title ethylthio compound of Preparation 84 (37.5 mg.) was stirred in 10 ml. of water and 10 ml. of methylene chloride and cooled to 5° C. Macrocyclic ether 18 crown 6 (17.2 mg.), benzyltriethylammonium chloride (15.2 mg.), potassium hydroxide (3.7 mg.) and picryl azide (33.7 mg.) were added. The reaction mixture was stirred for 8 hours at 5° C. The methylene chloride layer was washed with ice water and then cold brine, dried over anhydrous sodium sulfate, filtered, and evaporated to dryness. The residue was chromatographed on silica gel with 4:1 chloroform:ethyl acetate as eluant. The yield of title product showing a strong diazo band by ir (2080 cm$^{-1}$) was 10 mg.

By the same method the various thio compounds of Preparation 83 are converted to:

benzyl 7-alpha-[1-(p-nitrobenzyloxycarbonyloxy)ethyl]-3-[2-(p-nitrobenzyloxycarbonylamino)ethylthio]-2-diazo-1-beta-oxoceph-3-em-4-carboxylate;

benzyl 7-alpha-[1-(p-nitrobenzyloxycarbonyloxy)ethyl]-2-diazo-3-propylthio-1-beta-oxoceph-3-em-4-carboxylate; and benzyl 7-alpha-[1-(p-nitrobenzyloxycarbonyloxy)ethyl]-3-(2-acetamidoethylthio)-2-diazo-1-beta-oxoceph-3-em-4-carboxylate.

PREPARATION 87

Ethyl Formamidate Hydrochloride

A mixture of formamide (4.5 g., 4.0 ml., 0.10 mole) and ethanol (4.6 g., 5.8 ml., 0.10 mole) was added dropwise to a solution of benzoyl chloride (14.1 g., 11.7 ml., 0.10 mole) in 70 ml. of ether at 10° C. On stirring the reaction mixture became a slurry. After stirring for 30 minutes, the product was recovered by filtration and dried over P$_2$O$_5$. The yield of ethyl formamide hydrochloride, obtained as a white solid, was 2.46 g.

I claim:

1. A light-catalyzed process of rearranging a 2-diazo-1-oxoceph-3-em-4-carboxylate to a 1-oxocarbapen-2-em-3-carboxylate in a reaction-inert organic solvent in a temperature range of −100° C. to 35° C.

2. A light-catalyzed process of rearranging a compound of the formula

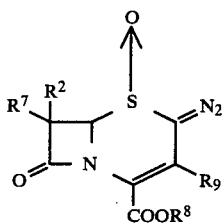

to a compound of the formula

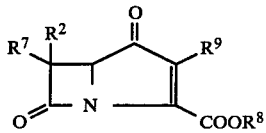

in a reaction-inert solvent in the temperature range −100° C. to 35° C., in which general formulae:

R$^7$ is hydrogen;
    acetamido, mono or disubstituted, wherein carboxy and amino groups are conventionally protected;
    5-methyl-3-phenylisoxazole-4-carboxamido; or

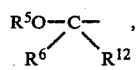

wherein R$^5$ is hydrogen, acetyl, benzyloxycarbonyl or p-nitrobenzyloxycarbonyl,
R$^6$ is hydrogen or (C$_1$–C$_5$)alkyl and R$^{12}$ is hydrogen or methyl;
R$^2$ is hydrogen or methoxy;

with the proviso that when R$^2$ is methoxy, R$^7$ is 2-phenoxyacetamido;
R$^8$ is a conventional carboxy protecting group; and
R$^9$ is methyl, acetoxymethyl, methanesulfonyloxy, OR$^{10}$ or SR$^{10}$, wherein R$^{10}$ is (C$_1$–C$_3$)alkyl, 2-benzyloxycarbonylaminoethyl, 2-acetamidoethyl or 2-(p-nitrobenzyloxycarbonylamino)ethyl.

3. A process of claim 2 wherein, when R$^7$ is acetamido, mono or disubstituted, said acetamido group is: 2-phenoxyacetamido;
D-2-(4-ethyl-2,3-dioxopiperazine-1-carboxamido)-2-phenylacetamido;
D-2-benzyloxycarbonylamino-2-phenylacetamido; or the benzhydryl, benzyl or 2-naphthylmethyl ester of 2-carboxy-2-phenylacetamido.

4. A process of claim 3, wherein R$^8$ is selectively removable by hydrogenolysis.

5. A process of claim 4, wherein R$^8$ is benzyl, benzhydryl or 2-naphthylmethyl.

6. A process of claim 3, wherein R$^8$ is selectively removable by mild zinc reduction.

7. A process of claim 6, wherein R$^8$ is 2,2,2-trichloroethyl.

8. A process of claim 3, wherein R$^8$ is selectively hydrolyzable under physiological conditions.

9. A process of claim 8, wherein R$^8$ is pivaloyloxymethyl, acetoxymethyl, 1,3-dihydro-3-oxobenzo[c]furan-1-yl or 1-ethoxycarbonyloxyethyl.

10. A process of claim 3, in which R$^7$ and R$^2$ are each hydrogen.

11. A process of claim 10, in which R$^9$ is methyl.

12. The process of claim 11, in which R$^8$ is pivaloyloxymethyl.

13. The process of claim 11, in which R$^8$ is benzhydryl.

14. The process of claim 11, in which R$^8$ is 2,2,2-trichloroethyl.

15. A process of claim 3, in which R$^7$ is 2-phenoxyacetamido and R$^9$ is methyl.

16. A process of claim 15, in which R$^8$ is pivaloyloxymethyl.

17. The process of claim 15, in which R$^2$ is hydrogen.

18. A process of claim 3, in which R$^7$ is D-2-(4-ethyl-2,3-dioxopiperazine-1-carboxamido)-2-phenylacetamido, and R$^{10}$ is methyl.

19. The process of claim 18, in which R$^8$ is pivaloyloxymethyl.

20. The process of claim 18, in which R$^8$ is 2-naphthylmethyl.

21. A process of claim 3, in which R$^7$ is 5-methyl-3-phenylisoxazole-4-carboxamido, and R$^9$ is methyl.

22. The process of claim 21, in which R$^8$ is pivaloyloxymethyl.

23. A process of claim 3, in which R$^7$ is 1-acetoxyethyl and R$^9$ is methyl.

24. The process of claim 23, in which R$^8$ is pivaloyloxymethyl.

25. The process of claim 23, in which R$^8$ is benzyl.

26. A process of claim 3, in which R$^7$ is 1-(p-nitrobenzyloxycarbonyloxy)ethyl.

27. The process of claim 26 wherein R$^9$ is methyl and R$^8$ is benzyl.

28. The process of claim 26 wherein R$^9$ is methoxy and R$^8$ is benzyl.

29. The process of claim 26 wherein R$^9$ is 2-(p-nitrobenzyloxycarbonylamino)ethyl and R$^8$ is benzyl.

30. The process of claim 26 wherein R$^9$ is methanesulfonyloxy and R$^8$ is benzyl.

* * * * *